US009469878B2

(12) United States Patent
Boothman et al.

(10) Patent No.: US 9,469,878 B2
(45) Date of Patent: Oct. 18, 2016

(54) METHODS OF TREATING CANCER COMPRISING TARGETING NQO1

(75) Inventors: David Boothman, Austin, TX (US); Jinming Gao, Plano, TX (US); Erik Bey, Austin, TX (US); Ying Dong, Austin, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 222 days.

(21) Appl. No.: 13/820,127

(22) PCT Filed: Sep. 22, 2011

(86) PCT No.: PCT/US2011/052801
§ 371 (c)(1),
(2), (4) Date: May 17, 2013

(87) PCT Pub. No.: WO2012/040492
PCT Pub. Date: Mar. 29, 2012

(65) Prior Publication Data
US 2013/0253046 A1      Sep. 26, 2013

Related U.S. Application Data

(60) Provisional application No. 61/385,411, filed on Sep. 22, 2010.

(51) Int. Cl.
| | |
|---|---|
| G01N 33/574 | (2006.01) |
| C12Q 1/68 | (2006.01) |
| A61K 31/00 | (2006.01) |
| A61K 31/352 | (2006.01) |
| A61K 31/357 | (2006.01) |
| A61K 31/4025 | (2006.01) |
| A61K 31/423 | (2006.01) |
| A61K 31/538 | (2006.01) |
| A61K 45/06 | (2006.01) |
| A61N 5/10 | (2006.01) |
| C12Q 1/26 | (2006.01) |

(52) U.S. Cl.
CPC ............. *C12Q 1/6886* (2013.01); *A61K 31/00* (2013.01); *A61K 31/352* (2013.01); *A61K 31/357* (2013.01); *A61K 31/4025* (2013.01); *A61K 31/423* (2013.01); *A61K 31/538* (2013.01); *A61K 45/06* (2013.01); *A61N 5/10* (2013.01); *C12Q 1/26* (2013.01); *C12Q 2600/106* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS 6,890,950 B2 *   5/2005   Boothman et al. ........... 514/454
6,894,071 B2 *   5/2005   Nuijen ................. A61K 9/0034
                                                424/489

2006/0034796 A1    2/2006   Ashwell
2008/0248097 A1   10/2008   Kwon

FOREIGN PATENT DOCUMENTS

| WO | WO 03/090710 | 11/2003 |
|---|---|---|
| WO | WO 2007/092963 | 8/2007 |
| WO | WO 2012/039855 | 3/2012 |

OTHER PUBLICATIONS

Krajinovic et al (Int J Cancer, 2002, 97:230-236).*
Smitskamp-Wilms et al (British Journal of Cancer, 1995, 72:917-921).*
Kelland et al (Journal of NCI, 1999, 91:1940-1949).*
Djuric et al (J Cancer Research Clinical Oncology, 1990, 116:379-383).*
Wilson et al (Current Eye Research, 2001, 22:348-352).*
Siegel et al (Free Radical Biology & Medicine, 2000, 29:246-253).*
Siegel et al (Clinical Cancer Research, 1998, 4:2065-2070).*
Cordoba-Pedregosa et al (Anticancer Research, 2006, 26:3535-3540).*
Cao et al., "Tumor-selective, futile redox cycle-induced bystander effects elicited by NQO1 bioactivatable radiosensitizing drugs", *Antioxid Redox Signal.*, 21(2):237-50, 2014.
Huang et al., "An NQO1 substrate with potent antitumor activity that selectively kills by PARP1-induced programmed necrosis", *Cancer Res.*, 72(12):3038-3047, 2012.
Bentle et al., "Calcium-dependent modulation of poly(ADP-ribose) polymerase-1 alters cellular metabolism and DNA repair", *J Biol Chem.*, 281:33684-96, 2006.
Bentle et al., "New tricks for old drugs: the anticarcinogenic potential of DNA repair inhibitors", *J Mol Histol*,37:203-18, 2006.
Bentle et al., "Nonhomologous end joining is essential for cellular resistance to the novel antitumor agent, beta-lapachone", *Cancer Res.*, 67(14):6936-45, 2007.
Bey et al., "An NQO1- and PARP-1-mediated cell death pathway induced in non-small-cell lung cancer cells by beta-lapachone", *Proceedings of the National Academy of Science USA*, 104(28):11832-11837, 2007.
Blanco et al., "β-lapachone micellar nanotherapeutics for non-small cell lung cancer therapy", *Cancer Res.*, 70(10):3896-904, 2010.
Choi et al., "Upregulation of NAD(P)H:quinone oxidoreductase by radiation potentiates the effect of bioreductive β-lapachone on cancer cells", *Neoplasia*, 9(8):634-642, 2007.
Dong et al., "Intratumoral delivery of beta-lapachone via polymer implants for prostate cancer therapy", *Clin Cancer Res.*, 15: 131-39, 2009.
Dong et al., "Prostate cancer radiosensitization through poly (ADP-Ribose) polymerase-1 hyperactivation", *Cancer Res.*, 70:8088-96, 2010.
Extended European Search Report issued in European Application No. 11827555.1, dated Feb. 3, 2014.

(Continued)

*Primary Examiner* — Laura B Goddard
(74) *Attorney, Agent, or Firm* — Parker Highlander PLLC

(57) ABSTRACT

Disclosed herein are methods for determining whether an individual with cancer is suitable for a treatment with an NQO1 bioactivatable drug, predicting responsiveness of an individual with cancer to a treatment with an NQO1 bioactivatable drug, and treating an individual with cancer with an NQO1 bioactivatable drug composition.

9 Claims, 32 Drawing Sheets

(56) References Cited

OTHER PUBLICATIONS

Ough et al., "Efficacy of beta-lapachone in pancreatic cancer treatment: exploiting the novel, therapeutic target NQO1", *Cancer Biol Ther.*, 4(1):95-102, 2005.

Pan et al., "Implication of alternative splicing for expression of a variant NAD(P)H:quinone oxidoreductase-1 with a single nucleotide polymorphism at 465C>T", *Pharmacogenetics*, 12(6):479-488, 2002.

Park et al., "Susceptibility of cancer cells to beta-lapachone is enhanced by ionizing radiation", *Int J Radiation Oncology Biol Phys*, 61(1):212-219, 2005.

PCT International Preliminary Report on Patentability issued in International Application No. PCT/US2011/052801, dated Mar. 26, 2013.

PCT International Search Report and Written Opinion issued in International Application No. PCT/US2011/052801, mailed Dec. 12, 2011.

Pink et al., "NAD(P)H:Quinone oxidoreductase activity is the principal determinant of beta-lapachone cytotoxicity", *J Biol Chem.*, 275:5416-24, 2000.

Reinicke et al., "Development of beta-lapachone prodrugs for therapy against human cancer cells with elevated NAD(P)H:quinone oxidoreductase 1 levels", *Clin Cancer Res.*, 11:3055-64, 2005.

Tagliarino et al., "Calcium is a key signaling molecule in beta-lapachone-mediated cell death", *J Biol Chem.*, 276:19150-9, 2001.

Tagliarino et al., "µ-calpain activation in beta-lapachone-mediated apoptosis", *Cancer Biol Ther.*, 2(2):141-52, 2003.

Tan et al., "Evidence for NAD(P)H:quinone oxidoreductase 1 (NQO1)—mediated quinone—dependent redox cycling via plasma membrane electron transport: A sensitive cellular assay for NQO1", *Free Radical Biology and Medicine*, 48:421-429, 2010.

Winski et al., "Relationship between NAD(P)H:quinone oxidoreductase 1 (NQO1) levels in a series of stably transfected cell lines and susceptibility to antitumor quinones", *Biochemical Pharmacology*, 61:1509-1516, 2001.

Wondrak, "NQO1—activated phenothiazinium redox cyclers for the targeted bioreductive induction of cancer cell apoptosis", *Free Radical Biology and Medicine*, 43:178-190, 2007.

Bae et al., "Intelligent polymeric micelles from functional poly(ethylene glycol)-poly(amino acid) block copolymers," *Advanced Drug Delivery Reviews*, 61:768-784, 2009.

Luo et al., "Principles of cancer therapy: oncogene and non-oncogene addiction," *Cell*, 136:823-837, 2009.

Office Action issued in U.S. Appl. No. 13/825,524, mailed Oct. 1, 2015.

Pinto et al., "The trypanocidal activity of naphthoquinones: a review," *Molecules*, 14:4570-4590, 2009.

\* cited by examiner

A.                    B.

C.

MCF-7

METHODS OF TREATING CANCER COMPRISING TARGETING NQO1

CROSS-REFERENCE TO RELATED APPLICATIONS

This application is a National Stage of PCT/US2011/052801, filed Sep. 22, 2011, which claims the benefit under 35 U.S.C. §119(e) of U.S. Provisional patent application Ser. No. 61/385,411, filed on Sep. 22, 2010, the contents of each which are incorporated herein by reference in their entirety.

STATEMENT AS TO FEDERALLY SPONSORED RESEARCH

This invention was made with government support under NIH RO1 CA102792 and NIH RO1 CA102792-08, awarded by the National Institutes of Health, and DOD W81WH-06-1-0198, W81XWH-05-1-0248, and W81XWH-04-1-0301 awarded by the Department of Defense. The government has certain rights in the invention.

FIELD OF THE INVENTION

This invention provides methods for determining whether an individual with cancer is a suitable candidate for treatment with an NQO1 bioactivatable drug, predicting the responsiveness of an individual with cancer to a treatment with an NQO1 bioactivatable drug, and treating an individual with cancer with an NQO1 bioactivatable drug composition.

BACKGROUND OF THE INVENTION

Cancers in the form of malignant tumors are the second leading cause of death in the United States after heart disease (U.S. Dept. of Health and Human Services, National Vital Statistics Reports, 58(19), May 20, 2010). Many cancers are characterized by an increase in the number of neoplastic cells originating from an initially normal tissue which subsequently propagate to form a tumor mass. With malignant tumors, neoplastic cells invade neighboring tissues ultimately leading to their spread via the blood or lymphatic system to lymph nodes and other locations distant from the site of the original tumor via a process called metastasis. Cancer manifests itself in a wide variety of forms, with each form characterized by varied degrees of invasiveness and aggressiveness.

NQO1 bioactivatable drugs are metabolized by the enzyme NQO1 in a futile manner to generate a series of cytotoxic factors, such as reactive oxygen species (ROSs) or quinone-based drug metabolites that cause damage to DNA, typically by alkylation. One such NQO1 bioactivatable drug, beta-lapachone (3,4-dihydro-2,2-dimethyl-2H-naphtho[1,2-b]pyran-5,6-dione; β-lap), is a naturally-occurring quinone obtained from the bark of the Lapacho tree (*Tabebuia vellanedae*), which is native to Central and South America. The anti-cancer activity of β-lap is due to two-electron reduction of β-lap mediated by NAD(P)H: quinone oxidoreductase (NQO1, DT-diaphorase) using NADH or NAD(P)H as electron sources (Pardee et al., *Curr Cancer Drug Targets*, 2002, 2(3):227-42). In cells that express NQO1, the β-lap molecule undergoes a futile cycle resulting in reactive oxygen species (ROS) generation leading to eventual DNA single-strand breaks, hyperactivation of poly(ADP-ribose) polymerase-1 (PARP-1), loss of NAD+ and ATP pools, and a unique pattern of cell death referred to as "programmed necrosis" or "necroptosis" (Blanco et al., *Cancer Res.* 2010, 70(10):3896-904; Bentle et al., *J Mol Histol,* 2006; 37:203-18). Necroptosis is a unique form of cell death that has attributes of both apoptosis (e.g., terminal deoxynucleotidyl transferase-mediated dUTP nick end labeling (TUNEL) positive and chromatin and nuclear condensation) and necrosis (e.g., caspase and energy independent) (Bentle et al., *J Mol Histol,* 2006; 37:203-18). However, not all cancer cells respond to treatment with β-lap (Bentle et al., *Cancer Res.,* 2007, 67(14):6936-45) and its non-specific distribution can lead to low tumor concentrations and systemic toxicity (Ough et al., *Cancer Biol Ther.,* 2005, 4(1):95-102).

Biomarkers are gene expression products measured in a tissue or specific cell type whose concentration, presence, or lack thereof can indicate the presence or seriousness of a disease state. For cancer, identification of tumor-associated biomarkers has in some cases permitted the specific targeting of cancer cells based on the differential relative expression of one or more particular biomarkers expressed by a cancer cell. However, even within tumors originating from the same tissue type, considerable variations can exist within gene expression patterns between individuals or between subpopulations of individuals suffering from identical forms of cancer. Indeed, genome-wide gene expression profiling has permitted the molecular characterization of intertumoral gene expression variability, demonstrating specific molecular signatures that reflect underlying pathogenic mechanisms and molecular features that may be associated with survival in individual subtypes of tumors (Alizedeh et al, 2000, *Nature,* 403:503-511). Identification of tumor subtypes is critical, as anti-cancer therapies that may be effective for the treatment of one subtype may not be similarly effective in treating other subtypes due to the consequences of variation in gene expression patterns.

Consequently, given the variability of individual gene expression within tumors of the same cancer type, there exists a need for biomarkers whose expression can be used to select individuals or subpopulations of individuals for a particular anti-cancer therapy, such as β-lap, and whose measurement can not only predict the likelihood that an individual with a particular tumor subtype will benefit from a particular anti-cancer therapy, but whose expression is also useful for selecting individuals or subpopulations of individuals for that specific anti-cancer therapy. Such diagnostic markers could be used to guide health care professionals involved in the treatment of an individual suffering from particular subtypes of malignant tumors originating from the same tissue. Diagnostic markers of this sort would also be useful to track prognosis following the initiation of treatment with a specific treatment, such as treatment with NQO1 bioactivatable drugs such as β-lap.

Throughout this specification, various patents, patent applications and other types of publications (e.g., journal articles) are referenced. The disclosure of all patents, patent applications, and publications cited herein are hereby incorporated by reference in their entirety for all purpose

BRIEF SUMMARY OF THE INVENTION

The invention provided herein discloses, inter alia, methods for using the expression levels of NQO1 and/or catalase in tumor cells to select individuals or subpopulations of individuals with cancer that will benefit from treatment with an NQO1 bioactivatable drug. Also provided herein are methods for predicting the responsiveness of an individual with cancer to a treatment with an NQO1 bioactivatable drug based on the expression levels of NQO1 and/or catalase in tumor cells from that individual.

In one aspect, provided herein are methods for determining whether an individual with cancer is suitable for a treatment with an NQO1 bioactivatable drug, comprising measuring the level of NQO1 expression and catalase expression in the cancer cells in the individual, wherein a ratio of the NQO1 level over the catalase level in the cancer cells from the individual being at least about 50-fold of the ratio of a normal tissue indicates that the individual is suitable for the treatment.

In another aspect, provided herein are methods of predicting responsiveness of an individual with cancer to a treatment with an NQO1 bioactivatable drug, comprising measuring the level of NQO1 expression and catalase expression in the cancer cells in the individual, wherein a ratio of the NQO1 level over the catalase level in the cancer cells from the individual being at least about 50-fold of the ratio of a normal tissue indicates that the individual is more likely to be responsive to the treatment.

In another aspect, provided herein are methods of treating an individual with cancer, comprising administering an effective amount of an NQO1 bioactivatable drug to the individual, wherein the individual is selected for the treatment if the ratio of the NQO1 expression level over the catalase expression level in the cancer cells from the individual is at least about 50-fold of the ratio in a normal tissue.

In some embodiments, the ratio of the NQO1 expression level over the catalase expression level in the cancer cells from the individual is at least about 55-fold, at least about 60-fold, at least about 65-fold, at least about 70-fold, at least about 80-fold, or at least about 90-fold of the ratio of a normal tissue. In some embodiments, the cancer cells and normal tissue are from the individual. In some embodiments, the normal tissue is associated normal tissue.

In another aspect, provided herein are methods of determining whether an individual with cancer is suitable for a treatment with an NQO1 bioactivatable drug, comprising measuring the protein level of NQO1 expression in the cancer cells from the individual, wherein the NQO1 enzymatic activity≥about 50 units in the cancer cells indicates that the individual is suitable for the treatment.

In another aspect, provided herein are methods of predicting responsiveness of an individual with cancer to a treatment with an NQO1 bioactivatable drug, comprising measuring the protein level of NQO1 expression in the cancer cells from the individual, wherein the NQO1 enzymatic activity≥about 50 units in the cancer cells indicates that the individual is more likely to be responsive to the treatment.

In another aspect, provided herein are methods of treating an individual with cancer, comprising administering an effective amount of an NQO1 bioactivatable drug to the individual, wherein the individual is selected for the treatment if the NQO1 enzymatic activity in the cancer cells of the individual is ≥about 50 units.

In some embodiment, NQO1 enzymatic activity in the cancer cells of the individual is ≥about 60 units, ≥70 units, ≥80 units, or ≥90 units.

In another aspect, provided herein are methods of determining whether an individual with cancer is suitable for a treatment with an NQO1 bioactivatable drug, comprising detecting the presence or absence of a NQO1 gene polymorphism C465T mutation in a sample from the individual, wherein the presence of C465T/C465T polymorphism indicates that the individual is suitable for the treatment.

In another aspect, provided herein are methods of predicting responsiveness of an individual with cancer to a treatment with an NQO1 bioactivatable drug, comprising detecting the presence or absence of a NQO1 gene polymorphism C465T mutation in a sample from the individual, wherein the presence of C465T/C465T polymorphism indicates that the individual is likely to be responsive to the treatment.

In yet another aspect, provided herein are methods of treating an individual with cancer, comprising administering an effective amount of an NQO1 bioactivatable drug to the individual, wherein the individual is selected for the treatment based on the presence of C465T/C465T polymorphism in a sample from the individual.

In another aspect, provided herein are methods for treating cancer in an individual in need thereof, comprising administering DNA damaging therapy to an individual in need thereof and an NQO1 bioactivatable drug.

Disclosed herein, in certain embodiments, are methods of using NQO1 bioactivatable drugs, such as β-lap, for cancer therapy.

Disclosed herein, in certain embodiments, are methods for treating cancer in an individual in need thereof, comprising administering a DNA damaging therapy to an individual in need thereof and an NQO1 bioactivatable drug. In some embodiments, the method further comprises determining the NQO1 status of the individual, wherein the NQO1 bioactivatable drug is administered to the individual if the cancer is NQO1 positive and not administered to the individual if the cancer is NQO1 negative. In some embodiments, the tumor is exposed to the β-lap formulation for at least 2 hours. In some embodiments, the tumor is not exposed to the β-lap formulation for more than 12 hours. In some embodiments, the doses of DNA damaging therapies are sub-threshold or standard. In some embodiments, the DNA damaging therapy is ionizing radiation, chemotherapeutics or photodynamic (PDT) therapeutics. In some embodiments, the NQO1 bioactivatable drug is administered at the same time as the ionizing radiation treatment. In some embodiments, the ionizing radiation treatment is immediately followed by the NQO1 bioactivatable drug treatment. In some embodiments, the ionizing radiation treatment and the NQO1 bioactivatable drug treatment are within about 2 to about 24 hours. In some embodiments, the NQO1 bioactivatable drug is β-lap, streptonigrin, or DNQ. In some embodiments, the NQO1 bioactivatable drug is a prodrug. In some embodiments, the NQO1 bioactivatable drug is formulated with cyclodextrins or with micelles. In some embodiments, the NQO1 bioactivatable drug is formulated with SPIO-micelles; ligand-encoded (e.g., $\alpha_v\beta_3$) micelles. In some embodiments, the cancer is a solid cancer. In some embodiments, the cancer is non-small cell lung, prostate, breast, pancreatic, colon cancer, or melanoma.

regimen. Treatments (arrows) were administered as indicated. Results are means. (b). Kaplan-Meier survival curves evaluated the toxicity of HCβCD-β-lap treatments alone. HCβCD, as well as 20 mg/kg and 30 mg/kg, HCβCD-β-lap treatments were non-toxic and not statistically different.

Figure 13:
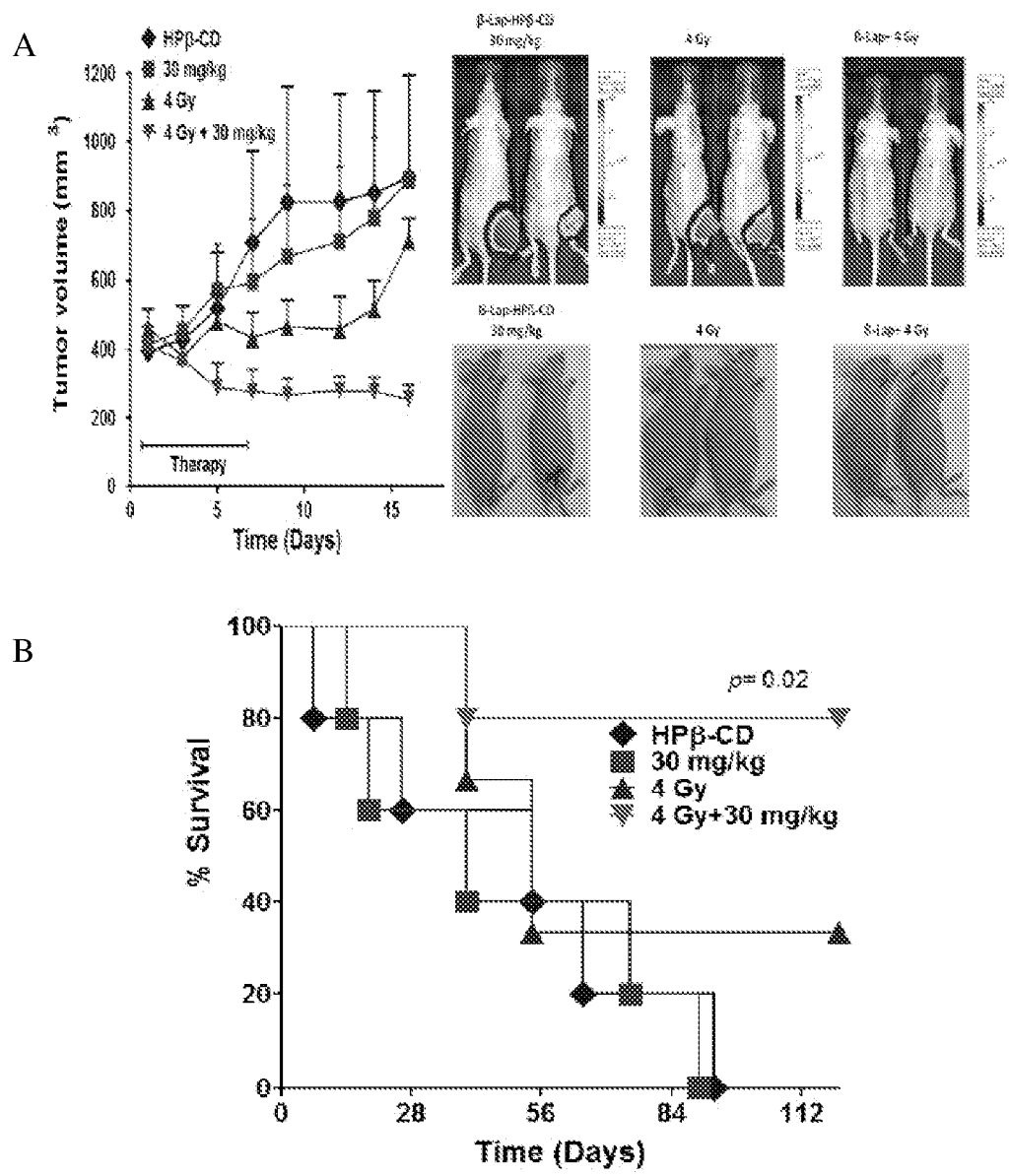

FIG. 13 depicts β-Lapachone radiosensitization of NSCLC xenografts. (a) Athymic mice bearing NSCLC xenografts were irradiated with 4 Gy and treated with 30 mg/kg β-lap-HPβCD vs IR or β-lap alone iv once every other day for a total of 5 treatments in one regimen as indicated. Results from one regimen of therapy are shown. (b) Kaplan-Meyer survival curve of mice treatment with 4 Gy+30 mg/kg.

Figure 14:
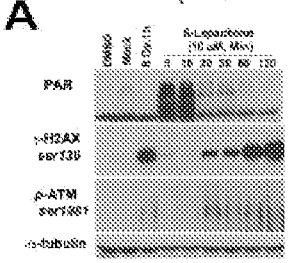
Figure 14:
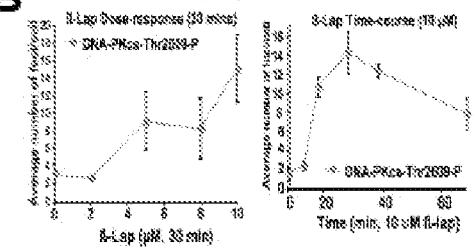
Figure 14:
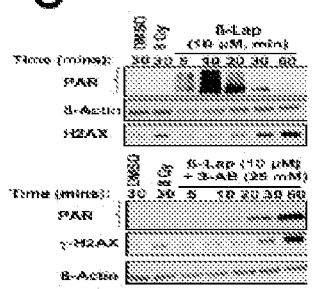
Figure 14:
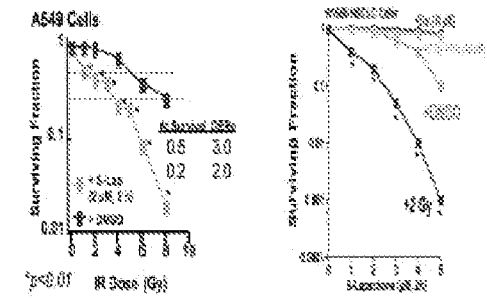
Figure 14:
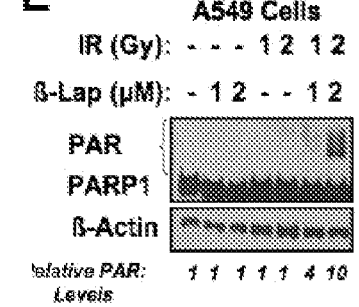
Figure 14:
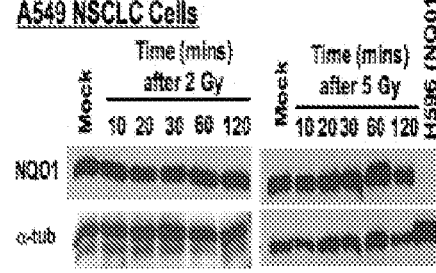

FIG. 14 depicts β-Lapachone radiosensitization of NSCLC cells through hyperactivation of PARP1. In (a), β-lap exposure of NQO1+A549 cells results in hyperactivation of PARP1 as seen by PAR formation. Note that DSB formation, measured by γH2AX and phosphoSer$^{1981}$-ATM was significantly delayed in β-lap-treated cells and occurred after PAR formation decreased. In (b), Phospho-Thr$^{2609}$-DNA-PKcs formation after β-lap in dose and time manners. In (c), Addition of 25 mM 3-aminobenzamide, a PARP1 inhibitor, spares and delays PAR formation in A549 NSCLC cells. In (d), Radiosensitization of A549 and NQO1+H596 NSCLC cells by β-lap. In (e), PAR formation in cells treated with 1 Gy+2 μM β-lap, but not in cells treated with either agent alone. In (f), NQO1 levels are not altered after IR in A549 NSCLC cells, strongly suggesting that NQO1 activity, but not induction, is required for β-lap-mediated radiosensitization.

Figure 15:
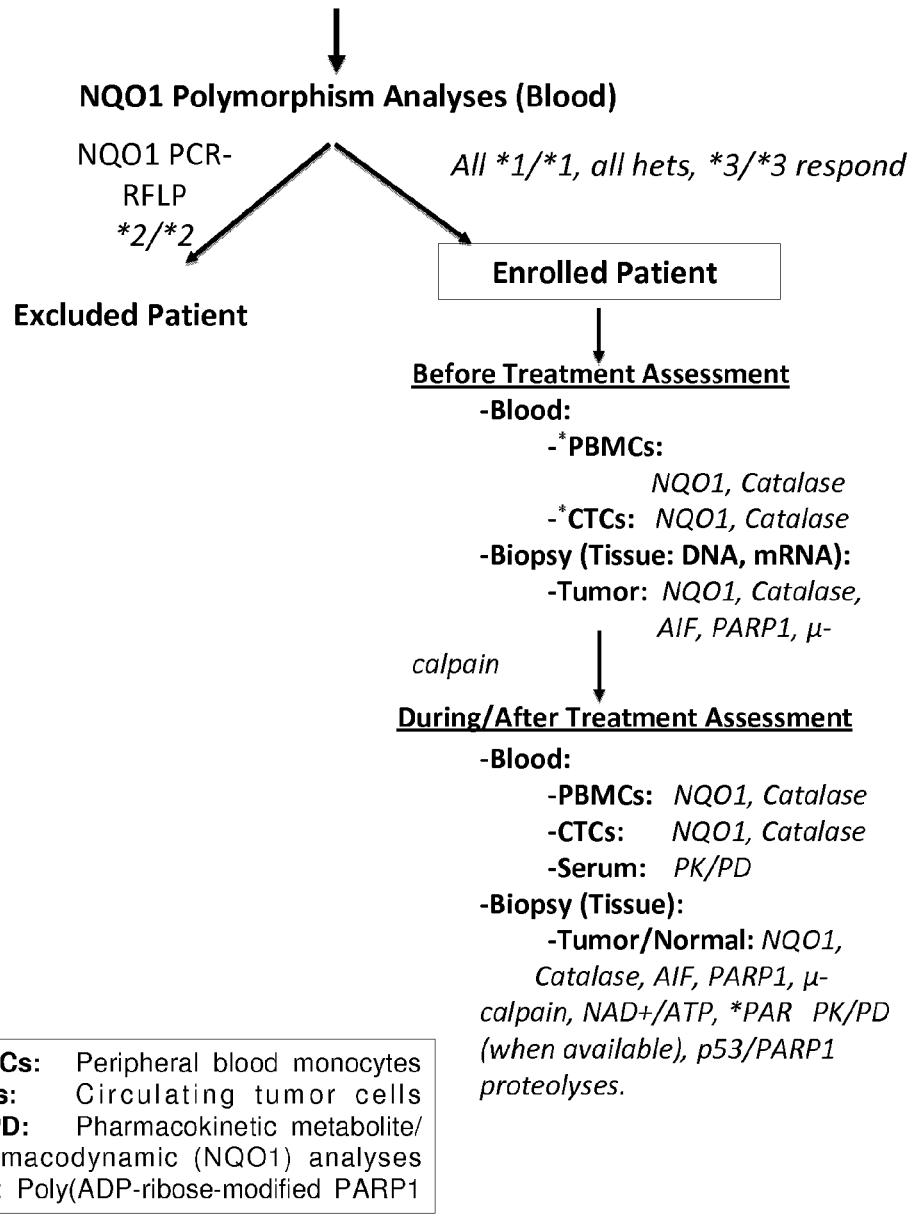

FIG. 15 depicts overview of individualized therapy screening for use of NQO1 bioreactive drugs. Step 1 determines NQO1 polymorphism in patients with NSCLC, breast, prostate, colon, or pancreatic cancer. Step 2 determines the ratio of NQO1:catalase expression that correlates with cytotoxicity in PBMCs and tumor responses in CTCs and patient tumors. Signature expression of a specific set of proteins (NQO1, PARP-1, catalase, AIF, and μ-calpain) in tumors, and in particular increased expression of these proteins can be assessed for 'predictors of response. Finally, before and after expression of specific events (ATM and H2AX phosphorylation, PAR formation, NAD+/ATP losses, and p53 and PARP-1 proteolytic responses) will be assessed to determine tumor responses in patients treatment with NQO1 bioactivatable drugs.

Figure 16:
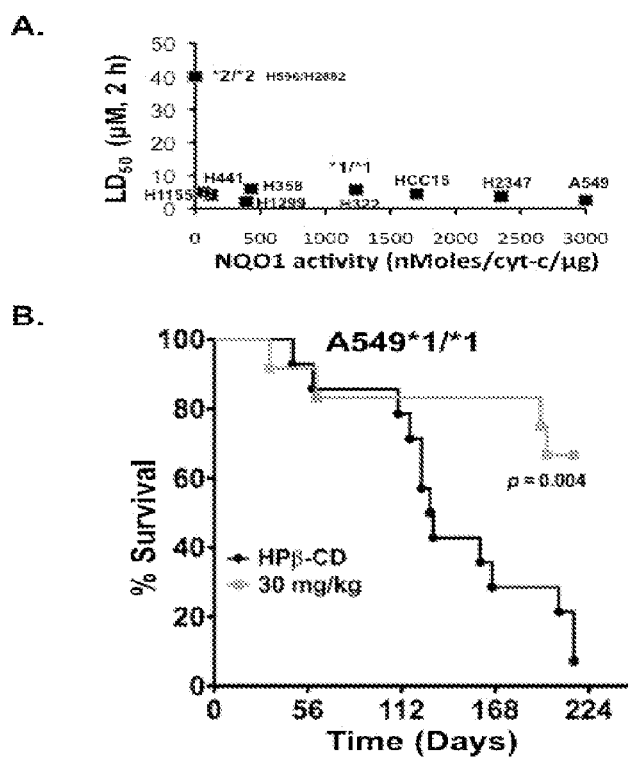

FIG. 16 depicts NQO1 levels predict response to NQO1 bioactivatable therapies. In (a) $LD_{50}$ responses of non-small cell lung cancer (NSCLC) cell lines treated with β-Lap for 2 h and harvester 7 days later. $LD_{50}$ responses were plotted as a function of NQO1 enzymatic levels. The notations, *1/*1 and *2/*2 represent the NQO1 status of each cell line as homozygous wild type (*1/*1) or homozygous polymorphic (*2/*2) genotypes. Note that all heterozygote cells containing one wild-type allele (*1) are wild-type, phenotypically, for NQO1 expression, such that only homozygous *2/*2 or 3/3 are considered non-responsive to NQO1 bioactivatable drugs. Note the high resistance of H596 and H2862 cell lines to β-lapachone compared to all of the wild-type *1/*1 cells with LD50 values less than 5 μM. Note also that *3/*3 SNPs in NQO1 are far more rare than *2/*2 single point mutations in NQO1. In (b), Kaplan-Meier survival curve of mice bearing orthotopic lung tumors implanted with *1/*1 A549 cells. Mice were treated intravenously (5 doses every other day) with β-lap-HPβ-CD or vehicle alone (HPβ-CD). Similar studies with *2/*2 or *3/*3 tumors were performed and these tumors were non-responsive to β-lapachone or other NQO1 bioactivatable drug therapies.

Figure 17:
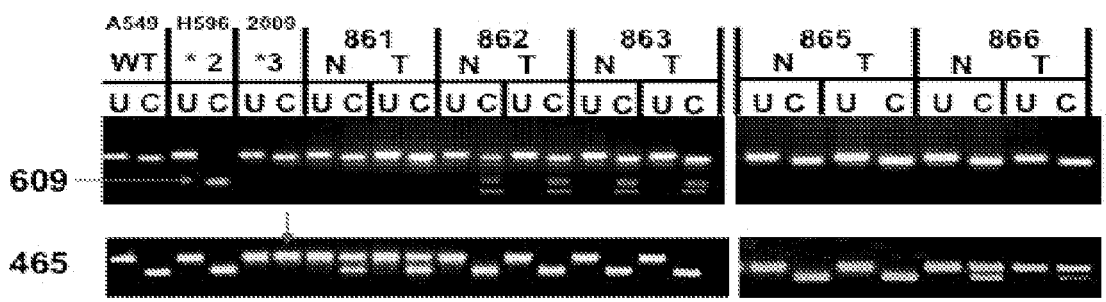

FIG. 17 depicts PCR analysis of genomic DNA for NQO1 polymorphism. Genomic DNA isolated from cell lines (A549, H596 or H2009) and NSCLC patient (861, 862, 863, 865, 866) samples were amplified by PCR reactions with primer sets designed (see text) to identify known polymorphic sites in the gene that encodes NAD(P)H:quinone oxidoreductase 1 (NQO1). Arrows indicate positive restriction sites for *2 (nucleotide 609, upper gel) or lack of restriction site for *3 (nucleotide 465 lower gel). Normal and tumor patient samples (861, 862, 863, 865 and 866) were subjected to the same process as cell line controls. Note patient sample 865 is wild-type for NQO1. In contrast, patients 862 and 863 are heterozygous for *2 and patient samples 861 and 866 are heterozygous *3.

Figure 18:
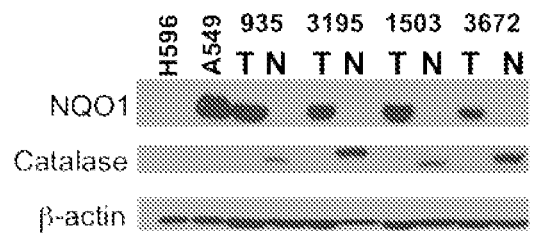

FIG. 18 depicts Western blot analyses for expression of NQO1 and catalase in paired tumor (T) and associated normal tissue (N) NSCLC patient samples. H596 cancer cells are known NQO1*2 polymorphic cells, where A549 NSCLC cells express endogenously elevated levels of NQO1. Patient samples (935, 3195, 1503 and 3672) from NSCLC tumor (T) and associated normal (N) tissue were assessed compared to β-actin used as a loading control.

Figure 19:
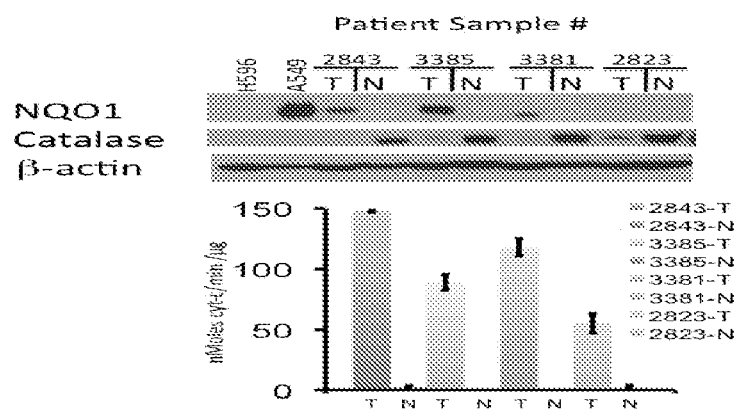

FIG. 19 depicts identification of patients with low ratios of NQO1:Catalase that could still be treated with NQO1 bioactivatable drugs alone as well as in combination with X-irradiation or other standard of care chemotherapies. N, normal tissue; T, NSCLC tumor tissue.

Figure 20:
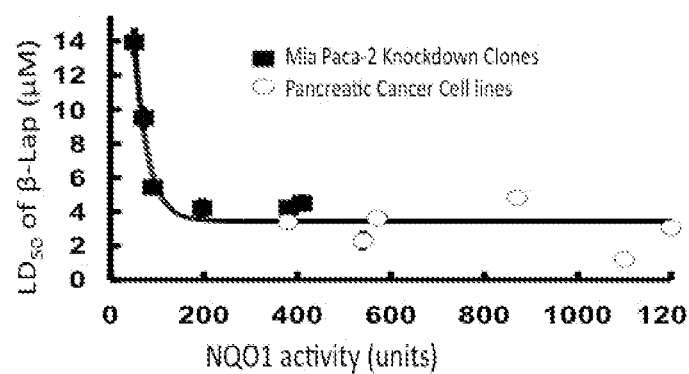

FIG. 20 depicts MiaPaca pancreatic cancer cells exposed to lentiviral shRNA knockdown of NQO1. Clones (closed symbols) varying NQO1 levels were isolated and treated with β-lapachone. The data demonstrate that ~90 units of NQO1 activity are required for efficacious antitumor activity, measured by $LD_{50}$ values. Open symbols represent a series of other pancreatic cancer cell lines derived from patient material that have sufficient NQO1 levels for lethality to β-lap. Some of these cell lines had NQO1 activities comparable to patient #2823 by enzymatic activities. Thus, the inventors would predict that patient #2823 has sufficient NQO1 enzymatic activity (>50 units, FIG. 3) and a low NQO1:Catalase ratio in normal tissue that this patient would be amenable to treatment with NQO1 bioactivatable drugs as suggested in this invention.

Figure 21:
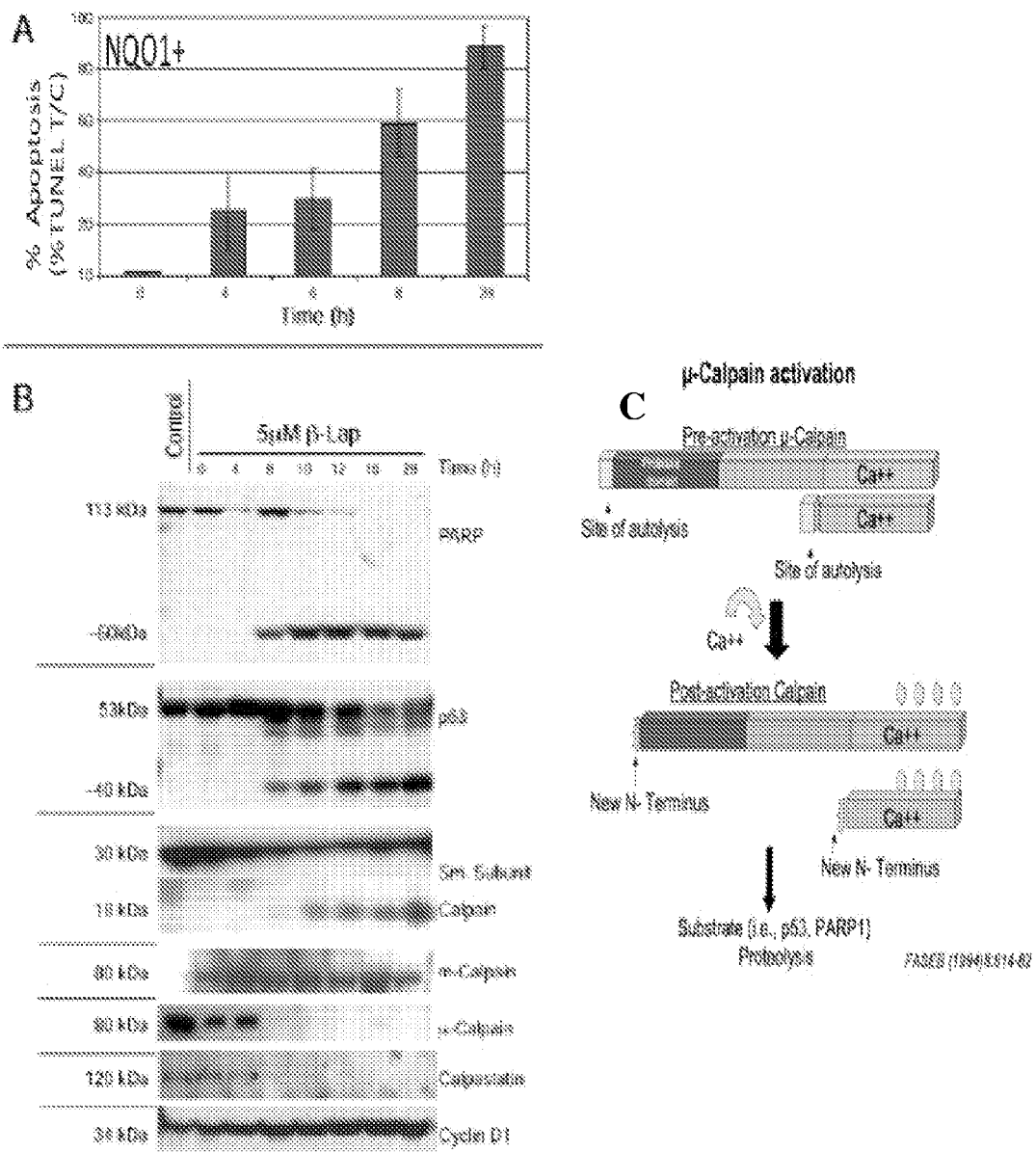

FIG. 21 depicts diagnostic proteolytic responses of MDA-MB-231 NQO1+ cells to NQO1 bioactivatable drugs (ie., β-lapachone) during programmed necrosis. MDA-MB-231 cells were transfected with NQO1 or vector alone. Tissue culture or tumor tissue responses to β-lapachone include: (a) atypical PARP-1 and p53 proteolytic cleavage; (b) cleavage of large and small subunits of μ-calpain, and formation of active 30 kDa μ-calpain and loss of the small subunit of 80 kDa μ-calpain; and (c) loss of the endogenous μ-calpain inhibitor, calpastatin. Note that cyclin D1 levels are not altered as cell death induced by β-lapachone is not cell cycle regulated. NQO1-231 tumors did not respond to β-lapachone.

Figure 22:
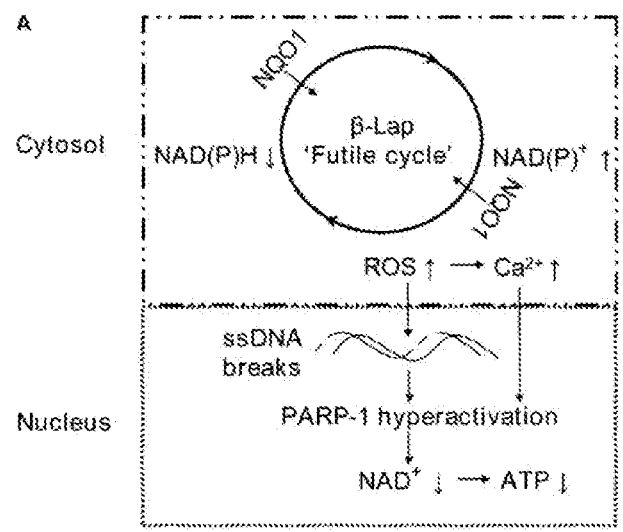

FIG. 22 depicts an illustration of the NQO1-dependent mechanism of β-lap tumor cell killing.

Figure 23:
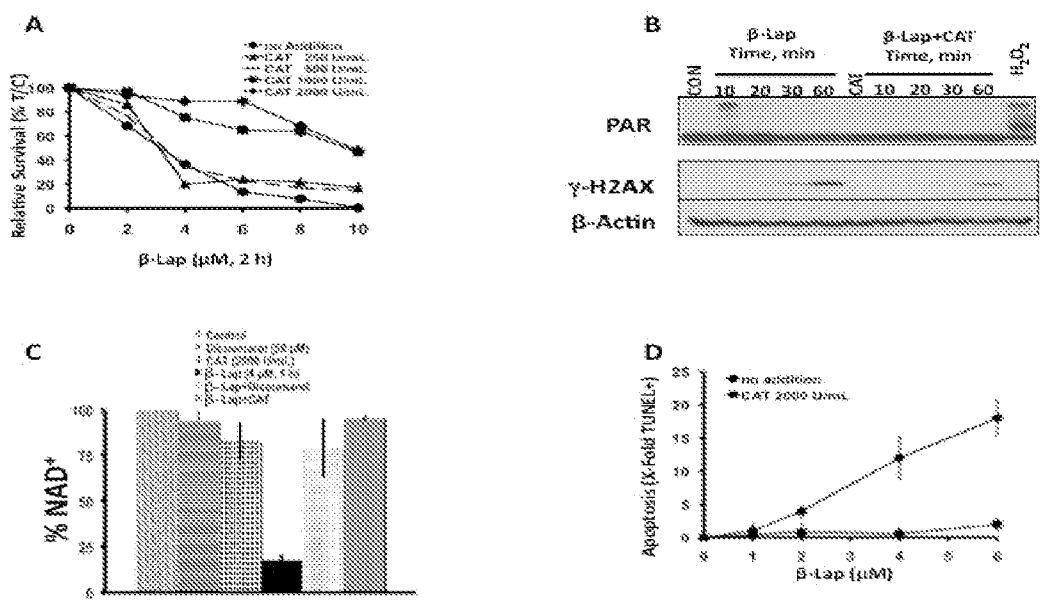

FIG. 23 depicts catalase inhibition of signature cell death responses mediated by β-lapachone. In (a), long-term survival assessment. Cells seeded in 48 well dishes (2500 cells/mL) were treated with varying doses of β-lap with or without catalase co-treatment as indicated. Survival was assessed 7 days later. In (b), Western-blot analyses of PAR-formed PARP1 in cells treated with or without β-lap 4

μM or β-lap+catalase co-treatment (2000 U/mL). In (c), Analyses of % NAD+ loss after exposure 1 h exposure to β-lap or β-lap+/−co-treatment with varying inhibitors (including catalase 2000 U/mL) as indicated. Controls include DMSO, dicoumarol alone and catalase alone as indicated. In (d), Apoptosis assessed by TUNEL assays. Cell were treated with β-lap or β-lap+catalase (2000 U/mL) for 2 h. Drug media were removed and cells were harvested after 24 h and analyzed for fold increase in apoptosis vs vehicle alone treated cells.

Figure 24:
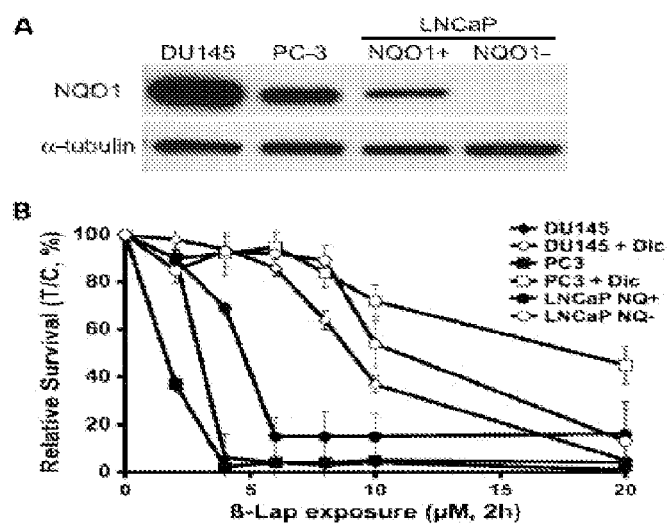

FIG. 24 depicts β-Lap killing human prostate cancer cells in an NQO1-dependent manner. (a) NQO1 expression in prostate cancer cell lines. (b) Relative survival assays of 3 different cell lines exposed to β-Lap alone or with dicoumarol, an NQO1 inhibitor. From Dong Y et al. *Clin Cancer Res* 2009; 15:131-39.

Figure 25:
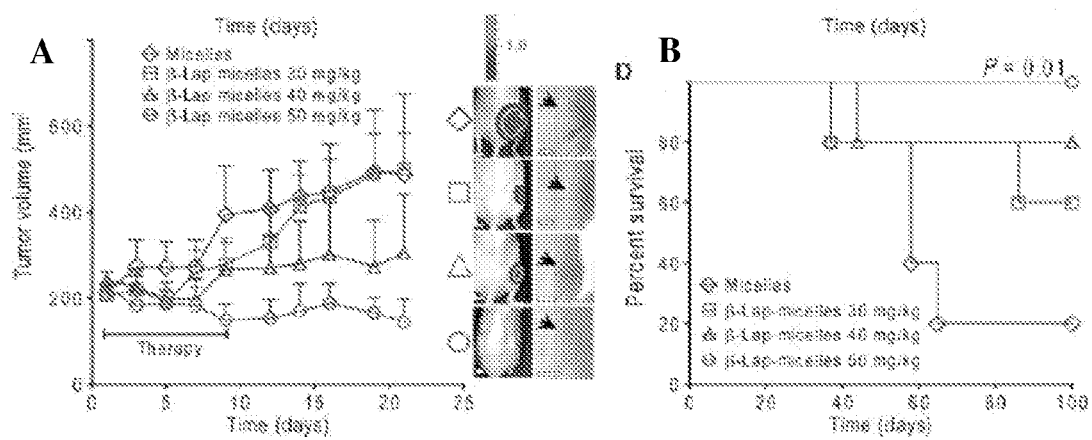

FIG. 25 depicts the antitumor efficacy of β-lap micelles in athymic mice bearing SC A549 NSCLC xenografts. (a) tumor volumes. (b) animal survival.

Figure 26:
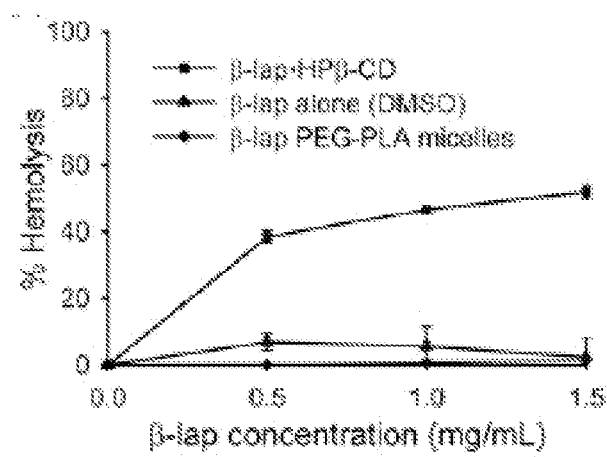

FIG. 26 depicts hemolysis by HPβCD and not β-lapachone. Human (shown) or mouse rbs were incubated with HPβCD alone or HPβCD-β-lap, or β-lap alone in DMSO. Only HPβCD alone caused significant hemolyses.

Figure 27:
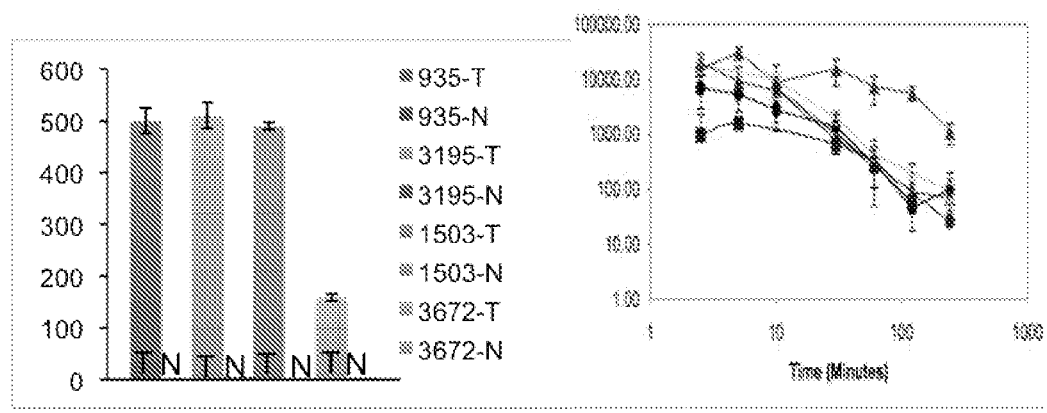
Figure 27:
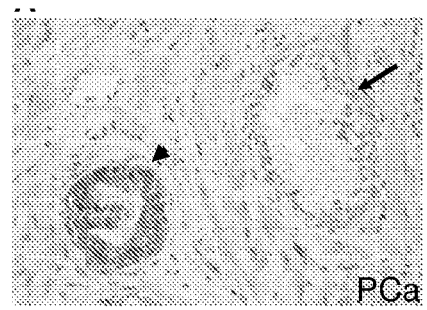

FIG. 27 depicts correlative studies of NQO1 expression and β-lap, a bioactivatable drug. (a) NQO1 activity assay (reported as nMoles cyt-c/min/μg protein) in paired tumor (T) and associated normal tissue (N) from human NSCLC patient samples. NQO1 activity was not detectable in normal lung tissue. (b) β-Lap pharmacokinetic (PK) analyses in athymic nude mice. Black circles denote plasma concentrations (ng/mL); other colors denote various organ/tumor concentrations (ng/g). Note the elevated levels of the drug in lung. (c) NQO1 expression by immunohistochemistry (IHC). Arrowhead denotes NQO1+ prostate cancer cells. Arrow denotes normal prostate gland tissue that have low, or no, detectable NQO1 protein levels.

Figure 28:
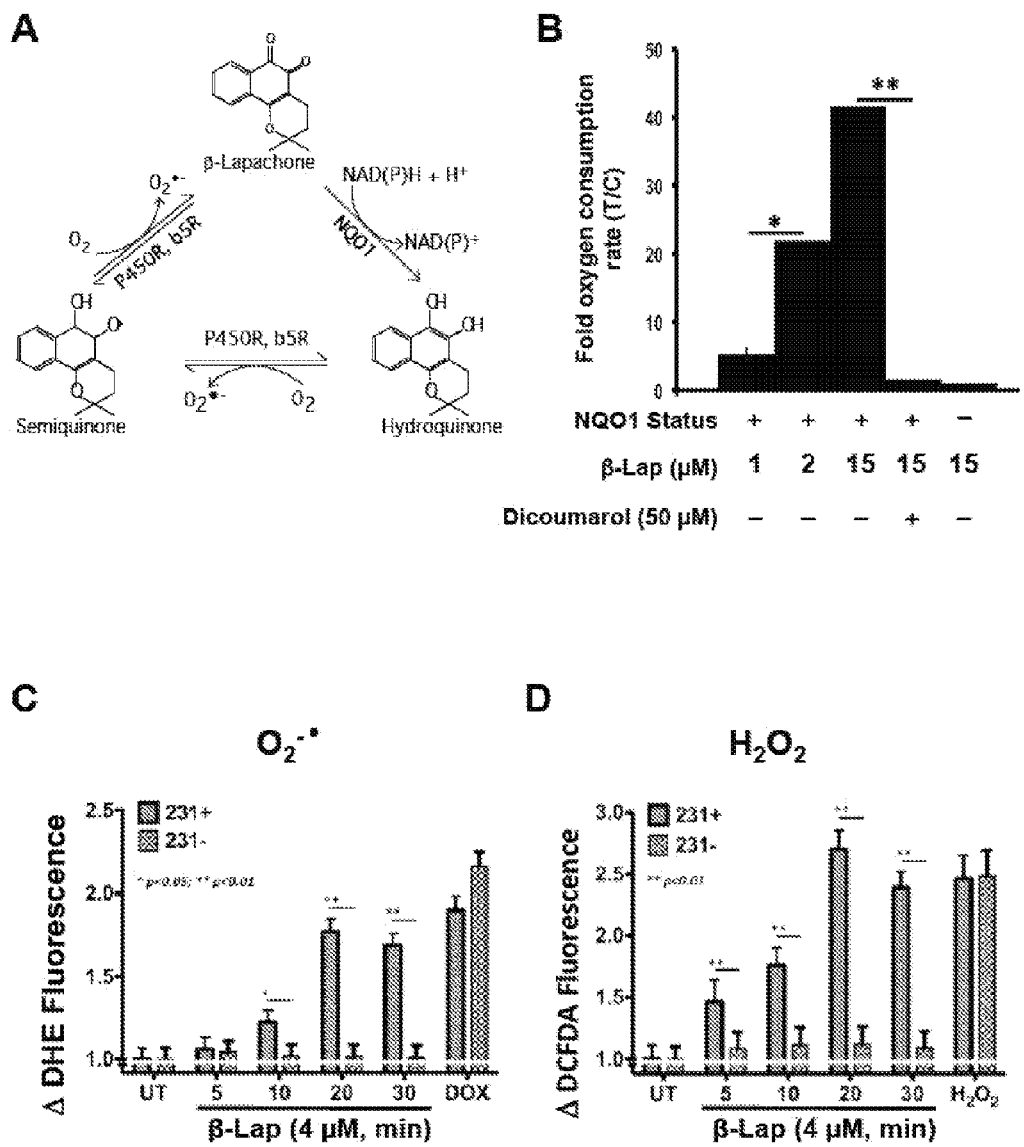

FIG. 28 depicts NQO1 dependent futile cycling of β-lap induces oxygen consumption and ROS formation. In (a), prior data suggested the following metabolism of β-lap by NQO1: β-Lap undergoes a futile redox cycle with NQO1 wherein the hydroquinone form is unstable. Through two one-electron oxidation steps the hydroquinone spontaneously reverts back to the parent β-lap molecule. Theoretically, the two back reactions require oxygen to accept electrons, forming two molecules of superoxide ($O_2^{\bullet-}$) in the process. This cycling "bioactivates" β-lap, resulting in a $Ca^{2+}$-dependent, μ-calpain-mediated cell death in which p53 and PARP-1 are selectively cleaved. In (b), cell extracts from 231-NQ+ or 231-NQ− cells were placed in a closed system with 1, 2 or 15 μM β-lap, ±dicoumarol addition. $O_2$ consumption was measured with an Ocean Optics $O_2$ sensor as described in "Materials and Methods." Data were graphed as fold rate of oxygen consumption of NQO1+S9 over NQO1−S9 β-lap-treated cells±SEM from three independent experiments, *$p \leq 0.005$ (1 μM β-lap to 2 μM β-lap), **$p \leq 0.07$ (15 μM β-lap±50 μM dicoumarol). $O_2$ consumption was attributed to β-lap futile cycling, forming ROS. Each bar represents means±SEM of two independent experiments performed in triplicate. In (c-d), 231-NQ+ and 231 NQ− cells, following β-lap exposures for varying times, were analyzed to determine the species of ROS formed at the indicated times. Quantification of micrographs from cells post β-lap treatment stained with DHE in (c) (for $O_2$— formation) or DCFDA in (d) (ROS formation, primarily $H_2O_2$) was performed as described previously and in "Materials and Methods." Student's t-test were performed to determine whether significant differences existed between means of individual treatments from experiments performed in triplicate and repeated 3 times.

Figure 29:
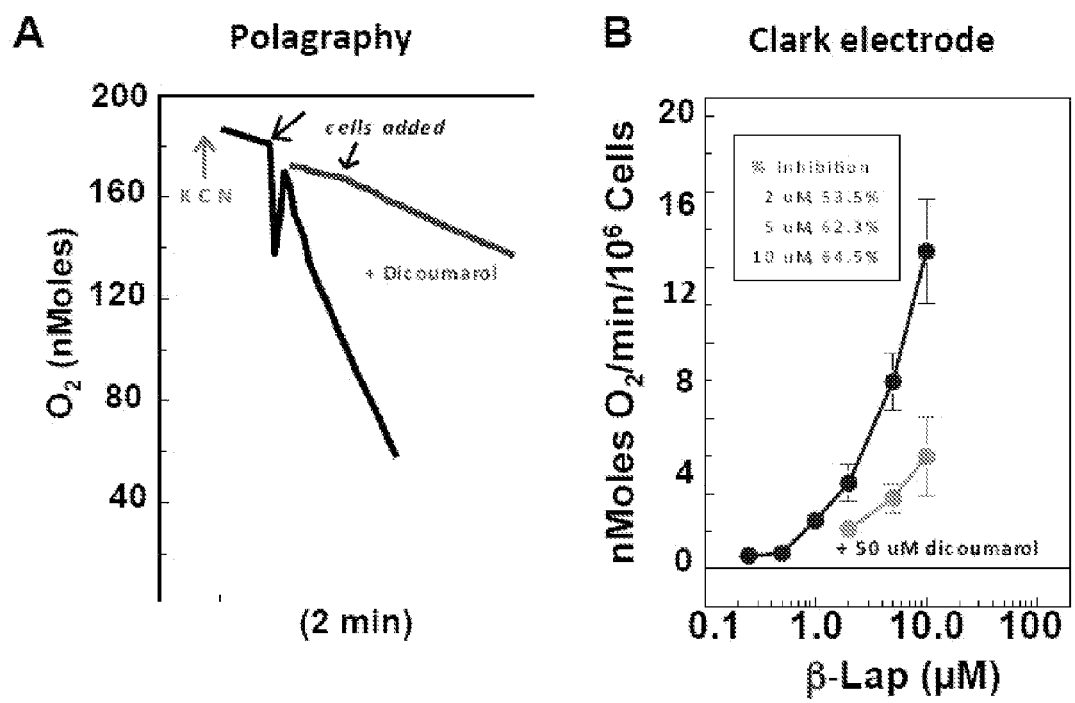

FIG. 29 depicts inhibition of oxygen consumption by dicoumarol in β-lap treated MCF-7 cells. In (a), polagraphy shows significant oxygen consumption following potassium cyanide administration in β-lap treated MCF-7 cells. In (b), a Clark Electrode was used to determine moles of dissolved oxygen used following treatment of MCF-7 cells with varying doses of β-lap. In (a) and (b), dicoumarol (an NQO1 inhibitor) blocked oxygen consumption, suggesting NQO1 mediated oxygen utilization occurs in response to β-lap administration in MCF-7 cells.

Figure 30:
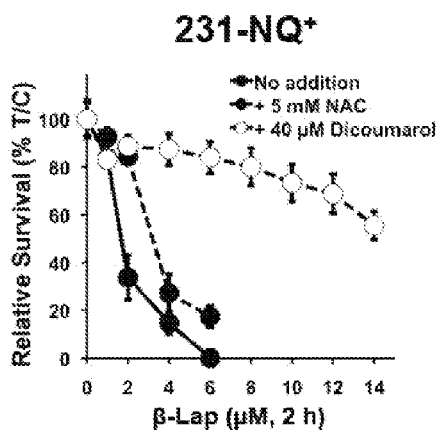
Figure 30:
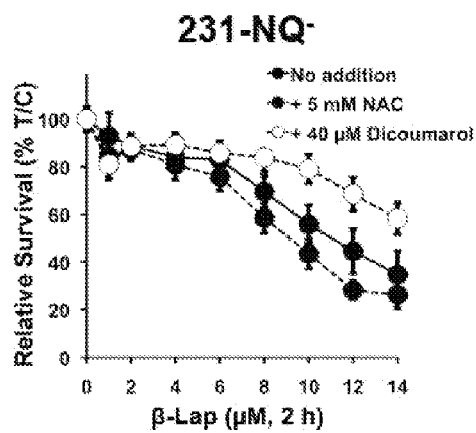
Figure 30:
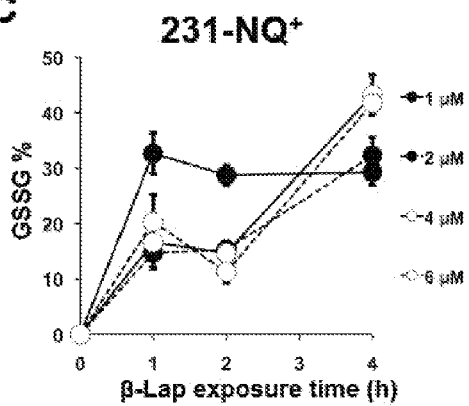
Figure 30:
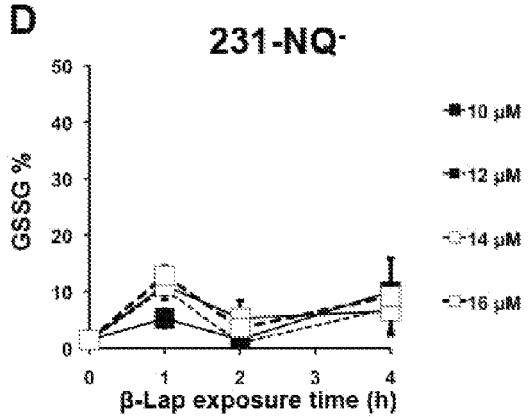

FIG. 30 depicts therapeutic doses of β-lap induce NQO1 dependent lethality that correlates with oxidative stress responses. In (a-b), 231-NQ+ and 231-NQ− cells were seeded in 48 well plates and exposed to varying doses of β-lap for 2 h. Fresh media was added after the 2 h drug pulse and long-term survival (DNA content analyses) were performed. In (c-d), 231-NQ+ and 231-NQ− cells were exposed to the indicated doses of 3-lap for varying times and glutathione levels were assessed. Student's t-test were performed in order to determine whether statistical differences existed between means of individual treatments from experiments performed in sextuplet (a-b) or triplicate (c-d) and repeated 3 times.

Figure 31:
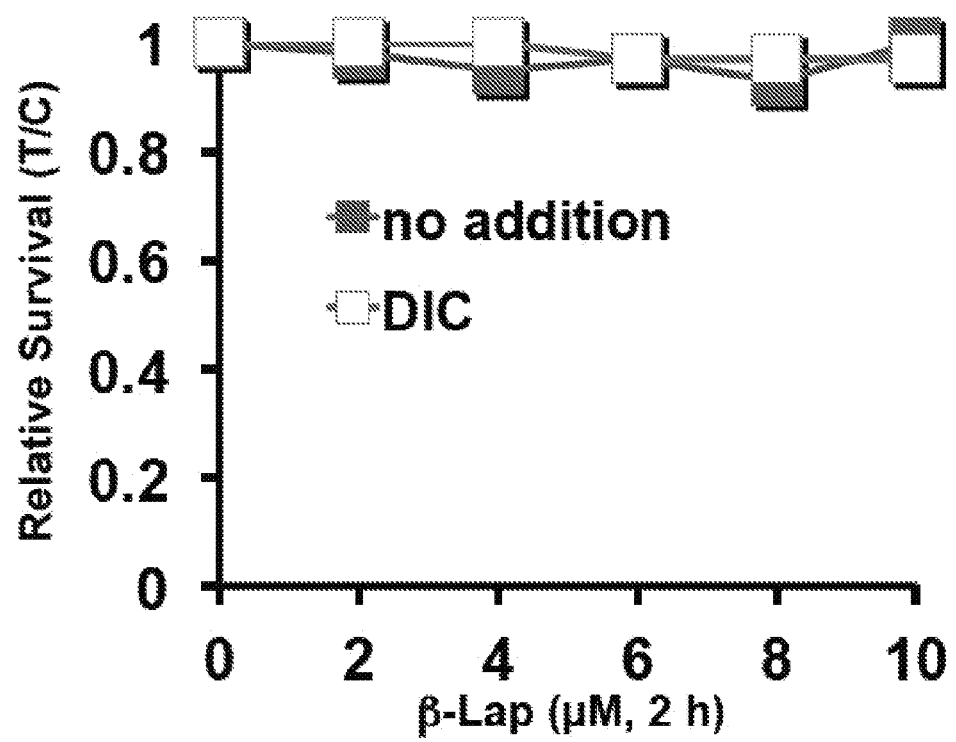

FIG. 31 depicts normal mammary epithelial cells are less responsive to β-lap toxicity. Normal human mammary epithelial cells (HMEC 1585) were seeded in 48 well dishes and treated with varying doses of β-lap for 2 h. Cells were then given fresh medium and control wells were allowed to become 80-90% confluent. Hoescht staining for DNA content was performed to determine relative survival.

Figure 32:
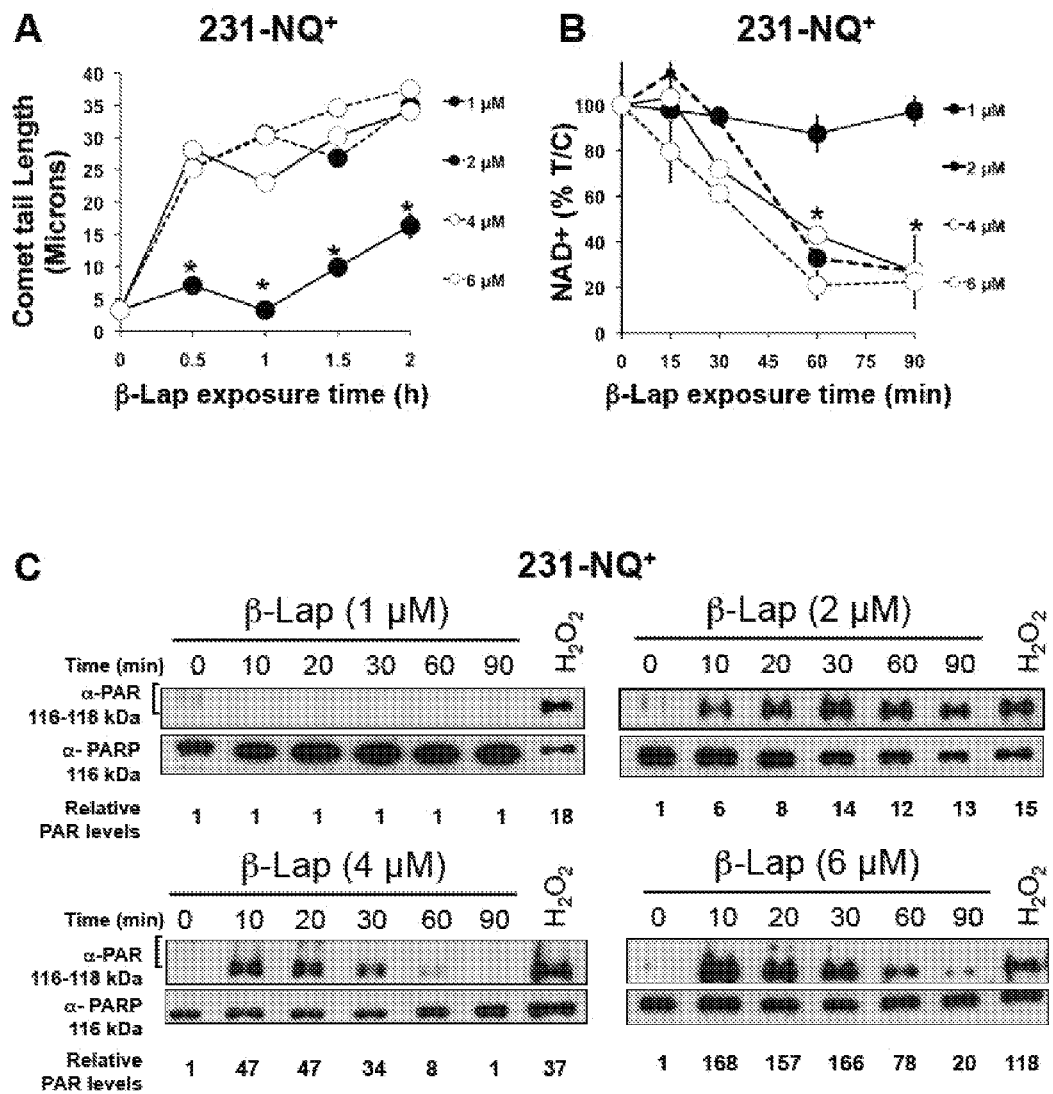

FIG. 32 depicts increasing β-lap dosage augments DNA repair/lethal-damage threshold responses resulting in NQO1 mediated nucleotide depletion and PARP1 hyperactivation. In (a), 231-NQ+ cells were treated with various doses of β-lap for the indicated times and comet tails were analyzed using ImageJ software. Data graphed are means±SE of 50 individually analyzed fluorescent micrographs/treatment group from three independent experiments, *$p \leq 0.01$ (to 6 μM β-lap). In (b), 231-NQ+ cells treated with various doses of β-lap (1, 2, 4, or 6 μM) for the indicated times. NAD+ content was measured. In (c), 231-NQ+ cells were treated with various doses of β-lap for the indicated times and analyzed for PAR formation (to monitor PARP1 hyperactivation) by Western blot analyses. The PAR protein monitored in these blots is the PAR-modified and inactivated form of PARP-1 producing 116-118 kDa bands. Shown are representative blots of experiments performed at least three times.

Figure 33:
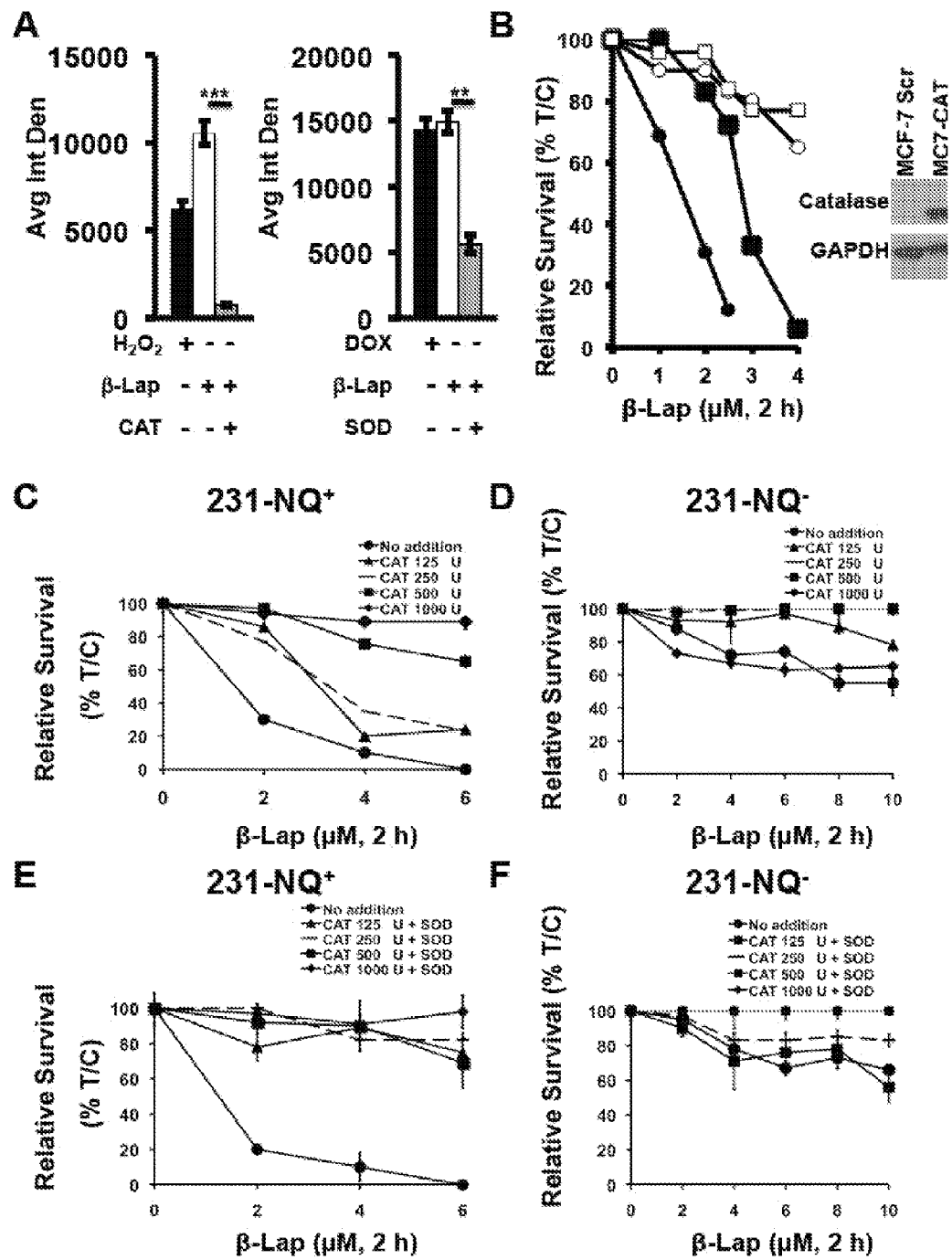

FIG. 33 depicts catalase inhibition of β-lap induced ROS formation and enhancement of long-term survival. In (a), 231-NQ+ cells were stained with DHE or DCFDA as described in "Materials and Methods". Following the staining procedure, cells were treated with 4 μM β-lap for 20 min in the absence or presence of 1000 U of catalase or 3000 U of SOD. Fluorescent photomicrographs of at least 50 cells (treated and untreated) were compared using NIH image J software to evaluate ROS levels (DHE predominantly detects ROS generated by superoxide and DCFDA detects $H_2O_2$ generated ROS). Shown is a representative graph from experiments performed a minimum of 3 times. In (b), MCF-7 cells were transiently transfected with a CMV-driven catalase expression vector or a control vector (Open Bio-systems). 48 hours following the transfection procedure, cells were trypsinized, counted and plated in 48 well dishes. After 24 h, cells were treated with varying doses of β-lap and cell growth assays were performed. DNA content was determined using Hoescht dye. In (c-d), 231 NQ+ (c) or 231 NQ− (d) cells were treated for 2 h with varying doses of β-lap in the absence or presence of varying doses of catalase. Following the 2 h treatment fresh media were added and cells were allowed to incubate until control wells were 80-90% confluent. DNA content was determined using Hoescht dye. Shown are representative graphs of experiments performed in sextuplicate and repeated 3 times. In (e-f) 231 NQ+ or 231 NQ-cells were treated for 2 h with varying doses of β-lap in the absence or presence of varying doses of catalase and 3000 U of SOD. Following the 2 h treatment fresh media was added and cells were analyzed as previously described in (c-d).

Figure 34:
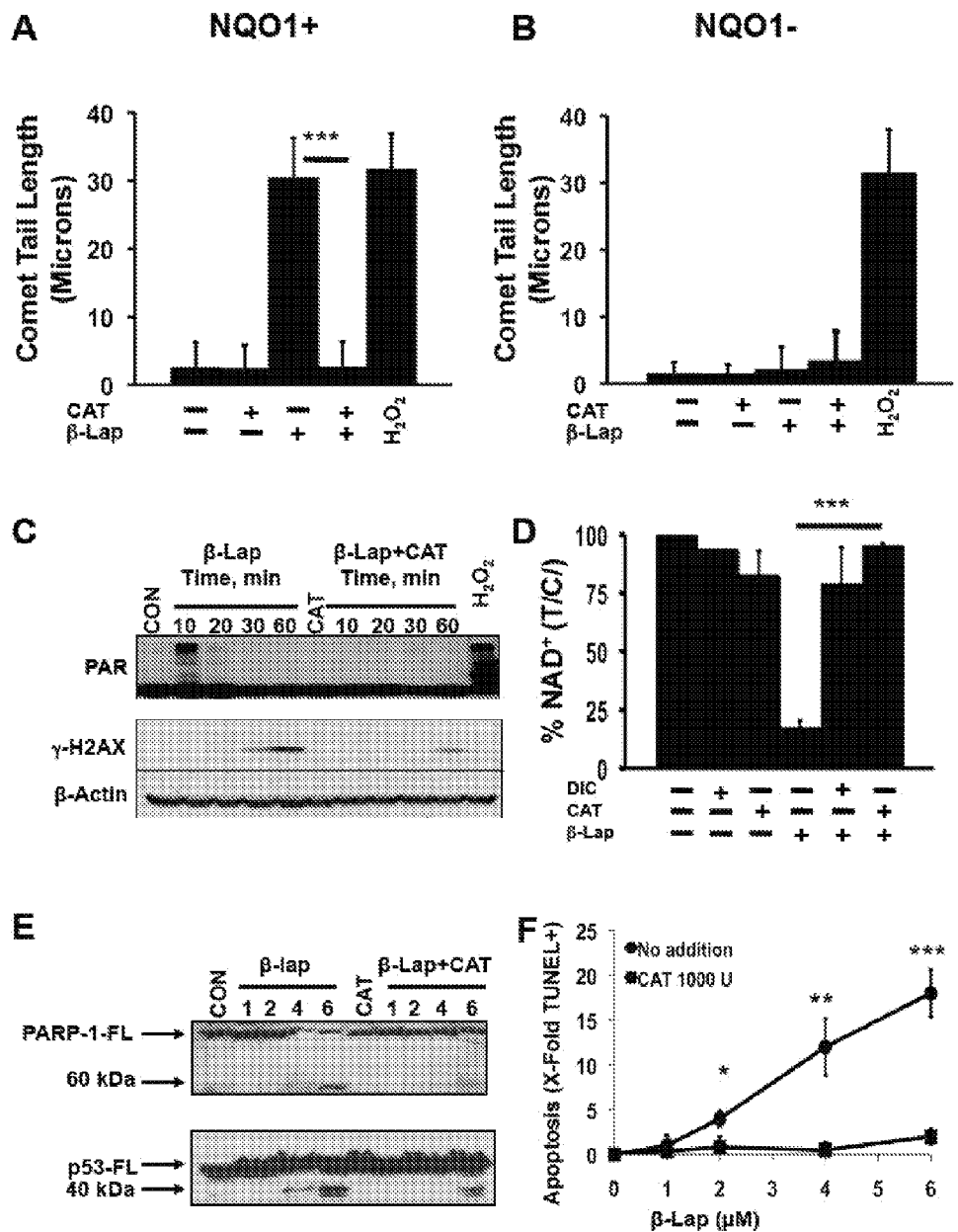

FIG. 34 depicts exogenous catalase addition abrogates β-lap-mediated cytotoxicity. In (a-b), 231 NQ+ or NQ− cells were treated with 4 μM β-lap for 2 h in the presence or absence of 1000 U of catalase 1000. Cells were then harvested analyzed for DNA damage by comet tail formation following alkaline electrophoresis. Shown is a representative graph of at least 50 comet tails per treated or untreated group. Student's t-tests were performed to determine whether significant differences existed between treatment groups. In (c), 231 NQ+ cells were treated with 4 μM β-lap for the times indicated in the absence (left panel) or presence (right panel) of 1000 U of catalase. Lysates were harvested and subjected to PAGE. Immobilized complexes were then transferred onto PVDF membranes and western-blots for PAR formed PARP1 and gamma-H2AX were performed. In (d), 231 NQ+ cells were treated with 4 μM β-lap for 2 h in the presence or absence of 1000 U of catalase or 50 M dicoumarol. Cells were then analyzed for NAD+ levels. Shown is a representative experiment performed in triplicate and repeated 3 times. In (e), 231 NQ+ cells were treated with varying doses of β-lap for 2 h in the absence (left panel) or presence (right panel) of 1000 U of catalase. Following the 2 h pulse fresh media were added and cells were harvested after 48 h. Lysates were harvested as described in (c) and western-blots for PARP1 and p53 were performed as described in "Materials and Methods". In (f), Left panel, 231-NQ+ cells were treated with various doses of β-lap (1, 2, 4 or 6 βM) for 2 h in the absence or presence of 1000 U of catalase and analyzed for TUNEL positivity 24 h later. Data were graphed as fold positivity of β-lap-treated over control DMSO-treated cells±SEM from three independent experiments. Right panel, MCF-7 cells were treated for 2 h with 4 μM β-lap in the absence or presence of 1000 U of catalase. After the 2 h drug pulse, fresh medium was added and cells were incubated for and additional 24 h. Cell lysates were analyzed for PARP1 and p53 cleavage using Western-blotting procedures.

Figure 35:
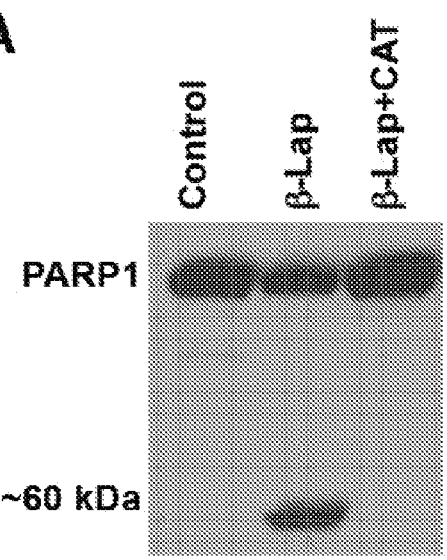
Figure 35:
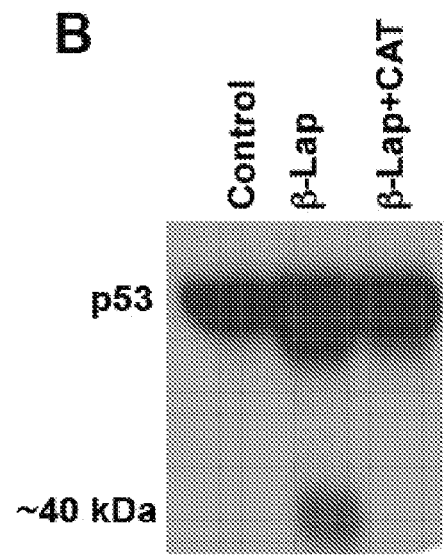

FIG. 35 depicts catalase prevention of β-lap-induced atypical PAPR1 proteolysis. In (a) and (b), MCF-7 cells were exposed to 4 μM for 2 h harvested and lysates were resolved in 10% SDS-PAGE gels. Immobilized proteins were probed with PARP1 (a) and p53 DO1 (b) antibodies.

Figure 36:
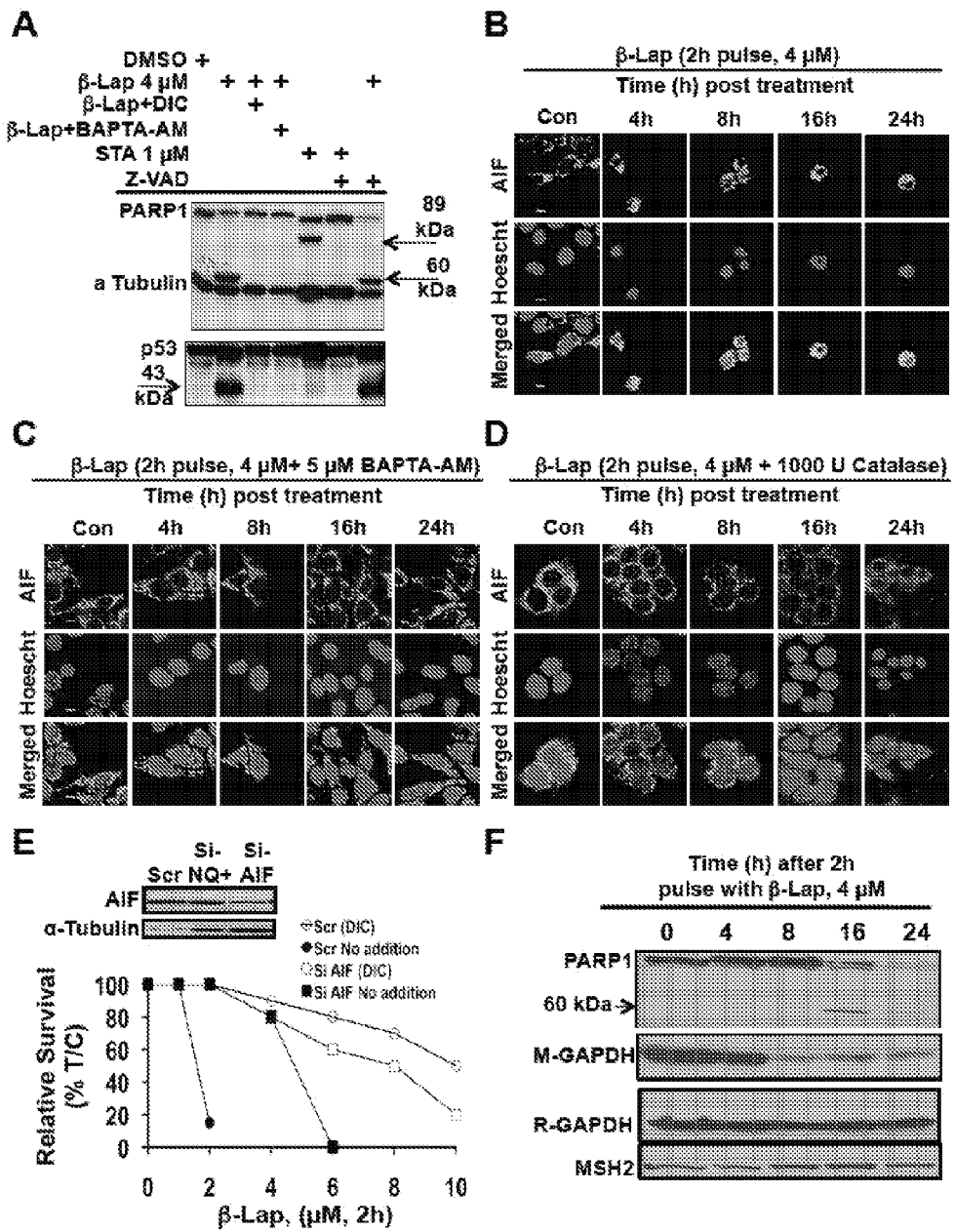

FIG. 36 depicts β-lap induced endonuclease activities are abrogated by exogenous catalase addition. In (a), MCF-7 cells were treated for 2 h with 4 μM β-lap in the absence or presence of varying inhibitors including: 50 μM dicoumarol or 5 μM BAPTA-AM. As a positive control for caspase mediated apoptosis, MCF-7 cells were treated with 1 M staurosporine (STA, 24 h) in the absence or presence of the pan-caspase inhibitor Z-VAD. Western-blot analyses for full length and cleaved forms of PARP1 and p53 were performed. In (b-d), MCF-7 cells were treated for varying times with 4 μM β-lap (b) or β-lap and 5 μM BAPTA-AM (c) or β-lap and 1000 U of catalase (d). Cells were harvested at the indicated times and stained with polyclonal antibody to AIF. Representative confocal micrographs were taken using Nikon C1 confocal microscope at 100× magnification. In (e) MCF-7 cells were transfected with 20 μM siRNA to AIF or with scrambled siRNA. After 48 h cells were trypsinized, counted and seeded in 48 well plates. Cells were then allowed to adhere overnight and then treated for 2 h with varying doses of β-lap with or with out dicoumarol. Cells not used for growth assays were pelleted and lysed. Lysates were analysed by western-blot analyses for AIF expression (inset). In (f), MCF-7 cells were treated with 4 μM β-lap for 2 h. After the drug pulse fresh media were added and cells were harvested at the indicated times. Cell extracts were subjected PAGE and western blot analyses were performed. Immunoblots were stained with antibodies to PARP1 and GAPDH. MSH2 staining was used as an internal loading control.

Figure 37:
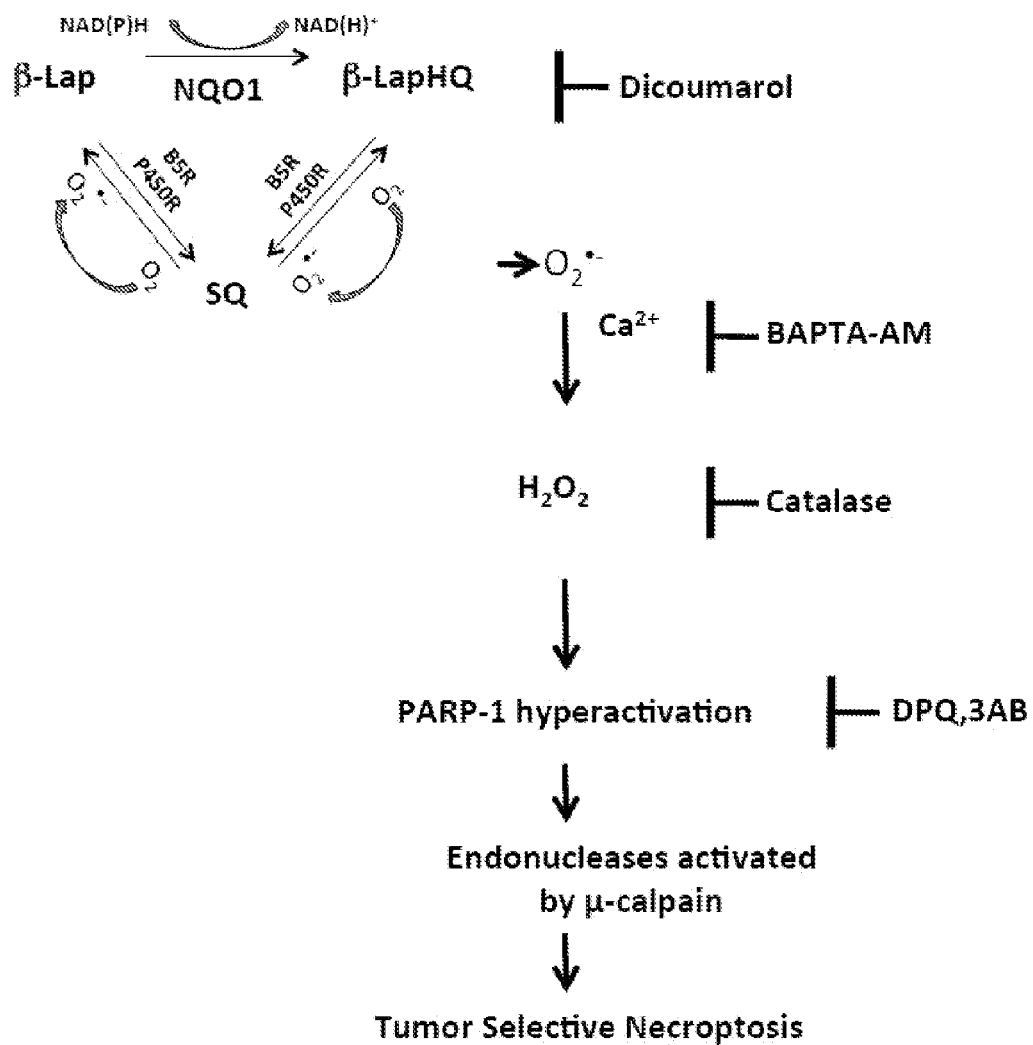

FIG. 37 depicts NQO1-directed futile cycling of β-lap induces an ROS/PARP1-mediated and tumor specific necroptotic pathway. Model depicting NQO1 mediated toxicity in NQO1 overexpressing tumor cells. Cellular uptake of the parent quinone (β-lap) by NQO1 overexpressing tumor cells culminates in formation of a hydroquinone mediated by NQO1. In the presence of molecular oxygen β-lap-hydroquinone (β-lapHQ) undergoes spontaneous and continuous cycling leading to a net loss of NAD(P)H, the electron donor for NQO1 enzyme activity. The utilization of essential NAD(P)H pools essentially hijacks the cells requisite energy equivalent supplies. This leads to catastrophic cellular events including NQO1-dependent oxidative stress, PARP1 hyperactivation, nucleotide depletion and finally tumor selective necroptotic lethality. The pathway is delineated by inhibitors of β-lap-mediated necroptosis including: dicourmarol (NQO1), catalase (ROS) and PARP1 inhibitors such as 3 amino benzamide (3AB).

Figure 38:
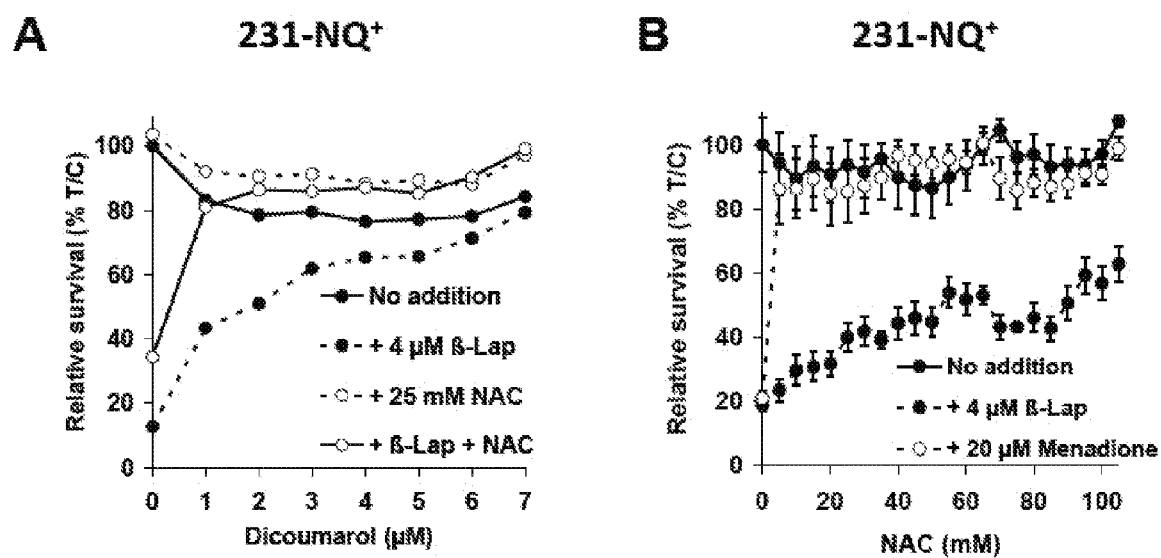

FIG. 38 depicts high dose NAC partially abrogates β-lap toxicity. In (a), NQO1+MDA-MB-231 cells were treated with medium containing increasing doses of dicoumarol either alone (solid symbols and lines) or coadministered with β-lap (4 μM, solid symbols and dashed lines), or NAC 25 mM, 1 h pretreatment followed by cotreatment, open symbols and dashed lines) or both (open symbols and solid lines). Medium was then removed, fresh medium added, and cells monitored for changes in relative survival. Relative DNA content was determined. In (b), NQO1+MDA-MB-231 cells were treated with: medium containing various NAC concentrations either alone (solid symbols and lines) or coadministered with β-lap (4 μM, solid symbols and dashed lines, or menadione (20 μM, open symbols dashed lines) for 2 h. Following the 2 h treatment, fresh medium was added and the relative survival of cells was monitored.

DETAILED DESCRIPTION OF THE INVENTION

Provided herein methods for 1) determining whether an individual with cancer is a suitable candidate for treatment with an NQO1 bioactivatable drug, 2) predicting the responsiveness of an individual with cancer to treatment with an NQO1 bioactivatable drug, and 3) treating an individual with cancer with an NQO1 bioactivatable drug composition. The inventors have observed that increased expression of NQO1 and decreased expression of catalase in tumors relative to the expression of these proteins in normal tissues (such as associated normal tissue) is associated with a greater likelihood of response to treatment with an NQO1 bioactivatable drug. NQO1 bioactivatable drugs display greater lethality when exposed to tumors and/or cancer cells having greater relative expression or enzymatic activity of NQO1 and less relative expression or enzymatic activity of catalase compared to tumors and/or cancer cells expressing decreased levels of NQO1 and increased levels of catalase relative to the normal tissue. This is useful for selecting individuals or subpopulations of individuals with cancer for appropriate treatment. This is also useful as part of a method of treating individuals with cancer, including tumor cells which have metastasized away from the location of the primary tumor, with an NQO1 bioactivatable drug.

As used herein, an "individual" is a mammal, more preferably a human. Mammals include, but are not limited to, humans, primates, farm animal, sport animals, rodents, and pets (e.g., dogs and cats).

As used herein and in the appended claims, the singular forms "a," "an," and "the" include plural reference unless the context clearly indicates otherwise.

Reference to "about" a value or parameter herein includes (and describes) embodiments that are directed to that value or parameter per se. For example, description referring to "about X" includes description of "X."

It is understood that aspect and variations of the invention described herein include "consisting" and/or "consisting essentially of" aspects and variations.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

General Techniques

The practice of the present invention will employ, unless otherwise indicated, conventional techniques of molecular biology, microbiology, cell biology, biochemistry, nucleic acid chemistry, and immunology, which are well known to those skilled in the art. Such techniques are explained fully in the literature, such as, *Molecular Cloning: A Laboratory Manual*, second edition (Sambrook et al., 1989) and *Molecular Cloning: A Laboratory Manual*, third edition (Sambrook and Russel, 2001), (jointly referred to herein as "Sambrook"); *Current Protocols in Molecular Biology* (F. M. Ausubel et al., eds., 1987, including supplements through 2001); *PCR: The Polymerase Chain Reaction*, (Mullis et al., eds., 1994); Harlow and Lane (1988) *Antibodies, A Laboratory Manual*, Cold Spring Harbor Publications, New York; Harlow and Lane (1999) *Using Antibodies: A Laboratory Manual* Cold Spring Harbor Laboratory Press, Cold Spring Harbor, N.Y. (jointly referred to herein as "Harlow and Lane"), Beaucage et al. eds., *Current Protocols in Nucleic Acid Chemistry* John Wiley & Sons, Inc., New York, 2000), *Handbook of Experimental Immunology*, 4th edition (D. M. Weir & C. C. Blackwell, eds., Blackwell Science Inc., 1987); and *Gene Transfer Vectors for Mammalian Cells* (J. M. Miller & M. P. Calos, eds., 1987).

Differential Expression of NQO1 and Catalase in Tumors

NAD(P)H dehydrogenase [quinone] 1 (NQO1) is an enzyme that in humans is encoded by the NQO1 gene. This gene is a member of the NAD(P)H dehydrogenase (quinone) family and encodes a cytoplasmic 2-electron reductase. This FAD-binding protein forms homodimers and reduces quinones to hydroquinones. This protein's enzymatic activity prevents the one electron reduction of quinones that results in the production of radical species. Exposure of NQO1 to an NQO1 bioactivatable drug is thought to result in damage to DNA in a manner that specifically hyperactivates poly (ADP-ribosyl) polymerase 1 (PARP1), thereby leading to the inhibition of DNA repair and inducing programmed necrosis. The synergy is independent of p53 status, cell cycle status, and immune to hypoxia and other resistance mechanisms.

NQO1 is differentially overexpressed in several human cancers (e.g., prostate, breast, nonsmall cell lung, pancreatic and colon cancers) over normal cells/tissue. In some embodiments, NQO1 is expressed in multiple tumor types at levels 5- to 200-fold greater than in associated normal tissue (see FIG. 22). Specifically, preliminary research has demonstrated up to 200-fold over-expression in over 80% of non-small cell lung cancer (NSCLC), up to 100-fold over-expression in over 80% of pancreatic cancer, up to 10-fold over-expression in 60% of prostate cancer, up to 10-fold over-expression in 60% of breast cancer, and up to 10-fold over-expression in 50% of colorectal cancer. In other embodiments, the level of NQO1 expression is determined by measuring the amount of NQO1 protein present within a sample. The sample can be a tumor sample or can be a sample of normal tissue. In some embodiments, NQO1 is expressed in tumor cells at a level at least about 5 fold, about 10 fold, about 15 fold, about 20 fold, about 25 fold, about 30 fold, about 35 fold, about 40 fold, about 45 fold, about 50 fold, about 55 fold, about 60 fold, about 65 fold, about 70 fold, about 75 fold, about 80 fold, about 85 fold, about 90 fold, about 95 fold, about 100 fold, about 105 fold, about 110 fold, about 120 fold, about 130 fold, about 140 fold, about 150 fold, about 160 fold, about 170 fold, about 180 fold, about 190 fold, or about 200 fold, inclusive, including any value in between these numbers, greater than the expression of NQO1 in normal tissue. In other embodiments, the level of NQO1 expression is determined by measuring the amount of NQO1 enzymatic activity present within a sample. In some embodiments, the NQO1 enzymatic activity in the cancer cells of an individual is greater than about 50, about 60, about 70, about 80, about 90, about 100, about 110, about 120, about 130, about 140, or about 150 units, inclusive, including any values in between these numbers. NQO1 enzyme activity is measured using a cytochrome-c reduction assay. In one non-limiting example, NQO1 enzymatic activity in cancer cell and associated normal tissue extracts is determined using NADH (200 mmol/L) as an immediate electron donor and menadione (10 mmol/L) as an intermediate electron acceptor as described by Pink et al., 2000, *J. Biol. Chem.* 275:5416-24; and Fitzsimmons et al., 1996, *J. Natl. Cancer Inst.* 88:259-69. See Example 11. Enzyme units (U) of NQO1 are calculated as nmol of cytochrome-c reduced/min/μg of protein from the cancer call extracts, based on initial rate of change in absorbance at 550 nm. As used herein, an "NQO1 enzymatic activity at a certain level" (such as ≥50 units) refers to the NQO1 enzymatic activity measured by the method described above and in Example 11 in detail. Although other methods may be used in measuring the NQO1 enzymatic activity, the activity measured can be converted to show it is equivalent to the level using the method described herein.

In multiple preclinical models, NQO1 bioactivatable drug-mediated cell death occurs specifically in tumor tissues over-expressing NQO1, while normal tissues and organs with low levels of this enzyme are spared. Across tumors, NQO1 bioactivatable drug-induced cancer cell death occurs in proportion to tumor NQO1 levels (see FIG. 16). Importantly, the absence of NQO1 in normal and tumor tissue samples occur with the same frequency and in the same patients (up to 15%), as known NQO1 genotypic polymorphisms (designated *2/*2, which corresponds to a C609T mutation, and *3/*3, which corresponds to a C465T mutation). Assays that enable one to distinguish wild-type (*1/*1) NQO1 from variants allows determination of candidates for NQO1 bioactivatable drug therapies.

Catalase is a common enzyme found in nearly all living organisms that are exposed to oxygen, where it catalyzes the decomposition of hydrogen peroxide to water and oxygen. Catalase has one of the highest turnover numbers of all enzymes; one catalase molecule can convert 40 million molecules of hydrogen peroxide to water and oxygen each second. Hydrogen peroxide is a harmful by-product of many normal metabolic processes; to prevent damage, it must be quickly converted into other, less dangerous substances. To this end, catalase is frequently used by cells to rapidly catalyze the decomposition of hydrogen peroxide into less reactive gaseous oxygen and water molecules.

Although NQO1 bioactivatable drug resistance has not been noted, factors associated with ROS detoxification, such as catalase expression, can reduce NQO1 bioactivatable drug efficacy and act as a detoxification process in sparing normal tissue (FIG. 23). The inventors have shown that, relative to healthy cells of normal tissue, NSCLC cells are deficient in catalase expression (see FIGS. 4 and 5), further enhancing the therapeutic window of NQO1 bioactivatable drug use against specific cancers that over-express NQO1 (for example, but not limited to, NSCLC, prostate, breast, pancreatic and colon). Accordingly, the ratio of NQO1 expression over catalase expression in cancer cells may be used for selecting individuals for treatment with an NQO1 bioactivatable drug. In some embodiments, the ratio of the NQO1 expression level over the catalase expression level in tumor cells from an individual is greater than any of about 50 fold, about 55 fold, about 60 fold, about 65 fold, about 70 fold, about 75 fold, about 80 fold, about 85 fold, about 90 fold, about 95 fold, about 100 fold, about 150 fold, or about 200 fold, inclusive, including any value in between these numbers, over the ratio of NQO1 to catalase expression level in normal tissue (such as, without limitation, tissue taken from a cancer-free area in an individual with cancer or tissue taken from a disease-free area of a cancer-containing tissue in an individual with cancer). In some embodiments, the level of NQO1 and catalase expression is determined by measuring the amount of NQO1 and catalase enzymatic activity present within a sample. In other embodiments, the level of NQO1 and catalase expression is determined by measuring the amount of NQO1 and catalase protein and/or mRNA present within a sample.

Measurement of NQO1 and Catalase

The ratio of NQO1 over catalase expression in tumors relative to the ratio in normal tissues can be used as biomarkers for determining whether an individual with cancer is suitable for treatment with an NQO1 bioactivatable drug by assessing the expression levels of NQO1 and catalase in a sample from an individual with cancer. The phrase "amounts of NQO1 and catalase expression" encompasses the conversion of the NQO1 and catalase DNA gene sequence into transcribed mRNA (including, e.g., the initial unspliced mRNA transcript or the mature processed mRNA), the translated NQO1 and catalase protein products (including, e.g. any posttranslational modifications such as, but not limited to, ubiquitination, sumoylation, acetylation, methylation, glycosylation, and/or hydroxylation), as well as the enzymatic activities of NQO1 and catalase (including, e.g., the reduction of quinones to hydroquinones and the conversion of hydrogen peroxide into water and oxygen gas, respectively). As used herein, the expression level can be an average value, a median value, a mean value, or a value as compared to a particular control or baseline value. The expression level may also be normalized using a reference value.

Obtaining Samples from Tumors and Normal Tissues

Samples from tumors and normal tissues (such as associated normal tissue) used for determination of NQO1 and catalase expression levels (including enzymatic activity) can be obtained in a variety of ways. The term "sample," as used herein, refers to a composition that is obtained or derived from a subject of interest that contains a cellular and/or other molecular entity that is to be characterized and/or identified, for example, based on physical, biochemical, chemical and/or physiological characteristics. In one embodiment, a sample from a tumor can be obtained from a subcutaneously accessible tumor or from any other type of cancerous solid tumor accessible to biopsy or surgical removal. The tumor sample can be obtained by any method known in the art including, but not limited to, needle biopsy, core biopsy, or fine needle aspiration. As for normal tissue samples, these may be taken from a cancer-free area in an individual with cancer, from a disease-free area of a cancer-containing tissue in an individual with cancer, from the tissue of an individual without cancer, or from peripheral blood mononuclear cells (PBMC). Furthermore, samples may be fixed, paraffin embedded, fresh, or frozen before expression levels and/or enzymatic activity of NQO1 and catalase are measured. In another embodiment, the cancer cell sample can be obtained from circulating cancer cells from the individual's circulatory or lymphatic system.

Similarly, a sample from an associated normal tissue can be obtained by any method known in the art. The determination of "normal" tissue and the percentage of tumor infiltration into that tissue is determined by a qualified pathologist. By "a sample from an associated normal tissue," it is meant a sample of cells, tissue, or fluid taken from a disease-free area of an individual with cancer or a disease free area of the cancer-containing tissue of an individual with cancer. The associated normal tissue sample may also include normal cells taken from an individual and kept in culture. The sample from an associated normal tissue may be fixed, paraffin embedded, fresh, or frozen before expression levels and/or enzymatic activity of NQO1 and catalase are measured. Fresh or adequately frozen tissue are required for enzymatic activities to be determined. Normal tissues may be confirmed by H&E staining and by pathology determination by standard measures.

Measurement of NQO1 and Catalase Expression Levels and Enzymatic Activity

The assessment of NQO1 and catalase expression can be at the levels of protein or mRNA. Assessment of mRNA expression levels of gene transcripts is routine and well known in the art. For example, one quantitative method for assessing mRNA expression levels in a biological sample is by quantitative RT-PCR (qRT-PCR) or by any other comparable quantitative PCR-based method. Additional methods for assessing NQO1 and catalase mRNA expression include, but are not limited to, Northern blotting, microarrays, in situ hybridization, and serial analysis of gene expression (SAGE).

NQO1 and catalase protein or mRNA expression levels can be measured from samples obtained from the tumors or normal tissue (such as associated normal tissue) of individuals with cancer and can be normalized to the expression levels of one or more reference genes expressed in the sample. Normalization, with regard to protein or mRNA expression, can be accomplished by measuring mRNA transcript levels or the protein product of interest relative to mean levels of transcripts/products of one or more reference genes, wherein the reference genes are either selected based on their minimal variation across individuals, tissues, or treatments or are the totality of tested genes. With the latter case, frequently referred to as "global normalization," the total number of tested genes must be relatively large, if possible greater than 50. Specifically, the term "normalized" with respect to a particular mRNA transcript can refer to the transcript expression level relative to the mean of transcript levels of one or more reference, or "housekeeping," genes. Suitable housekeeping genes are ideally expressed at a constant level among different tissues and are unaffected by treatment or disease state. Messenger RNAs (mRNAs) commonly used as housekeeping genes include, but are not limited to, ubiquitin (Ub), glyceraldehyde-3-phosphate-dehydrogenase (GAPDH), and the cytoskeletal protein 3-actin.

Cancer cells often exhibit increased chromosomal rearrangements and translocations as well as gene mutations within neoplastic cells. NQO1 is known to exhibit specific genotypic polymorphisms (designated *2/*2, which corresponds to a C609T mutation, and *3/*3, which corresponds to a C465T mutation) at a constant rate throughout the population. Assays that enable one to distinguish wild-type (*1/*1) NQO1 from the *2/*2 and *3/*3 polymorphic variants in a population or subpopulation of cells are routine in the art. For example, one method for detecting whether the NQO1 gene sequence in an individual's genomic DNA has been mutated during the course of carcinogenesis is Southern blotting, which combines transfer of electrophoresis-separated DNA fragments to a filter membrane and subsequent fragment detection by probe hybridization. Another method is PCR of one or more segments of the NQO1 gene followed by either restriction digestion or DNA sequencing by any method known in the art.

Assessment of protein expression levels is also routine in the art. For example, one method of measuring protein levels is via Western blotting or immunohistochemistry using antibodies to NQO1 and/or catalase. Without being bound to theory, there is a direct correlation between the expression level of the NQO1 protein and the likelihood that an individual will be responsive to treatment with an NQO1 bioactivatable drug. Also, without being bound to theory, there is direct correlation between the ratio of the level of NQO1 protein expression over the level of catalase protein expression and the likelihood of responsiveness to treatment with an NQO1 bioactivatable drug. Consequently, the sensitivity of the protein assay is particularly important. Therefore, radioimmunoassay (RIA), enzyme-linked immunosorbent assay (ELISA), flow cytometry, or any other more sensitive quantitative method of measuring NQO1 and catalase protein expression can be used instead of less quantitative methods.

In some aspects, the expression level of NQO1 is determined by an enzyme activity assay. The protein level of NQO1 in tumor cells and associated normal tissue can be measured by the enzymatic activity present in the cells. The enzyme activity of NQO1 can be measured using any methods known in the art, such as direct enzyme assay using fresh or frozen tumor tissue. NQO1 enzyme activity can also be measured using a cytochrome-c reduction assay. In one non-limiting example, NQO1 enzymatic activity in cancer cell and associated normal tissue extracts is determined using NADH (200 mmol/L) as an immediate electron donor and menadione (10 mmol/L) as an intermediate electron acceptor as described by Pink et al., 2000, *J. Biol. Chem.* 275:5416-24; and Fitzsimmons et al., 1996, *J. Natl. Cancer Inst.* 88:259-69. Enzyme units (U) of NQO1 are calculated as nmol of cytochrome-c reduced/min/µg of protein from the cancer call extracts, based on initial rate of change in absorbance at 550 nm. As used herein, an "NQO1 enzymatic activity at a certain level" (such as ≥50 units) refers to the NQO1 enzymatic activity measured by the method described above and in Example 11 in detail. Although other methods (including using different substrate) may be used in measuring the NQO1 enzymatic activity, the activity measured can be converted to show it is equivalent to the level using the method described herein.

In some aspects, the expression level of catalase is determined by an enzyme activity assay. The protein level of catalase in cancer cells and associated normal tissue can be measured by the enzymatic activity present in the cells. The enzyme activity of catalase can be measured using any methods known in the art, such as direct enzyme assay using fresh or frozen tumor tissue. Catalase enzyme activity can also be measured using a hydrogen peroxide reduction assay. In one non-limiting example, catalase enzymatic activity in cancer cells and associated normal tissue extracts can be determined by measuring the decrease in absorbance at $A_{240nm}$ of a standard hydrogen peroxide solution. In this assay, one enzymatic unit (U) of catalase will decompose 1.0 µmole of $H_2O_2$ per minute at pH 7.0 at 25° C., while the $H_2O_2$ concentration falls from 10.3 mM to 9.2 mM. The rate of disappearance of $H_2O_2$ is followed by observing the rate of decrease in the absorbance at 240 nm (Beers & Sizer, 1952, *Journal of Biological Chemistry* 195, 133-140).

In some embodiment, the ratio of the NQO1 expression level over the catalase expression level in the cancer cells is compared to the ratio of the NQO1 expression level over the catalase expression level in the normal tissue (such as associated normal tissue). In some embodiments, the same assay method is used for measuring the expression level of NQO1 in the cancer cells and in the normal tissue. In some embodiments, the same assay method is used for measuring the expression level of catalase in the cancer cells and in the normal tissue. In some embodiments, NQO1 and catalase enzymatic activities are measured in the cancer cells and in the normal tissue as described herein.

Screening Protocols for Pre-Selection of Individuals for NQO1 Bioactivatable Drug Treatment Disclosed herein are practical screening protocols for the pre-selection of patients that should respond or not respond (e.g., based on NQO1 polymorphism expression or to a low NQO1/Catalase ratio) to NQO1 bioactivatable drugs. Further disclosed herein are assays that evaluate specific biomarker changes in conjunction with pharmacokinetic and pharmacodynamic assessments (FIG. 27) to reveal antitumor or normal tissue cytotoxicities for the evaluation of NQO1 bioactivatable drugs during therapies.

Assay 1

Disclosed herein, in certain embodiments, are prognostic and diagnostic biomarker assessment methods for the evaluation of patients that are predicted to respond to NAD(P)H:quinone oxidoreductase 1 (NQO1) "bioactive" drugs, from those patients in which such therapies are counter-indicated.

In some embodiments, the method comprises selecting a patient for treatment with a NQO1 bioactivatable drugs if the patient's tumor cells have a high level of NQO1 expression. In some embodiments, a patient expresses a high level of NQO1 if the level of NQO1 is 5-200× over normal tissue expression levels.

Tumor and normal tissue from patients are analyzed for NQO1 activity. For activity assays, S9 extracts are prepared by homogenizing tissue (by dounce homogenization or sonication on ice) in phosphate buffer saline (PBS, pH: 7.4) in the presence of a protease inhibitor cocktail. Homogenized extracts are then centrifuged at >10,000×g for 20 mins at 4° C. The resulting supernatants (S9 fraction) are used to determine NQO1 activity using a cytochrome-C reduction assay. Patients with NQO1 levels>50 units would be predicted to respond to NQO1 bioactivatable drug therapies, such as β-lapachone.

For example, In FIG. 16A the inventors demonstrate that NQO1 enzymatic levels correlate well with $LD_{50}$ values after β-lapachone treatment. Tumor cell lines with NQO1 enzyme activities≥50 units (for example, H441 and A549 cells) have $LD_{50}$ values of 1.5 and 2.5 μM respectively. In contrast, tumor cell lines with low (<50 enzymatic units) or no NQO1 enzyme activities (e.g., H2882 and H596 tumor cell lines) have $LD_{50}$ values>20 and would not be indicated for efficacious therapy using NQO1 bioactivatable drug therapies. Patients with elevated NQO1 levels would be predicted to respond to NQO1 bioactivatable drug therapies as demonstrated in long-term orthotopic lung tumor survival studies (animal model with human A549-lung tumor implants) shown in FIG. 16B.

Assay 2

Disclosed herein, in certain embodiments, are methods using simple blood PBMCs or tumor samples for identifying patients/cancers that have NQO1 gene polymorphisms (a C609T mutation (*2) or a C465T mutation (*3)) that result in low/no expression of NQO1. However, as demonstrated below in Example 12, cancers with C465T mutations at both alleles (*3/*3) are still responsive to treatment with NQO1 bioactivated drugs. Therefore, therapy for individuals having a (*2/*2) genotype using NQO1 bioactivated drugs would be counter-indicated. NQO1 levels in PBMCs and tumor tissues are validated.

DNAs are extracted from patient tumor and normal tissue when available using standard phenol:chloroform and ethanol precipitation methods. Alternatively, DNAs are isolated from circulating PBMCs or CTCs using a Genelute Bood Genomic DNA kit (Sigma cat#NA 2000). PCR reactions using patient DNAs are carried out using primers that detect *2 and *3 polymorphisms, as well as using controls for NQO1 polymorphism statuses. Specifically, forward 5'-gag-acg-cta-gct-ctg-aac-tga t-3' and reverse 5'-ctg cct gga agt tta ggt ca-3' primers for detecting *2 mutations are used. For *3 mutations, forward 5'-gct tta ctc gga ccc act c-3' and reverse 5'-gaa-gct-cca-tct-caa-aca-aac-3' primers are used. Additional amplification of PCR products (nesting PCR) are performed when needed using forward 5'-tct agt gtg cct gag gcc tcc-3' and reverse 5'-att-tga-att-cgg-gcg-tct-gct-g-3' primers for *2 mutations. Finally, additional amplification for *3 mutations are accomplished using forward 5'-tca agt tgg ctg acc aag gac a-3' and reverse 5'-cct-gca-tca-gta-cag-aac-ac primers. PCR products are then digested with Hinf1 or Msp1 to detect *2 and *3 mutations respectively (FIG. 17). Undigested (U) PCR products are run as controls. Undigested (U, uncut) and Digested (C) PCR DNA products are then separated by electrophoresis in 1% agarose gels and visualized by ethidium bromide staining.

For example, in FIG. 17, the inventors demonstrate that PCR analysis of patient DNA isolated from tumor samples can predict NQO1 polymorphism status. Specific primers are used to amplify regions within the DNA sequence where NQO1 polymorphism would arise. The amplified regions are then digested with restriction enzymes Hinf1 that cuts the DNA when a mutation site exist (C609T, *2) or leaves DNA uncut because a mutation exist (C465T, *3). The digested DNA are electrophoresed in 1% agarose gels and the DNA fragments are visualized and compared to undigested DNA by capturing a digital image of an ethidium bromide-stained gel. The resulting banding pattern as shown in FIG. 17 predicts NQO1 status compared to known controls, such as A549 (wild type, WT *1/*1), H596 (*2/*2) and H2009 (*3/*3) cell line samples. Those patients whose NQO1 statuses are determined to be heterozygous or wild-type for NQO1 would be indicated for NQO1-directed therapies and commonly demonstrate NQO1 over-expression in NSCLC, prostate, breast, pancreatic and colon cancers. The arrows, in FIG. 17 (upper gel, 609 for H596 cell control), indicate migration of DNA after Hinf1 restriction digest, strongly suggesting that *2 alleles are present. The arrow in FIG. 17 (lower gel, 465 for 2009 cell control), indicate migration of DNA that does not have a restriction site for Msp1 and remains uncut as does the undigested control band, which is indicative of DNA with *3 mutation alleles. Patients with *2 mutations should be counter-indicated for therapy using NQO1 bioactivatable drugs.

Assay 3

Disclosed herein, in certain embodiments, are methods for identifying patients/cancers who have a low ratio of NQO1:Catalase activity expression in tumor tissue, making them relatively resistant to NQO1 bioactivatable substrate drugs (e.g., β-Lap, streptonigrin, DNQ). NQO1:catalase ratio expression in PBMCs and circulating tumor cells (CTCs) will also be examined.

Tumor tissue (fresh tissue preferred, formalin fixed usable) biopsies from patients prior to treatment are processed by centrifugation into S9 fractions. For formalin-fixed tissue, immunohistochemistry (IHC) of NQO1 and catalase levels are performed. Cytosolic expression of each protein are quantified by relative staining intensity using β-actin or GAPDH loading controls and the ratios of NQO1:Catalase expression is correlated. Studies in the inventors' lab have found a linear correlation between IHC staining and enzymatic activities for each of these redox enzymes. NQO1 and catalase assays are then assessed and the ratio of NQO1:catalase units calculated as predictor of responsiveness to NQO1 bioactivatable drugs. The higher the ratio, the greater the predicted response to this class of drugs. For example, NSCLC tissue are devoid of catalase, yet have dramatically elevated levels of NQO1 (see below, FIG. 18), which are predicted to be extremely responsive to NQO1 bioactivatable drugs. In contrast, associated normal lung tissue has low levels of NQO1 and elevated levels of catalase that would translate into a low ratio of NQO1:Catalase expression and non-responsiveness to NQO1 bioactivatable drugs.

Simultaneously, blood samples (2 ml assessments before and after treatment with NQO1 bioactivatable drugs) are processed for isolation of PBMCs and CTCs. One microgram (1 μg) of material is then used to assess NQO1 and catalase levels in these samples before and after drug treatment (see below). The ratio of NQO1:Catalase will again predict responses in tumors (CTCs) that will correlate with tumor stem cell responses and bulk tumors, as well as non-responses or toxicity in normal lymphocytes and possibly normal tissue.

For example, in FIG. 18, the inventors demonstrate catalase and NQO1 protein levels in normal versus tumor tissues from a series of NSCLC patient samples. Samples from NSCLC cells, H596 and A549 are used as NQO1-deficient (NQO1−) and NQO1-overexpressing (NQO1+) controls, respectively, and are non-responsive and responsive cells to NQO1 bioactivatable drugs. Estimated NQO1:Catalase ratios from Western blotting (FIG. 18) and enzyme assays (FIG. 23, below) were 400, 325, 559, and 395 for NSCLC tumor tissues from de-identified patients 935, 3195, 1503 and 3672, respectively. In contrast, normal tissue NQO1:Catalase ratios were significant lower 0.023, 0.003, 0.03, and 0.001 for patients 400, 325, 559, and 395, respectively. The higher the ratio, the more response to NQO1 bioactivatable drugs are anticipated. In contrast, the lower the ratio the lower the expected response (e.g., toxicity) in normal tissue. Assessments of NQO1:Catalase ratios can be made from Western blots, IHC of fixed tissue, or direct enzyme assessments using fresh tissue as described above.

Assay 4

Disclosed herein, in certain embodiments, are methods for identifying patients/cancers that have low levels of catalase levels in tumor tissue—a deficiency in catalase enhances the activity of NQO1 bioactivated substrate drugs (e.g., β-lap, streptonigrin). Expression of catalase in normal peripheral blood mononuclear cells (PBMCs) (surrogate) will be directly related to drug toxicity, allowing therapeutic window determination.

Methodology similar to that described in Assay 3 are used to identify patients with tumor tissues that have low ratios of NQO1:catalase activities. In this instance, if normal tissue still demonstrates low ratios of NQO1:Catalase activities compared to tumor tissue, antitumor responses are still expected, but relatively higher levels of NQO1 bioactivatable drugs will be expected for equivalent antitumor activity. Or, combination therapies with agents such as standard of care X-irradiation or chemotherapies would be indicated. Thus using the NQO1:Catalase ratio, treatment dose-escalations, and or co-addition of ionizing radiation or other standard of care chemotherapies can be administered to these patients.

For example, Patient #2823 in FIG. 19 appears to have low levels of NQO1, with low but visible levels of Catalase. In fact, the ratio of NQO1:Catalase by enzymatic assessments is 3.0. Importantly, the ratio of NQO1:Catalase in associated normal tissue remains low at 0.02, 150 times lower that tumor tissue. In this case, although tumor NQO1 levels are significantly lower than in other NSCLC tumor tissues from other patients, they are still within the 50 units required for futile cycling of NQO1 bioactivatable drugs, such as 1-lap (FIG. 19). This patient would further benefit from prior exposure to standard of care chemotherapeutic or X-irradiation treatments that damage DNA. Thus, although the Western assessment of this patient may not indicate a potential benefit from therapy with NQO1 bioactivatable drugs, calculation of NQO1:Catalase ratios from tumor compared to normal tissues and validating these using the overview of this protocol described in this Invention now clearly indicates a benefit to the patient using NQO1 bioactivatable drugs alone, as well as in combination with radio- and/or chemotherapies commonly used for this disease (NSCLC in this case). Importantly, this methodology should also reveal patients that have overall NQO1 activities of less than 50 units and these patients would not benefit from NQO1 bioactivatable drug therapy alone. They could, however, still benefit from combination therapies with X-irradiation and/or chemotherapies, since much less NQO1 levels are required to hyperactivate PARP-1 and the low NQO1:Catalase ratios in normal tissue would dramatically spare normal tissue responses and therefore long-term toxicity complications.

Assay 5

Disclosed herein, in certain embodiments, are methods for determining the expression of specific signature factors that predict tumor responsiveness to NQO1 bioactivatable drugs. NQO1:catalase activity ratios in serum, red blood cells (RBCs), and peripheral blood mononuclear cells (PBMCs) are monitored for risk for NQO1 bioactivatable drug-mediated cytotoxicity to PBMCs and rbc hemolysis, which has been a rate limiting determinant in at least one NQO1 bioactivatable drug formulation. Tumor levels of signature proteins, NQO1, catalase (see above), AIF, PARP-1 and µ-calpain, are determined to predict responses to NQO1 bioactivatable drugs. The factors identified above are those that can be specifically used for predicting responses to NQO1 bioactivatable drugs.

Tumor and blood samples before NQO1 bioactivatable drug treatments are isolated and samples de-identified so that patient identification can no longer be established aside from the Principle Investigator (PI) of the study. From the blood, PBMCs, CTCs and RBCs are isolated and analyzed for NQO1:Catalase levels as described above. Ratios in PBMCs and RBCs are used to predict normal tissue toxicity. Ratios from CTCs, which contain cancer stem-like cells, are expected to be three orders of magnitude higher than PBMCs or RBCs and can be monitored as a surrogate of responses or predictor of responses (before therapy) for anti-tumor tissue responses, which are validated below (assay 6).

Tumor samples (all assays can be performed using 2-10 g material), biopsied when available before the start of therapy, are assessed for expression of specific protein factors, including levels of: (i) NQO1 and catalase; (ii) small and large µ-calpain subunit levels; (iii) AIF; and (iv) PARP-1. Expression of each of these factors is mandatory for tumor tissue programmed necrotic responses to NQO1 bioactivatable drugs and are unique to this class of antitumor agents. Specific examples of before and after therapy analyses of these factors are described below in assay 6.

Assay 6

Disclosed herein, in certain embodiments, are methods that include determining changes in tissue expression of NQO1 (see above) catalase, apoptosis inducing factor (AIF), µ-calpain and PARP1 levels as a means of identifying patients/cancers that respond to NQO1 bioactivated substrate drugs (e.g., β-lap, streptonigrin). Antitumor versus normal tissue responses are assessed in biopsied tissue by analyzing NAD+/ATP depletion, proteolyses of the large and small subunits of µ-calpain, and specific p53 and atypical PARP1 proteolytic events to determine if patients/cancers are responding to NQO1 bioactivated substrate drugs (e.g., β-lap, streptonigrin and all quinone drugs in which reduction by NQO1 does not lead to a stable product, which spontaneously converts to its parental quinone and in the process uses oxygen). Tissue responses are correlated with drug pharmacokinetics (PKs) and NQO1 pharmacodynamic (PD) futile cycle responses measured by formation of NAD+ levels during early times of drug treatment in CTCs.

Tumor samples (all assays can be performed using 2-10 g material), biopsied over time before and during therapies when available, are assessed for expression and changes in a variety of protein and metabolic factor expression, including levels of: (i) phosphorylated H2AX ($\square$H2AX) and phospho-serine$^{1981}$ ATM; (ii) formation of modified poly-ADP-ribosylated (PAR)-poly(ADP-ribose) polymerase-1

(PAR-PARP1) (iii) NAD+/ATP losses due to PARP1 hyperactivation; (iv) changes in expression of NQO1 (known to be damage-inducible) and catalase; (v) total (inactive) and proteolytic cleavage (active) of small and large μ-calpain subunits; and (vi) proteolytic cleavage of p53 and PARP-1 as a monitor of tumor cell death responses as a function of exposure and response to NQO1 bioactivatable drugs. When applicable, tumor responses to NQO1 bioactivatable drugs using these protein and metabolic factor changes are correlated with apoptotic indices monitored from fixed or fresh tumor tissue. Apoptotic responses are monitored using TUNEL reactions or using activated μ-calpain. Activated caspases are not typically noted during NQO1-directed, hyperactivated PARP-1-mediated programmed necrotic responses due to NQO1 bioactivatable drug exposures.

For example, specific proteolytic responses to NQO1 bioactivatable drugs, such as β-lapachone, have been monitored in vitro (shown) and in vivo in orthotopic and xenograft human 231 triple-negative breast cancer tissue (FIG. 21). Expression of specific proteins (i.e., changes in factors i-iv, above) are examined during therapies to monitor prognostic and diagnostic responses to NQO1 bioactivatable drugs. Furthermore, specific proteolytic responses in tumor tissue and CTCs in μ-calpain, p53 and PARP1 (factors v and vi, above) are diagnostic changes observed in programmed necrosis. NQO1 bioactivatable drugs are the only drugs known to cause these distinctive proteolytic responses in tumor tissue.

NQO1 Bioactivatable Drugs

Disclosed herein, in certain embodiments, are methods of using NQO1 bioactivatable drugs for cancer therapy. In some embodiments, the NQO1 bioactivatable drug is a β-lapachone (β-lap) compound or a pharmaceutically acceptable salt thereof. In some aspects, whether an individual with cancer is a suitable candidate for treatment with an NQO1 bioactivatable drug (such as a β-lap compound) is determined by the amount of NQO1 enzymatic activity or the ratio of the level of NQO1 protein expression over catalase protein expression in tumor cells versus the ratio of the expression of these proteins in associated normal tissue as determined by the methods described above. In other aspects, whether an individual is likely to respond to treatment with an NQO1 bioactivatable drug (such as a β-lap compound) is determined by the amount of NQO1 enzymatic activity or the ratio of the level of NQO1 protein expression over catalase protein expression in tumor cells versus the ratio of the expression of these proteins in associated normal tissue as determined by the methods described above.

NQO1 bioactivatable drugs (e.g., β-lapachone, DNQ, and streptonigrin and their derivatives) are metabolized by NQO1 in a futile manner to generate a series of cytotoxic factors, such as reactive oxygen species (ROSs) or quinone-based drug metabolites that cause damage to DNA, typically by alkylation. The term "futile manner" means that the two-electron oxidoreductase, NQO1, uses NAD(P)H to reduce these specific compounds, but that their hydroquinone forms are unstable and spontaneously revert to their parental structures; for example, for each mole of β-lap, >60 moles of NAD(P)H are used in 5 min showing that NQO1 'bioactivates' the drugs into cytotoxic reagents. In some embodiments, the NQO1 bioactivatable drug is a prodrug. In other embodiments, the NQO1 bioactivatable drug is formulated with cyclodextrins or with micelles (such as, but not limited to, SPIO-micessles or ligands encoded (e.g., $\alpha_v\beta_3$) micelles.

Beta-lapachone β-lap) is a potent cytotoxic anticancer agent with antitumor activity against a variety of human cancer cells, including drug resistance cell lines. β-lap is bioactivated by the intracellular enzyme NQO1. NQO1 is differentially overexpressed in several of human cancers over normal cells. At optimal concentrations and duration of exposure to cells, β-lap causes DNA damage, inhibits DNA repair and induces programmed cell death. β-Lap was initially thought to work as a DNA repair inhibitor. Previous reports have proposed that β-lap acts to inhibit topoisomerase 1 (Topo I), cell cycle checkpoint activation, and NF-kappa-B. New findings have shown a novel mechanism of action of β-lap. In some embodiments, β-Lap is bioactivated by the intracellular enzyme, NAD(P)H: quinone oxidoreductase 1 (NQO1).

With respect to β-lap, the reaction consumes two moles of oxygen for each β-lap mole used in the above reaction and this creates reactive oxygen species (ROS), which results in (a) the creation of large levels of SSBs in the nucleus; and (b) initiates release of calcium ($Ca^{2+}$) from the ER through lipid peroxidation. Thus, a small amount of β-lap creates large levels of DNA damaging ROS. β-Lap thereby serves to magnify the effects of radiation of other DNA damaging agents such as chemotherapy in a tumor-selective manner.

The excessive DNA damage caused by β-lap-induced, NQO1-driven ROS triggers the hyperactivation of PARP1. While active PARP1 in small quantities serves to repair DNA, at larger levels of activation PARP1 (or hyperactivation), its actions prevent DNA repair. The inventors' laboratory discovered that calcium ($Ca^{2+}$) was required for PARP1 hyperactivation, which consumes cell energy (NAD+/ATP). The loss of cell energy causes cell death through a unique programmed necrotic pathway. These data demonstrate that such NQO1 'bioactivatable' drugs induce a $Ca^{2+}$-dependent, PARP1 hyperactivation-induced programmed necrotic pathway in specific types of tumors (e.g., nonsmall cell lung, breast, prostate and pancreatic cancers) that express 5- to 200-fold higher levels of NQO1 enzymatic activity over those of associated normal tissue.

In some embodiments, the β-lapachone compound is β-lapachone, as shown in Formula I:

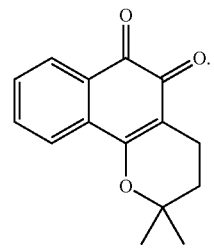 [SMILES: CC1(C)CCC2=C(O1)c1ccccc1C(=O)C2=O]

The β-lapachone compound described herein also includes analogs and derivatives of β-lapachone having similar anti-cancer activity as β-lapachone. In some embodiments, the β-lapachone compound is a prodrug of β-lapachone. In some embodiments, the β-lapachone compound is a polymer conjugated with a pH-sensitive prodrug of beta-lapachone, wherein the compound is capable of forming a micelle, for example, as described in as described in International Patent Application No. PCT/US2011/047497, the contents of which are hereby incorporated by reference in its entirety.

In some embodiments, the β-lapachone compound is a β-lapachone derivative. In some embodiments the β-lapachone derivative is a compound of Formula II:

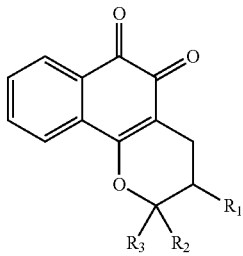

wherein $R_1$ is H, hydroxyl, substituted or unsubstituted alkyl, substituted or unsubstituted alkenyl, substituted or unsubstituted alkoxy, substituted or unsubstituted alkoxycarbonyl, —$(CH_2)_n$-amino, —$(CH_2)_n$-aryl, —$(CH_2)_n$-heteroaryl, —$(CH_2)_n$-heterocycle, — or —$(CH_2)_n$-phenyl, wherein n is an integer from 0 to 10; and $R_2$ and $R_3$ are each independently H, substituted or unsubstituted alkyl, substituted or unsubstituted alkenyl, substituted or unsubstituted alkoxy, substituted or unsubstituted alkoxycarbonyl, —$(CH_2)_n$-aryl, —$(CH_2)_n$-heteroaryl, —$(CH_2)_n$-cycloalkyl, $(CH_2)_n$-heterocycloalkyl, hydroxyl, substituted or unsubstituted thiol, halogen, nitro or cyano, for example, as described in U.S. Pat. No. 6,875,745, the contents of which are hereby incorporated by reference herein in its entirety.

In some embodiments, the beta-lapachone compound is menadione, 2,2-dimethyl-(Z)-6-phenylimino-3,4,5,6-tetrahydro-2H-naphtho[1,2-b]oxin-5-one[phenylimine lapachone], 2,2-dimethyl-(Z)-6-(4-methyl-phenylimino)-3,4,5,6-tetrahydro-2H-naphtho[1,2-b]oxin-5-one[p-methylphenylimine lapachone], 2,2-dimethyl-(Z)-6-(4-methoxyphenylimino)-3,4,5,6-tetrahydro-2H-naphtho[1,2-b]oxin-5-one[p-methoxyphenylimine lapachone], 2,2-dimethyl-(Z)-6-(4-nitrophenylimino)-3,4,5,6-tetrahydro-2H-naphtho[1,2-b]oxin-5-one[p-nitrophenylimine lapachone], or 2,2-dimethyl-(Z)-6-(4-bromophenylimino)-3,4,5,6-tetrahydro-2H-naphtho[1,2-b]oxin-5-one[p-bromophenylimine lapachone](see K. E. Reinicke et al, *Clin. Cancer Res.*, 2005, 11(8), 3055-3064).

In some embodiments, the beta-lapachone compound is a prodrug of beta-lap. In some embodiments, the beta-lapachone compound comprises a polymer conjugated with a pH-sensitive prodrug of beta-lapachone, wherein the compound is forms a micelle, and wherein the pH-sensitive prodrug comprises a pH-sensitive linker selected from the group consisting of: an aryl imine and an aliphatic imine. In some embodiments, the pH-sensitive linker is an aryl imine. In some embodiments, the aryl imine is a phenyl imine. In some embodiments, the phenyl comprises a substitutent. In some embodiments, the substituent is at the para position. In some embodiments, the substituent is —OH, —$NH_2$, —SH, or maleimide

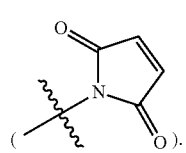

In some embodiments, the substituent is maleimide

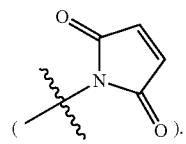

In some embodiments, the pH-sensitive linker is an aliphatic imine. In some embodiments, the Cα of the aliphatic imine comprises at least one substitutent. In some embodiments, the Cα of the aliphatic imine comprises two substitutents. In some embodiments, the substitutents are both methyl. In some embodiments, the prodrug is selected from the group consisting of:

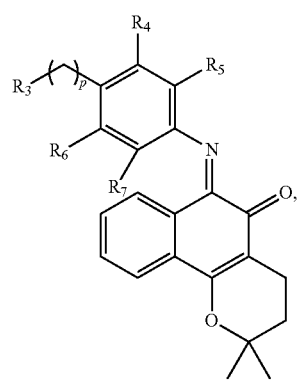

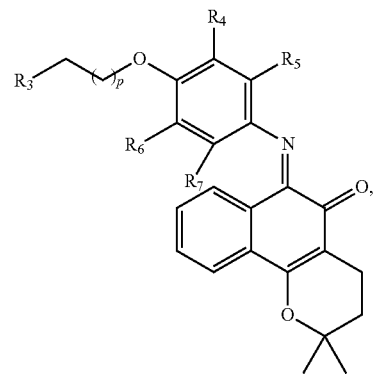

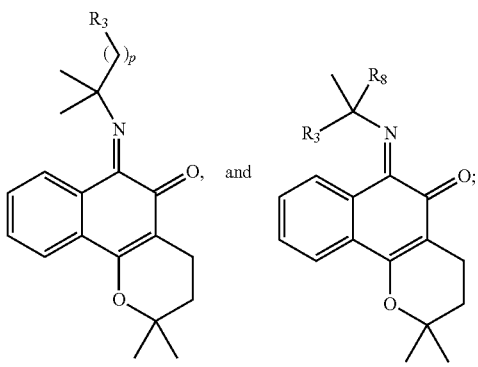

wherein $R_8$ is a side chain of a D or L amino acid other than —H; $R_3$ is —$NH_2$, —OH, —SH, or

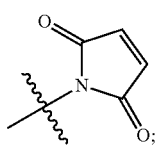

each of $R_4$, $R_5$, $R_6$, and $R_7$ is independently —H, —X, —OCH$_3$, or —CH$_3$; X is a halogen; and p is an integer between 0 and 20. In some embodiments, $R_8$ is —CH$_3$. In some embodiments, $R_3$ is

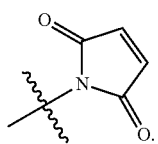 [SMILES: *N1C(=O)C=CC1=O]

In some embodiments, $R_3$ is —OH. In some embodiments, each of $R_4$, $R_5$, $R_6$, and $R_7$ is H. In some embodiments, X is Cl, Br, I, or F. In some embodiments, p is 0-6. In some embodiments, the prodrug is linked to the polymer by a bond selected from the group consisting of: an ester bond, an amide bond, a disulfide bond, or a thioether bond.

In some embodiments, the micelle formulation is stable at a neutral pH (e.g. a physiologically neutral pH) and releases beta-lapachone at an acidic pH (e.g. a physiologically acidic pH). In some embodiments, the therapeutic agent is a β-lapachone prodrug with a linkage of: ketal, acyl hydrazone, aliphatic imine, aromatic imine bond, or a combination thereof. In some embodiments, the ketal, acyl hydrazone, aliphatic imine, or aromatic imine bond is a pH sensitive linkage. In some embodiments, the prodrug is selected from:

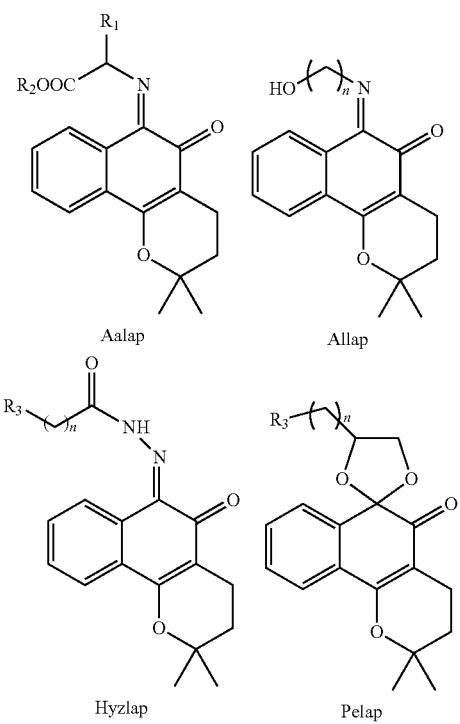

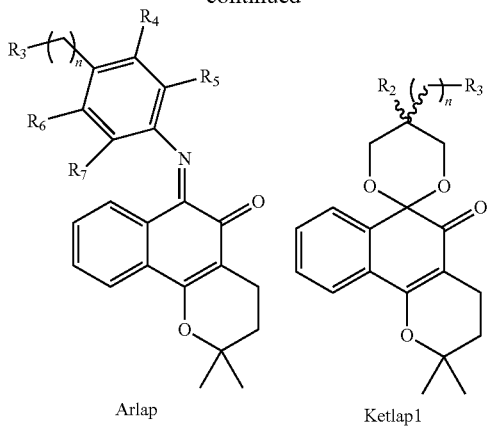

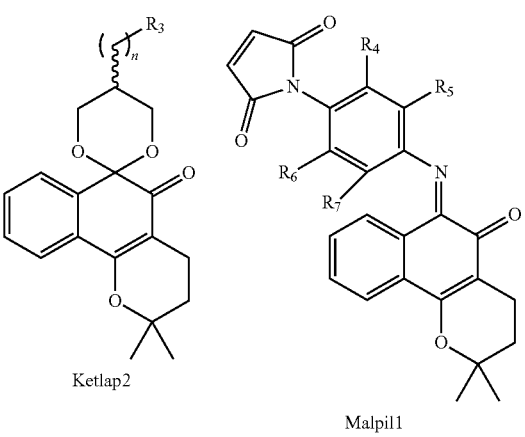

wherein $R_1$ is a side chain of D or L amino acids; $R_2$ is an alkyl group or an aromatic group; $R_3$ is NH$_2$, OH, or SH; each of $R_4$, $R_5$, $R_6$, and $R_7$ is independently H, X, OCH$_3$, or CH$_3$; X is a halogen; and n is an integer between 1 and 20. In some embodiments, X is Cl, Br, I, or F. In some embodiments, $R_2$ is CH$_3$, CH$_2$CH$_3$, or Bzl. Non-limiting examples of prodrugs of the invention include the following:

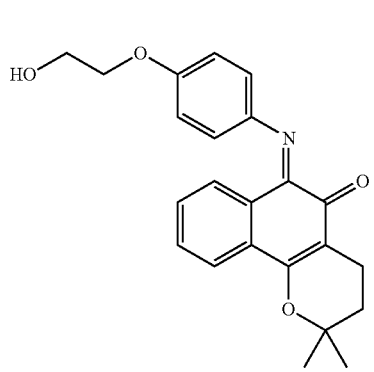
EAPIL
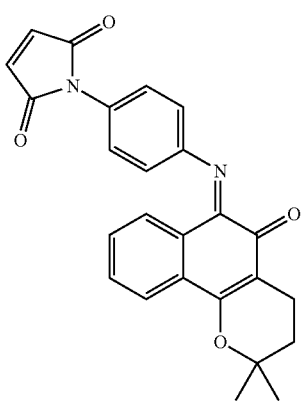
MAIPIL
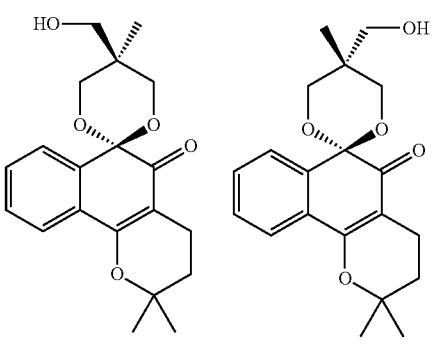
KETLAP-1    KETLAP-2
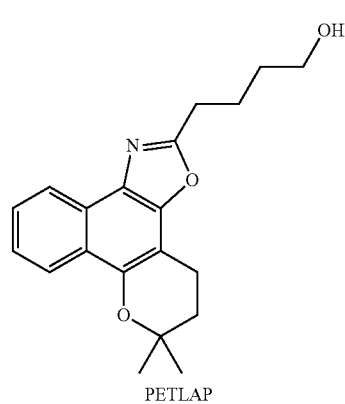
PETLAP
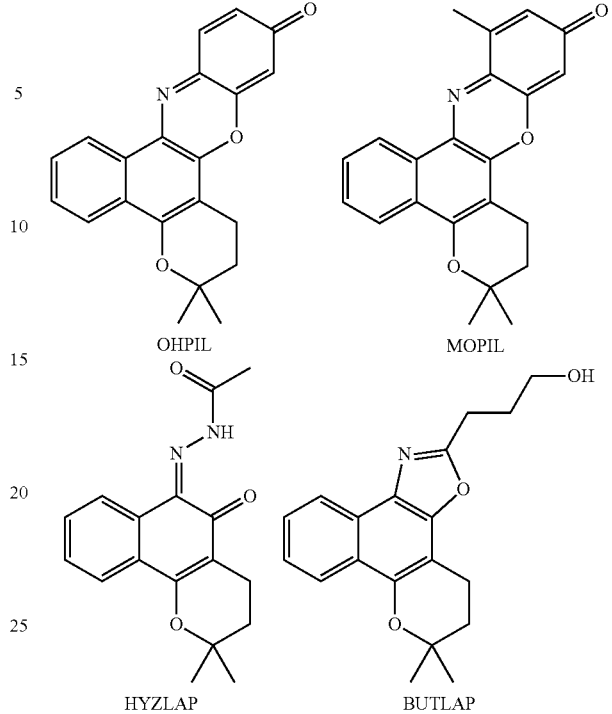
OHPIL    MOPIL
HYZLAP    BUTLAP
In some embodiments, the biocompatible polymeric prodrug micelle has the formula:
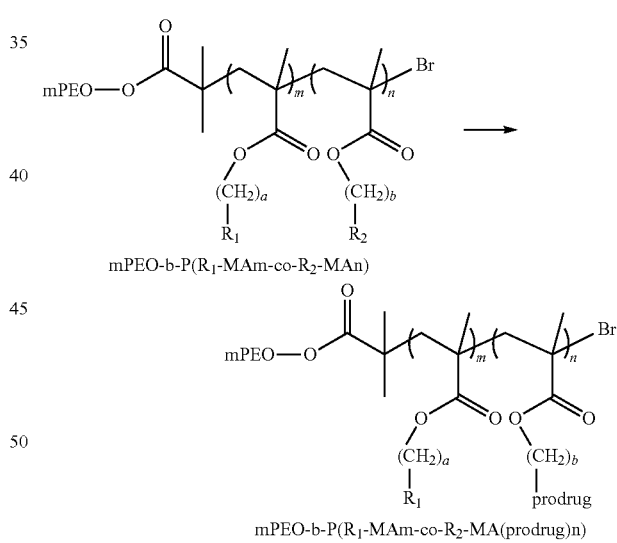
mPEO-b-P(R₁-MAm-co-R₂-MAn)
mPEO-b-P(R₁-MAm-co-R₂-MA(prodrug)n)
R1=PDMA, PDEA, PDiPA, PDnPA, PDBA, Pc5A, Pc6A, Pc7A, etc.
R2=PDMS, PDBS, PDPS etc.
wherein R1 and R2 are each independently selected from:
| Code (R1 and R₂) | Structure |
|---|---|
| PDMA | 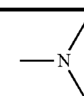 |

-continued

| Code (R1 and R2) | Structure |
| --- | --- |
| PDEA | 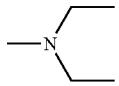 |
| PDiPA | 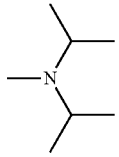 |
| PDnPA | 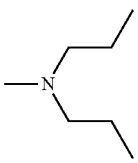 |
| PDBA | 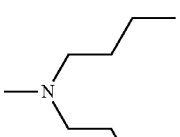 |
| Pc5A | 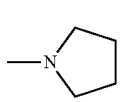 |
| Pc6A | 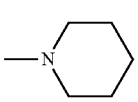 |
| Pc7A | 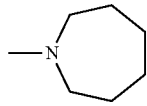 |
| PDMS | 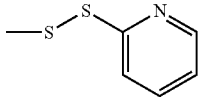 |
| PDBS | 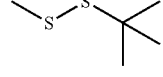 |
| PDPS | 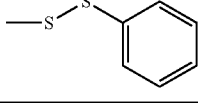 |

In some embodiments, the micelle is stable at a neutral pH and releases beta-lapachone at a physiologically acidic pH.

In some embodiments, the beta-lapachone compound is in a formulation (such as a micelle formulation). In some embodiments, the β-lapachone compound is formulated with cyclodextrins. In other embodiments, the β-lapachone compound is formulated with SPIO-micelles or ligand-encoded (e.g., $α_vβ_3$) micelles. In other embodiments, the β-lapachone compound is in a pH-sensitive micelle as described in International Patent Application No. PCT/US2011/001418, filed Aug. 11, 2011, the contents of which are hereby incorporated by reference in its entirety.

Methods of the Invention

Provided herein are methods for using the expression levels of NQO1 and/or catalase in tumor cells to select individuals or subpopulations of individuals with cancer that will benefit from treatment with an NQO1 bioactivatable drug. Also provided herein are methods for predicting the responsiveness of an individual with cancer to a treatment with an NQO1 bioactivatable drug based on the expression levels of NQO1 and/or catalase in tumor cells from that individual. In addition, provided herein are methods for treating an individual with cancer who has been selected for treatment based on the level of NQO1 enzymatic activity in the individual's cancer cells.

Methods for Determining Whether an Individual with Cancer is Suitable for Treatment With an NQO1 Bioactivatable Drug Using the methodologies described herein, one of skill in the art can identify and/or select individuals or subpopulation of individuals who are suitable for anti-cancer treatment with an NQO1 bioactivatable drug. In some aspects, provided herein are methods of determining whether an individual with cancer is suitable for treatment with an NQO1 bioactivatable drug. In some embodiments, a ratio of the NQO1 expression level over the catalase expression level in cancer cells from the individual being at least any of about 25 fold, about 30 fold, about 35 fold, about 40 fold, about 45 fold, about 50 fold, about 55 fold, about 60 fold, about 65 fold, about 70 fold, about 75 fold, about 80 fold, about 85 fold, about 90 fold, about 95 fold, about 100 fold, about 105 fold, about 110 fold, about 120 fold, about 130 fold, about 140 fold, about 150 fold, about 160 fold, about 170 fold, about 180 fold, about 190 fold, about 200 fold, about 250 fold, or about 300 fold, inclusive, including any value in between these numbers, of the ratio of a normal tissue indicates that the individual is suitable for treatment with an NQO1 bioactivatable drug. In some embodiments, the NQO1 bioactivatable drug is a β-lapachone compound, a streptonigrin, or a deoxynyboquinone (DNQ). In other embodiments, the cancer is selected from the group consisting of lung cancer (such as, but not limited to, non small cell lung cancer (NSCLC)), prostate cancer, breast cancer, colon cancer, and melanoma. In some embodiments, the individual is a human. In another embodiment, the normal tissue is a cancer associated normal tissue. In some embodiments, the cancer cells are obtained from a cancer biopsy from the individual or from circulating cancer cells from the individual.

In other embodiments, NQO1 enzymatic activity can be used to determine whether an individual with cancer is suitable for a treatment with an NQO1 bioactivatable drug (See FIG. 20). In some embodiments, NQO1 enzymatic activity in the cancer cells of an individual greater than about 50, about 60, about 70, about 80, about 90, about 100, about 110, about 120, about 130, about 140, or about 150 units, inclusive, including any values in between these numbers, indicates that the individual is suitable for treatment. In another embodiment, NQO1 enzymatic activity in the cancer cells of an individual ≥50 units indicates that the individual is suitable for treatment. In yet another embodiment, NQO1 enzymatic activity in the cancer cells of an individual ≥90 units indicates that the individual is suitable for treatment. In some embodiments, the NQO1 bioactivatable drug is a β-lapachone compound, a streptonigrin, or a deoxynyboquinone (DNQ). In other embodiments, the cancer is selected from the group consisting of lung cancer (such as, but not limited to, non small cell lung cancer (NSCLC)), prostate cancer, breast cancer, colon cancer, and melanoma. In some embodiments, the individual is a human. In some embodiments, the cancer cells are obtained from a cancer biopsy from the individual or from circulating cancer cells from the individual.

In other embodiments, the absence or presence of NQO1 gene polymorphisms can be used to determine whether an individual with cancer is suitable for a treatment with an NQO1 bioactivatable drug. In some embodiments, an individual not having an NQO1 gene polymorphism at C609T and at C465T or having a C465T/C465T polymorphism indicates that the individual is suitable for treatment with an NQO1 bioactivatable drug. In some embodiments, the C609T and C465T mutations and/or the C465T/C465T mutations are detected in a sample taken from the individual using the methods described herein. The sample can be from a cancer associated normal tissue or the sample can be obtained from a cancer biopsy from the individual or from circulating cancer cells from the individual. In another embodiment, the sample is a cancer tissue sample or a PBMC sample. In some embodiments, the NQO1 bioactivatable drug is a β-lapachone compound, a streptonigrin, or a deoxynyboquinone (DNQ). In other embodiments, the cancer is selected from the group consisting of lung cancer (such as, but not limited to, non small cell lung cancer (NSCLC), prostate cancer, breast cancer, colon cancer, and melanoma. In some embodiments, the individual is a human.

Methods for Predicting Responsiveness of an Individual with Cancer to a Treatment With an NQO1 Bioactivatable Drug Predicting the responsiveness of an individual with cancer to a treatment with an NQO1 bioactivatable drug can also be determined using the methodologies described herein. In some aspects, there is provided a method of predicting responsiveness of an individual with cancer to a treatment with an NQO1 bioactivatable drug. In some embodiments, a ratio of the NQO1 expression level over the catalase expression level in cancer cells from the individual being at least any of about 25 fold, about 30 fold, about 35 fold, about 40 fold, about 45 fold, about 50 fold, about 55 fold, about 60 fold, about 65 fold, about 70 fold, about 75 fold, about 80 fold, about 85 fold, about 90 fold, about 95 fold, about 100 fold, about 105 fold, about 110 fold, about 120 fold, about 130 fold, about 140 fold, about 150 fold, about 160 fold, about 170 fold, about 180 fold, about 190 fold, about 200 fold, about 250 fold, or about 300 fold (inclusive, including any value in between these numbers) of the ratio of a normal tissue indicates that the individual is more likely to be responsive to the treatment with an NQO1 bioactivatable drug. In some embodiments, the NQO1 bioactivatable drug is a β-lapachone compound, a streptonigrin, or a deoxynyboquinone (DNQ). In other embodiments, the cancer is selected from the group consisting of lung cancer (such as, but not limited to, non small cell lung cancer (NSCLC)), prostate cancer, breast cancer, colon cancer, and melanoma. In some embodiments, the individual is a human. In another embodiment, the normal tissue is a cancer associated normal tissue or a normal tissue of the same type as the cancer cells from an individual without cancer. In some embodiments, the cancer cells are obtained from a cancer biopsy from the individual or from circulating cancer cells from the individual.

In other embodiments, NQO1 enzymatic activity can be used to predict the responsiveness of an individual with cancer to treatment with an NQO1 bioactivatable drug. In some embodiments, NQO1 enzymatic activity in the cancer cells of an individual greater than about 50, about 60, about 70, about 80, about 90, about 100, about 110, about 120, about 130, about 140, or about 150 units, inclusive, including any values in between these numbers, indicates that the individual is more likely to respond to the treatment. In another embodiment, NQO1 enzymatic activity in the cancer cells of an individual ≥50 units indicates that the individual is more likely to respond to the treatment. In yet another embodiment, NQO1 enzymatic activity in the cancer cells of an individual ≥90 units indicates that the individual is more likely to respond to the treatment. In some embodiments, the NQO1 bioactivatable drug is a β-lapachone compound, a streptonigrin, or a deoxynyboquinone (DNQ). In other embodiments, the cancer is selected from the group consisting of lung cancer (such as, but not limited to, non small cell lung cancer (NSCLC)), prostate cancer, breast cancer, colon cancer, and melanoma. In some embodiments, the individual is a human. In some embodiments, the cancer cells are obtained from a cancer biopsy from the individual or from circulating cancer cells from the individual.

In other embodiments, the absence or presence of NQO1 gene polymorphisms can be used to determine whether an individual with cancer is more likely to be responsive to a treatment with an NQO1 bioactivatable drug. In some embodiments, an individual not having an NQO1 gene polymorphism at C609T and at C465T or having a C465T/C465T polymorphism indicates that the individual is more likely to be responsive to a treatment with an NQO1 bioactivatable drug. In some embodiments, the C609T and C465T mutations and/or the C465T/C465T mutations are detected in a sample taken from the individual using the methods described herein. The sample can be from a cancer associated normal tissue or the sample can be obtained from a cancer biopsy from the individual or from circulating cancer cells from the individual. In another embodiment, the sample is a cancer tissue sample or a PBMC sample. In some embodiments, the NQO1 bioactivatable drug is a β-lapachone compound, a streptonigrin, or a deoxynyboquinone (DNQ). In other embodiments, the cancer is selected from the group consisting of lung cancer (such as, but not limited to, non small cell lung cancer (NSCLC)), prostate cancer, breast cancer, colon cancer, and melanoma. In some embodiments, the individual is a human.

Methods for Treating an Individual with Cancer

In some aspects, provided herein are methods for treating an individual with cancer with an NQO1 bioactivatable drug. "Treating" or "treatment" refers to therapeutic treatment wherein the object is to slow down (lessen) if not cure the targeted pathologic condition or disorder or prevent recurrence of the condition. A subject is successfully "treated" for cancer if, after receiving a therapeutic amount of an NQO1 bioactivatable drug, the subject shows observable and/or measurable reduction in or absence of one or more signs and symptoms of the cancer. For example, significant reduction in the number of cancer cells or absence of the cancer cells; reduction in the tumor size; inhibition (i.e., slow to some extent and preferably stop) of tumor metastasis; inhibition, to some extent, of tumor growth; increase in length of remission, and/or relief to some extent, one or more of the symptoms associated with the specific cancer; reduced morbidity and mortality, and improvement in quality of life issues. Reduction of the signs or symptoms of a disease may also be felt by the patient. Treatment can achieve a complete response, defined as disappearance of all signs of cancer, or a partial response, wherein the size of the tumor is decreased, preferably by more than 50 percent, more preferably by 75%. A patient is also considered treated if the patient experiences stable disease. These parameters for assessing successful treatment and improvement in the disease are readily measurable by routine procedures familiar to a physician of appropriate skill in the art. An "effective amount" refers to an amount effective, at dosages and for periods of time necessary, to achieve the desired therapeutic or prophylactic result. A "therapeutically effective amount" of a drug may vary according to factors such as the disease state, age, sex, and weight of the individual, and the ability of the antibody to elicit a desired response in the individual. A therapeutically effective amount is also one in which any toxic or detrimental effects of the therapeutic agent are outweighed by the therapeutically beneficial effects.

In some embodiments, an individual with cancer is treated with an effective amount of an NQO1 bioactivatable drug if the ratio of the NQO1 expression level over the catalase expression level in the cancer cells from the individual is at least any of about 25 fold, about 30 fold, about 35 fold, about 40 fold, about 45 fold, about 50 fold, about 55 fold, about 60 fold, about 65 fold, about 70 fold, about 75 fold, about 80 fold, about 85 fold, about 90 fold, about 95 fold, about 100 fold, about 105 fold, about 110 fold, about 120 fold, about 130 fold, about 140 fold, about 150 fold, about 160 fold, about 170 fold, about 180 fold, about 190 fold, about 200 fold, about 250 fold, or about 300 fold, inclusive, including any value in between these numbers, of the ratio in a normal tissue. The NQO1 expression level and the catalase expression level in cancer cells and normal tissue can be determined using the methodologies described herein. In some embodiments, the NQO1 bioactivatable drug is a β-lapachone compound, a streptonigrin, or a deoxynyboquinone (DNQ). In other embodiments, the cancer is selected from the group consisting of lung cancer (such as, but not limited to, non small cell lung cancer (NSCLC)), prostate cancer, breast cancer, colon cancer, and melanoma. In some embodiments, the individual is a human. In another embodiment, the normal tissue is a cancer associated normal tissue or a normal tissue of the same type as the cancer cells from an individual without cancer. In some embodiments, the cancer cells are obtained from a cancer biopsy from the individual or from circulating cancer cells from the individual. In other embodiments, the method may comprise 1) determining the ratio of the NQO1 expression level over the catalase expression level in the cancer cells from the individual; and 2) treating the individual with an NQO1 bioactivatable drug if the ratio of the NQO1 expression level over the catalase expression level in the cancer cells is at least any of about 50 fold, about 55 fold, about 60 fold, about 65 fold, about 70 fold, about 75 fold, about 80 fold, about 85 fold, about 90 fold, about 95 fold, about 100 fold, about 105 fold, about 110 fold, about 120 fold, about 130 fold, about 140 fold, about 150 fold, about 160 fold, about 170 fold, about 180 fold, about 190 fold, or about 200 fold, inclusive, including any value in between these numbers, of the ratio in a normal tissue.

In other embodiments, provided herein are methods for treating an individual with cancer with an effective amount of an NQO1 bioactivatable drug if NQO1 enzymatic activity in the cancer cells of the individual is greater than about 50, about 60, about 70, about 80, about 90, about 100, about 110, about 120, about 130, about 140, or about 150 units, inclusive, including any values in between these numbers. NQO1 enzymatic activity can be determined using the methodologies described herein. In another embodiment, the method comprises treating an individual with cancer with an NQO1 bioactivatable drug if NQO1 enzymatic activity in the cancer cells of the individual is ≥50 units. In yet another embodiment, the method comprises treating an individual with cancer with an NQO1 bioactivatable drug if NQO1 enzymatic activity in the cancer cells of the individual is ≥90 units. In some embodiments, the NQO1 bioactivatable drug is a β-lapachone compound, a streptonigrin, or a deoxynyboquinone (DNQ). In other embodiments, the cancer is selected from the group consisting of lung cancer (such as, but not limited to, non small cell lung cancer (NSCLC)), prostate cancer, breast cancer, colon cancer, and melanoma. In some embodiments, the individual is a human. In some embodiments, the cancer cells are obtained from a cancer biopsy from the individual or from circulating cancer cells from the individual. In other embodiments, the method may comprise 1) determining the NQO1 enzymatic activity in the cancer cells of the individual; and 2) treating the individual with an NQO1 bioactivatable drug if NQO1 enzymatic activity in the cancer cells of the individual is greater than about 50, about 60, about 70, about 80, about 90, about 100, about 110, about 120, about 130, about 140, or about 150 units, inclusive, including any values in between these numbers.

In other embodiments, provided herein are methods for treating an individual with cancer comprising administering an effective amount of an NQO1 bioactivatable drug to the individual, wherein the individual is selected for the treatment based on the absence of C609T and C465T mutations in the NQO1 gene or the presence of C465T/C465T polymorphism in a sample from the individual. In some embodiments, the C609T and C465T mutation and/or the C465T/C465T mutations are detected in a sample taken from the individual using the methods described herein. The sample can be from a cancer associated normal tissue or the sample can be obtained from a cancer biopsy from the individual or from circulating cancer cells from the individual. In another embodiment, the sample is a cancer tissue sample or a PBMC sample. In some embodiments, the NQO1 bioactivatable drug is a β-lapachone compound, a streptonigrin, or a deoxynyboquinone (DNQ). In other embodiments, the cancer is selected from the group consisting of lung cancer (such as, but not limited to, non small cell lung cancer (NSCLC)), prostate cancer, breast cancer, colon cancer, and melanoma. In some embodiments, the individual is a human. In other embodiments the method may comprise 1) detecting the absence or presence of C609T, C465T, or C465T/C465T polymorphisms in a sample from an individual with cancer; and 2) selecting the individual for treatment with an NQO1 bioactivatable drug based on the absence of C609T and C465T mutations in the NQO1 gene or the presence of C465T/C465T polymorphism in the sample.

In some aspects of the methods of treatment disclosed herein, the method can further comprise monitoring treatment of an NQO1 bioactivatable drug in an individual by measuring one or more protein levels in cancer cells from the individual before and after the treatment, wherein the protein measured is selected from the group consisting of NQO1, catalase, small μ-calpain subunit, large μ-calpain subunit, apoptosis inducing factor (AIF), and PARP-1.

Combination Treatments

NQO1 bioactivatable drug treatment may be combined with one or more DNA damaging therapies. Additionally, treatment with an NQO1 bioactivatable drug may be employed in either an adjuvant or neoadjuvant setting. By "adjuvant setting," it is meant a clinical setting in which an individual has had a history of cancer, and generally (but not necessarily) has been responsive to therapy, which includes, but is not limited to, surgery, radiotherapy, and chemotherapy. However, because of a history of the proliferative disease (such as cancer), these individuals are considered at risk of developing that disease. By "neoadjuvant setting," it is meant the method may be carried out before the primary/definitive therapy. In some embodiments, the individual has previously been treated. In other embodiments, the individual has not previously been treated. In some aspects, the treatment is a first line therapy.

Accordingly, in some embodiments, the method comprises 1) screening patients to determine NQO1 status; 2) administering DNA damaging therapies (radiation and/or chemotherapy) with doses ranging from low or sub-threshold to standard doses; and 3) administering β-lap such that the tumor is exposed to the drug (which takes a unique understanding of the pharmacokinetics and pharmacodynamics of the drug) for ≥2 hrs. In some embodiments, systemic drug exposure to β-lap does not exceed 12 hrs. In some embodiments, an NQO1 bioactivatable drug (β-lap, streptonigrin, or DNQ) is formulated with cyclodextrins (e.g., HPβCD) or with micelles (e.g., SPIO-micelles; ligand-encoded (e.g., $α_vβ_3$) micelles; prodrugs linked to micelle components as delivery vehicles). In some embodiments, an NQO1 bioactivatable drug enhances the sensitivities of DNA damaging antitumor agents (e.g., ionizing radiation, chemotherapeutics or photodynamic (PDT) therapeutics). In some embodiments, administering an NQO1 bioactivatable drugs during and/or immediately after IR and/or chemotherapeutic drug exposure results in the creation of NQO1-driven, tumor specific DNA lesions. In some embodiments, because of the loss of NAD+/ATP nucleotides, DNA repair is inhibited and DNA lesions synergistically amplified. In some embodiments, selective DNA damage amplification with NQO1 bioactivatable drugs is achieved in specific solid cancers, such as non-small cell lung, prostate, breast, pancreatic and colon tumors that have elevated levels of NQO1, whereas normal tissues are spared due to their low or no expression of the NQO1 bioactivating enzyme.

Administration of NQO1 Bioactivatable Drug Compositions (Such as β-Lap)

This mechanism, in particular the tumor-selective amplifying effect of β-lap on the effects of radiation and chemotherapy, offers novel methods of use for optimal clinical benefit. In particular, the order of administering chemotherapy and radiation and an NQO1 bioactivatable drug (such as β-lap), becomes important. Currently, chemotherapy drugs and radiation, as well as other standard of care drugs, are typically administered either together and in many cases, in a random order, or in an order taking into account factors other than drug mechanism of action. In some embodiments, a method disclosed herein comprises first administering DNA damaging agents including radiation and chemotherapy, followed by administration of an NQO1 bioactivatable drug (such as β-lap), to take advantage of the tumor-selective amplifying effect of β-lap on DNA damage, for optimal clinical benefit.

In some embodiments, tumor exposure to an NQO1 bioactivatable drug (such as β-lap) occurs for ≥2 hrs, but not exceeding 12 hrs. In some embodiments, normal cells/tissue undergo DNA damage at exposures to an NQO1 bioactivatable drug (such as β-lap) beyond 12 hrs. In some embodiments, tumor exposure time to an NQO1 bioactivatable drug (such as β-lap) is between about 4 and about 22 hrs. In some embodiments, tumor exposure time to an NQO1 bioactivatable drug (such as β-lap) is between about 4 and about 10 hrs.

In some embodiments, an NQO1 bioactivatable drug (such as β-lap) is administered within two hours after exposure to a tumor killing agent. In certain instances, administering an NQO1 bioactivatable drug (such as β-lap) 2 hours or more after exposure to a tumor killing agent allows cells time to repair SSBs effectively, abrogating synergy. In certain instances, treating NQO1+ cancer cells/tissue with NQO1 bioactivatable drugs prior to exposure to a tumor killing agent does not result in radiosensization because cells recover from SSBs caused by the treatment (especially at sub-lethal doses) and losses of NAD+ and ATP, effectively avoiding PARP1 hyperactivation.

In some embodiments, a tumor killing agent (e.g., radiation and chemotherapy) is administered at sub-threshold and low doses, followed by an NQO1 bioactivatable drug (such as β-lap). Chemotherapy and radiation are known to have undesired side-effects in patients including hair loss, red blood cell loss etc. Synergy between tumor killing agents and NQO1 bioactivatable drugs allows the use of nonlethal doses of IR to be combined with nonlethal doses of NQO1 bioactivatable drugs to afford a significant lethal event in vitro and in vivo.

An effective amount of the NQO1 bioactivatable drug compositions described herein may be administered to an individual for treating cancer by any suitable methods, for example, by injection or infusion. In some embodiments, the composition is administered locally or systemically. In some embodiments, the composition is administered by intraperitoneal, intravenous, subcutaneous, and intramuscular injections, and other forms of administration such as oral, mucosal, via inhalation, sublingually, etc. The dosage required for the treatment depends on the choice of the route of administration, the nature of the formulation, the nature of the individual's illness, the individual's size, weight, surface area, age and sex; other drugs being administered, and the judgment of the attending physician. In some subjects, more than one dose may be required. Frequency of administration may be determined and adjusted over the course of therapy. For example, frequency of administration may be determined or adjusted based on the type and stage of the cancer to be treated, whether the agent is administered for therapeutic purposes, previous therapy, the patient's clinical history and response to the agent, and the discretion of the attending physician. Administration of the composition in accordance with the method in the present invention can be continuous or intermittent.

EXAMPLES

Figure 1:
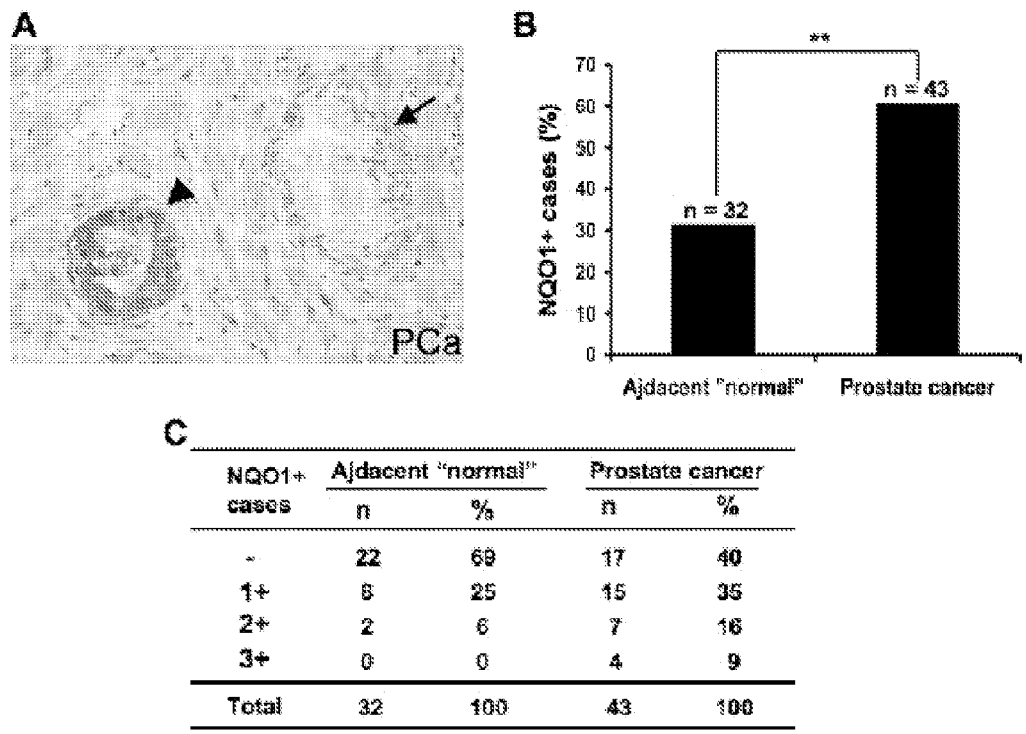
FIG. 1 depicts NQO1 expression level is elevated in prostate cancer over adjacent normal tissue. (a). NQO1 immunostaining in a representative sample from a prostate cancer patient. Arrowhead indicates neoplastic prostate gland, while arrow points to an adjacent normal gland. (b). Statistical analyses of NQO1 expression in cancer versus normal adjacent tissue. Expression was defines as ≥10% cells staining for NQO1. "n" indicates the number of cases used in each group. **p<0.05 (Two sided Fisher's exact test). (c). Semi-quantitative evaluation was assessed according to intensity of staining [grade 0 (negative) to 3+(highest intensity)].
Figure 2:
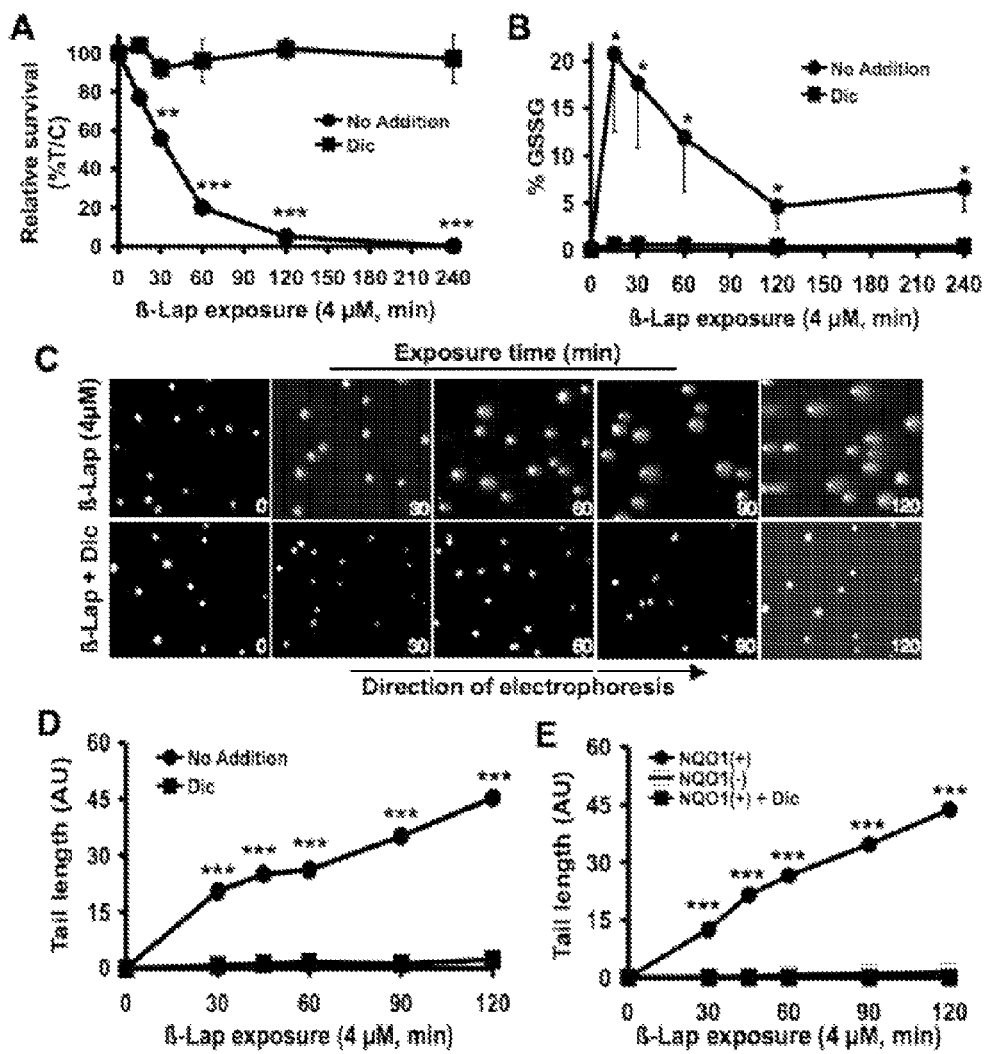
FIG. 2 depicts β-lap induced, NQO1-mediated prostate cancer cell death is initiated by ROS formation and DNA breaks. (a). Relative survival of β-lap treated DU145 cells in the presence or absence of 40 μM Dic. Data are means±SE for three independent experiments performed in six duplicates. (b). ROS formation monitored using Oxidative Glutathione (GSSG) recycling assays in DU145 cells treated as in A. Experiments were performed at least three times in duplicate each and reported as means±SE. (c). Alkaline comet assays detect DNA breaks in DU145 cells. (d-e). Quantitative analyses of comet tail length using NIH Image J software. In (d)., DU145 cells were used, while in (e) responses of LNCaP cells were shown. Data represent means±SE calculated from 100 cells. *p<0.001,  p<0.01, * p<0.05.

Example 1

β-Lap Induces Prostate Cancer Cell Death Via NQO1-Induced ROS Formation and SSBs The following data utilize a human prostate cancer model. Similar data are available for NSCLC cells. In each case, responses of cells to the NQO1 bioactivatable drug, β-lap, are shown first, followed by the synergistic responses using IR+β-lap, particularly studies elucidating the mechanism of action of tumor-selective DNA damage amplification and PARP1 hyperactivation Immunohistochemical (IHC) analyses of human prostate tumor and associated normal tissue revealed that ~60% of these cancers had elevated NQO1 levels (FIG. 1). Using human PC-3 prostate cancer cells that express high levels of endogenous NQO1, the inventors showed that the cytotoxic effects of β-lap were NQO1-dependent, inhibited by dicoumarol (FIG. 2). This was confirmed in DU145 and in NQO1+ versus NQO1-LNCaP cells. Importantly, only ~120 mins of exposure to 4 μM β-lap was sufficient to achieve maximal cytotoxicity FIG. 2, where significant levels of glutathione were oxidized (note rapid and elevated levels of % GSSG in 20-30 mins FIG. 2), suggesting dramatic ROS formation. Dramatic increases in SSBs were seen by alkaline comet assays, but DSBs, as assessed by neutral comet assays, were not noted FIG. 2. Similar results were found using DU145, and NQO1+LNCaP cells. In contrast, NQO1-deficient LNCaP cells were not responsive to β-lap as described.

Figure 3:
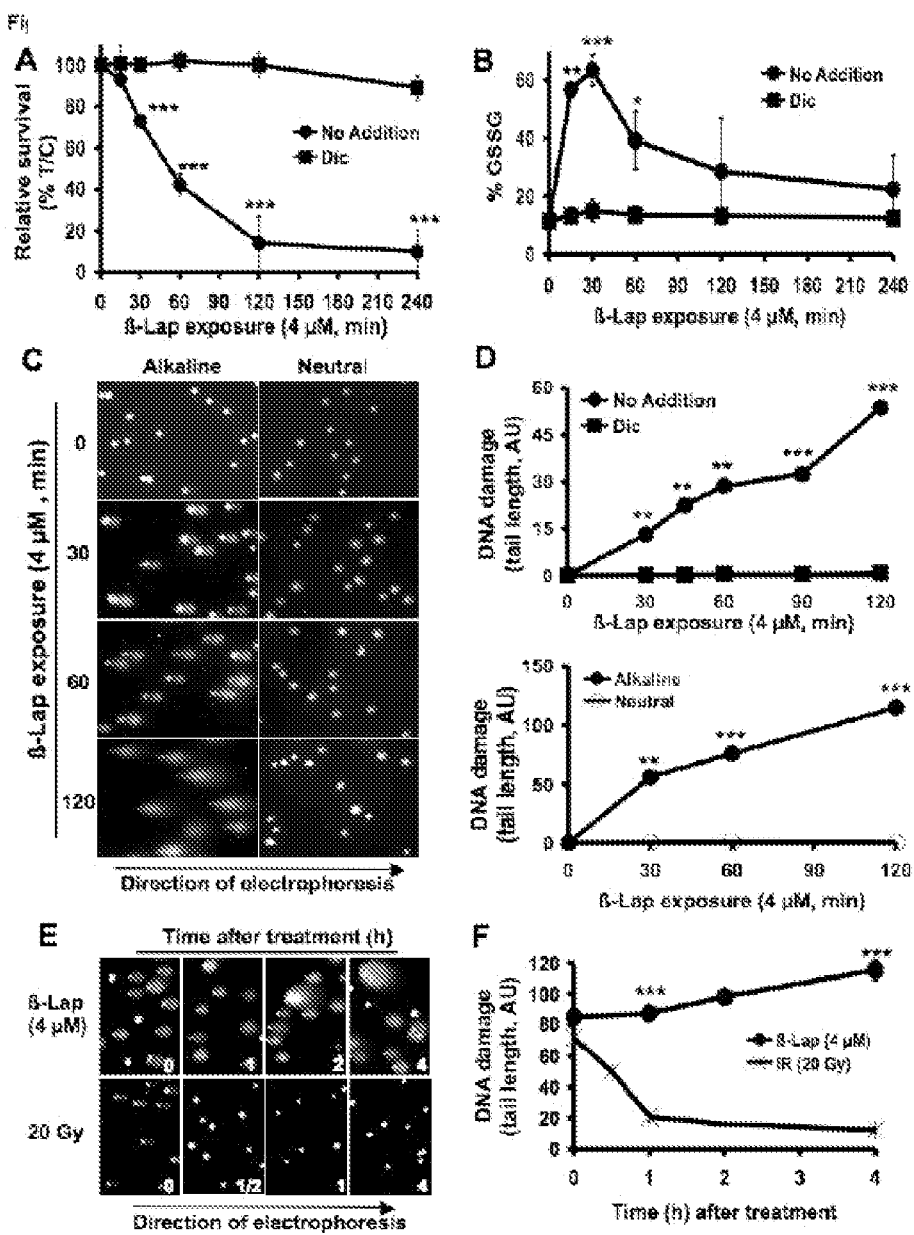
FIG. 3 depicts β-lap induced, NQO1-mediated ROS formation and DNA single-strand breaks (SSBs) are required for cell death in exposed human prostate cancer cells. (a). Relative survival of PC-3 cells after β-lap treatment in the presence or absence of dicoumarol (Dic, 40 μM). Data are means±SE for three independent experiments performed in sextuplicate. (b). ROS formation was indirectly monitored using the GSSG recycling assay in β-lap-exposed PC-3 cells in the presence or absence of 40 uM Dic. Graphed results were means±SE and represented three experiments performed in duplicate. (c). Alkaline v. neutral comet assays assessed total DNA damage or DNA double strand breaks (DSBs), respectively (not shown). (d). DNA damage assessment (arbitrary units (AU) of comet tail lengths) using NIH Image J software. Data are means±SE from 100 cells. *p<0.001,  p<0.01, * p<0.05. (e). DNA damage in PC-3 cells after IR (20 Gy) versus β-lap (4 uM, 2 h). (f). Comet tail lengths (AU) assessed using NIH Image J software. Data are means±SE from 100 cells. *p<0.001,  p<0.01, * p<0.05.
Figure 4:
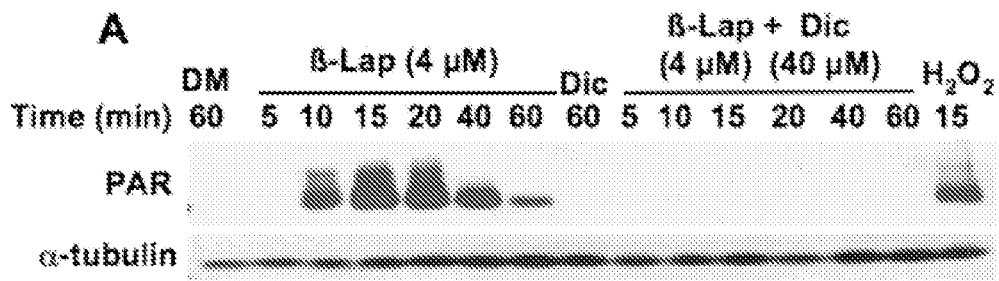
FIG. 4 depicts β-lap hyper-activates PPAR-1 in DU145 cells. Resulting in $NAD^+$ and ATP depletions. (a). PPAR-1 hyperactivation was noted in DU145 cells treated with 4 μM β-lap by PAR formation at the indicated times. NQO1 dependency was shown using Dic co-additions. (b). $\gamma H_2 AX$ levels were monitored in DU145 cells treated with 4 μM β-lap at indicated times as a measure of DSB formation. Note the delayed formation of DSBs after PAR formation dissipates. DM:DMSO; $H_2O_2$, hydrogen peroxide. (c). DU145 cells treated as above were analyzed for $NAD^+$ and ATP levels. Results are means±SE for experiments performed three times in duplicate. *p<0.001,  p<0.01, * p<0.05. Top asterisks for $NAD^+$, while bottom asterisks are for ATP.
Figure 4:
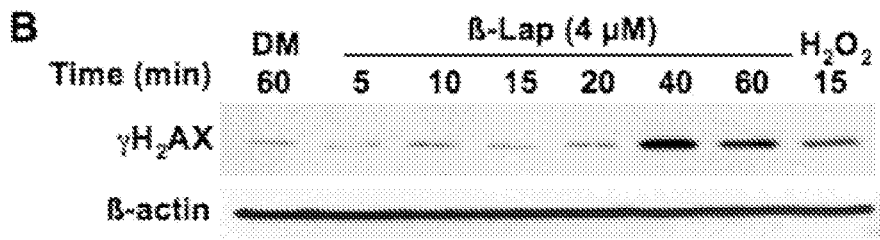
Figure 4:
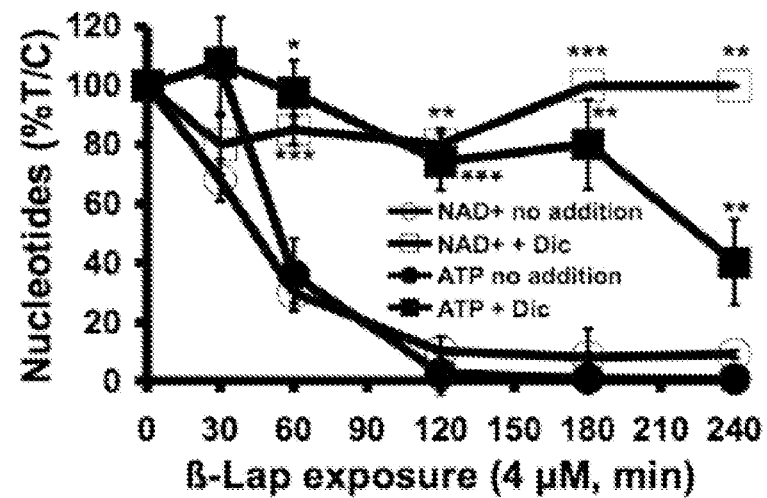

DNA damage and repair responses of β-lap-treated NQO1-expressing PC-3 cells were compared to responses after IR treatment (FIG. 4). Extensive DNA lesions were noted in PC-3 cells after exposure to 4 μM β-lap, equivalent to 20 Gy by alkaline assays. However, neutral comet assays revealed DSBs after IR, but not after β-lap exposures. Exposure of PC-3 cells to IR (20 Gy) resulted in DNA damage that was quickly repaired within 1 h post-treatment, whereas DNA damage created by 4 μM β-lap was not repaired, but escalated over the 4 h time-period assessed, suggesting repair inhibition (FIG. 3).

β-Lap was synthesized, dissolved in DMSO at 47 mmol/L, and concentrations verified after dilution by spectrophotometric assays. Hoechst 33258, hydrogen peroxide ($H_2O_2$), staurosporine, cytochrome c, etoposide, DPQ (3,4-dihydro-5[4-(1-piperindinyl)butoxy]-1(2H)-isoquinoline) and dicoumarol (50) were purchased from Sigma-Aldrich (St. Louis, Mo.).

NQO1 expression was assessed in tumor and 'associated normal' tissues by IHC staining using patient samples obtained and processed by the UT Southwestern Comprehensive Cancer Center Tissue Procurement Shared Resource. Briefly, tissue sections (5 μm) were prepared from fixed paraffin-embedded tissues and baked overnight at 37° C. Endogenous peroxidase activity was eliminated by placing sections in 3% $H_2O_2$ for 20 mins followed by incubation with a-NQO1 antibody (1:500) at 4° C. overnight. Immunodetection was performed using a horseradish peroxidase-based Vecastain Elite ABC Kit (Vector Laboratories, Burlingame, Calif.) according to the manufacture's instructions followed by counterstaining with hematoxylene. Images were taken using a Nikon E400 microscope with a Nikon coolpix 4500 camera.

PC-3, DU145 and LNCaP human prostate cancer cells were originally obtained from Dr. George Wilding (University of Wisconsin-Madison). PC-3 and DU145 cells were grown in RPMI 1640 Medium (Invitrogen, Carlsbad, Calif.) with 5% fetal bovine serum (FBS) and LNCaP cells were grown in Dulbecco's minimal essential medium (DMEM, Invitrogen) with 10% FBS. Cells were cultured at 37° C. in a 5% $CO_2$-95% air humidified atmosphere and were free from mycoplasma contamination.

Disulfide and total glutathione (GSH and GSSG, respectively) levels were determined using a spectrophotometric recycling assay. Following indicated treatments, whole cell homogenates were prepared as described (Reinicke et al., 2005, *Clin Cancer Res.*, 11:3055-64). Data were expressed as % GSSG/total, normalized to protein content using Lowry et al., 1951, *J. Biol. Chem.*, 193:265-75). Shown are means±SE for experiments performed at least three times.

For statistical analyses of IHC, Fisher's exact tests were conducted comparing numbers of NQO1 cases in cancer versus 'adjacent normal' tissue from the same cancer patient.

Example 2

PARP-1 Hyperactivation Mediates β-Lap-Induced Programmed Cell Death

Figure 5:
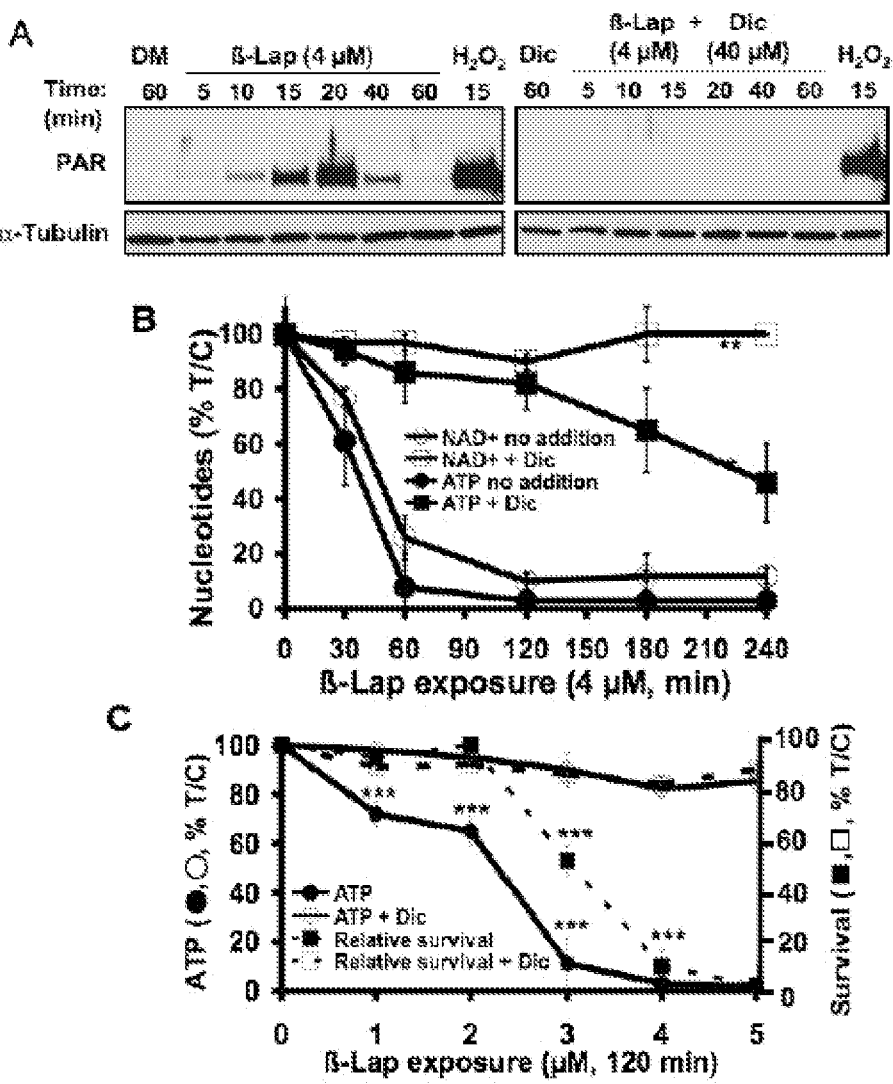
FIG. 5 depicts NQO-1-dependent PPAR-1 hyperactivation, nucleoside depletion and PAR formation were stimulated by β-lap exposure in prostate cancer cells. (a). Western blot analyses of PAR formation in PC-3 cells treated with 4 μM β-lap in the presence or absence of Dic at the indicated times. (b). PC-3 cells were treated as described above in A, and cells harvested at the indicated times were analyzed for NAD+ and ATP levels. Results are means±SE for experiments performed three times in triplicate. (c). ATP depletion and relative survival in β-lap-exposed PC-3 cells treated with various β-lap doses in the presence or absence of DIC (40 μM). Data are means±SE for six replicates from three independent experiments.

Exposure of PC-3 cells with β-lap caused extensive PARP-1 hyperactivation, with significant accumulation of PAR within 10-20 mins that was blocked by dicoumarol (FIG. 4, FIG. 5). Loss of PAR formation in β-lap-treated PC-3 cells noted from 40-60 mins was most likely a function $NAD^+$ substrate depletion (FIG. 4, FIG. 5), as well as the action of PARG. PARP-1 hyperactivation was accompanied by dramatic $NAD^+$ and ATP losses as a function of (i) time (FIG. 5), where metabolite levels were exhausted within 120 min of β-lap exposure; and (ii) dose, where loss of ATP corresponded well with cytotoxicity (FIG. 5). Loss of intracellular nucleotide levels ($NAD^+$ and ATP) and lethality of β-lap-treated PC-3 cells were blocked by dicoumarol (40 μM). Dicoumarol also prevented PARP-1 hyperactivation, $NAD^+$ and ATP losses and cytotoxicity in DU145 cells after β-lap exposure (FIG. 4).

Whole-cell extracts were prepared, proteins separated by SDSPAGE, and Western blots developed using SuperSignal® West Pico Chemiluminescent substrate (Thermo Scientific, Rockford, Ill.), and exposed using Autoradiography Film (Denville Scientific Inc., Metuchen, N.J.). Both PAR (BD Pharmingen, San Jose, Calif.) and γ$H_2AX$ (Upstate, Billerica, Mass.) antibodies were used at 1:2000 and 1:1000 dilutions, respectively. 3-Actin or α-tubulin levels were used as loading control.

Changes in intracellular $NAD^+$ levels were measured (Bentle et al., 2006, *J. Biol. Chem.*, 281:33684-96) and levels were expressed as percent treated divided by control (% T/C)±SE from at least three individual experiments. ATP levels were analyzed from whole-cell extracts using Cell-Titer-Glo Luminescent Cell Viability Assays (Promega, Madison, Wis.) following the manufacture's instructions. Data were graphed as means±SE from at least three independent experiments in triplicates.

Example 3

Figure 7:
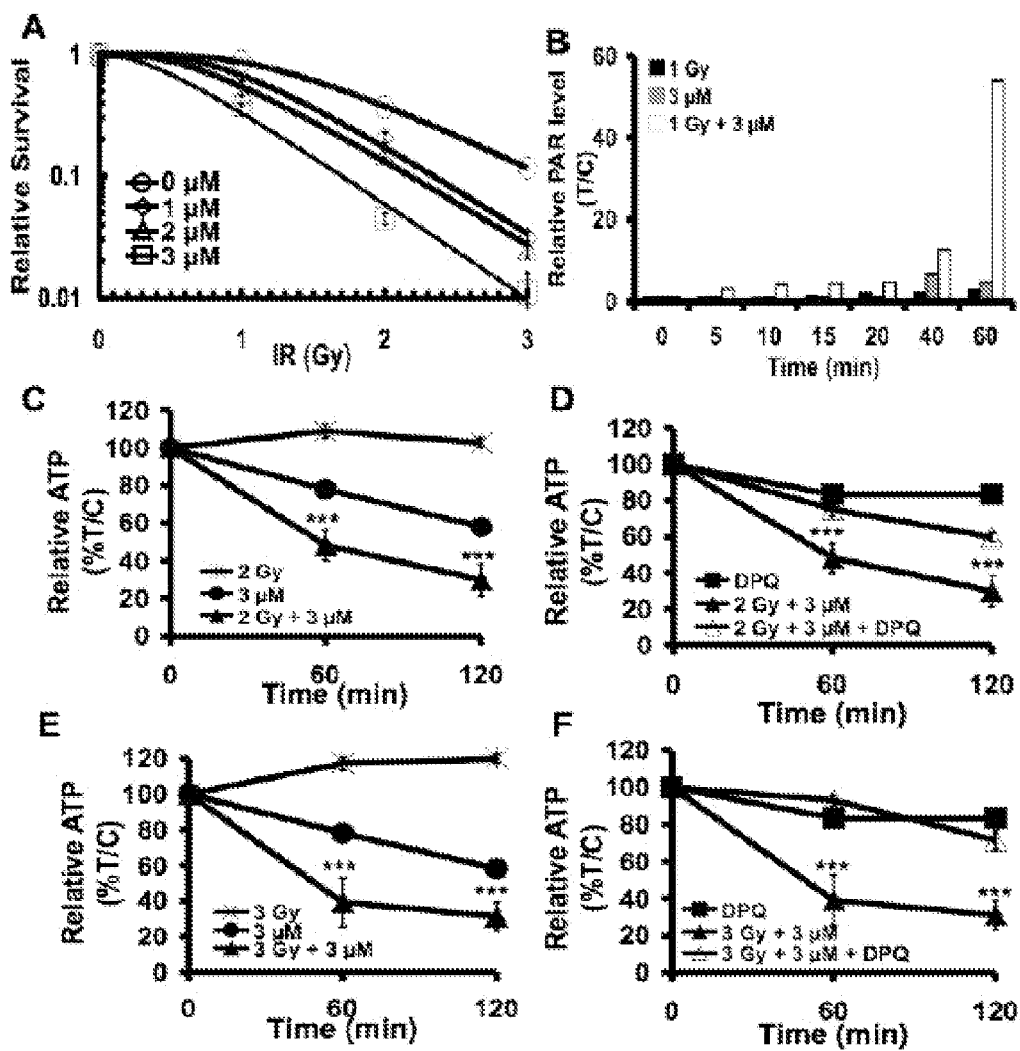
FIG. 7 depicts synergy between IR and β-lap is mediated by PPAR-1 hyperactivation. (a). β-lap exposure sensitized PC-3 cells to IR. Results are means±SE for three independent experiments performed in triplicate. β12>1 (Machado's model). (b). Quantified PAR formation in PC-3 cells after various treatments. (c-f). Synergistic ATP loss observed after IR+β-lap combinations (c and e). DPQ blocked the synergistic ATP depletion effects of IR+β-lap (d and f). Results are means±SE for experiments performed in three times in octuplets. t-tests were performed by comparing each datum point to the corresponding data from single treatments in each graph. ***p<0.001.

Synergy Between IR and β-Lap is Mediated by DNA Damage, Reaching a Threshold for PARP-1 Hyperactivation It was previously reported that the combination of IR and β-lap synergistically killed specific cancer cells, however, the mechanism of synergy was not elucidated. PC-3 cells were treated with single doses of IR (1-3 Gy) followed by exposure to low, non-toxic doses of β-lap (1-3 μM) (FIG. 7). Synergy was noted with all IR and β-lap combinations tested (Tables 1 and 2), corresponding to synergistic increases of PAR levels after combined treatments, but not after single agent exposures.

TABLE 1

Equitoxic doses comparing single to combined treatments in PC-3 cells

| IR (Gy) | β-Lap (μM) | Equivalent dose of IR (Gy) | Equivalent dose of β-Lap (μM) |
|---|---|---|---|
| 0 | 1 | 0.6 | 1 |
| 0 | 2 | 1.2 | 2 |
| 0 | 3 | 1.7 | 3 |
| 1 | 1 | 1.7 | 4.1 |
| 1 | 2 | 2.1 | 5.6 |
| 1 | 3 | 2.7 | 6.8 |
| 2 | 1 | 2.6 | 7.9 |
| 2 | 2 | 3.1 | 9.6 |
| 2 | 3 | 3.6 | 11.5 |
| 3 | 1 | 3.7 | 12.5 |

TABLE 1-continued

Equitoxic doses comparing single to combined treatments in PC-3 cells

| IR (Gy) | β-Lap (μM) | Equivalent dose of IR (Gy) | Equivalent dose of β-Lap (μM) |
|---|---|---|---|
| 3 | 2 | 4.1 | 14.5 |
| 3 | 3 | 4.6 | 16 |

Assessment performed using Machado's model. Values represent doses calculated from means for triplicate experiments from three independent experiments.

TABLE 2

Summary of anti-tumor efficacy studies of IR with or without β-lap-HP-β-CD in vivo[1]

| HPβ-CD-β-Lap (mg/kg) | IR[2] (Gy) | #Mice Tested | Average[3] Tumor Growth Delay (Days) | #Apparently[4] Cured Mice (%) |
|---|---|---|---|---|
| 0 | 0 | 18 | 0 | 0 |
| 10 | 0 | 5 | 0 | 0 |
| 20 | 0 | 5 | 0 | 0 |
| 30 | 0 | 9 | 4 | 2 (22%) |
| 0 | 2 | 13 | 26 | 0 |
| 0 | 3 | 12 | >80 | 8 (67%) |
| 0 | 4 | 5 | >80 | 4 (80%) |
| 0 | 5 | 3 | >80 | 2 (67%) |
| 10 | 2 | 5 | >80[5] | 4 (80%)[5] |
| 20 | 2 | 5 | >80[5] | 5 (100%)[5] |
| 30 | 2 | 5 | >80[5] | 5 (100%)[5] |
| 30 | 3 | 6 | >80 | 6 (100%) |
| 30 | 4 | 5 | >80 | 5 (100%) |

[1]Summary of three independent experiments using 0.20-0.24 kg female athymic mice bearing 300-400 mm³ human PC-3 prostate cancer xenografts with IR alone, HPβ-CD-β-lap alone, or IR with or without HPβ-CD-β-lap treatments as indicated. The above conditions represented different treatment regimens given every other day for a total of 5 treatments. IR was always delivered first followed by β-lap treatments. None of the regimen above caused significant weight loss.
[2]IR was delivered using a focused beam using collimators as described in 'Materials and Methods'.
[3]'Average tumor growth delay' was defined as the time (in days) required for tumor growth to reach an average of 1000 mm³ compared to control, vehicle-treated (HPβ-CD only) mice. The average time for control tumor volumes to reach 1000 mm³ was 14-16 days. Experiments were typically terminated at about 80 days.
[4]An animal was considered 'Apparently cured' if tumors either completely disappeared after treatment or showed significant regression with no significant growth after completion of the regimen above and at the end of 80 days, during which all studies were terminated.
[5]There was no significant difference between regimen where tumors were treated with IR (2 Gy) followed by 10-30 mg/kg HPβ-CD-β-lap.

Figure 6:
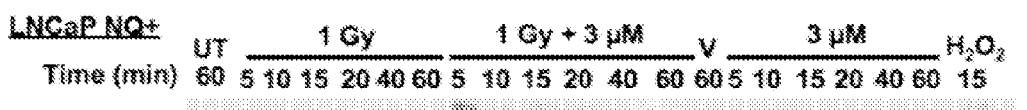
FIG. 6 depicts sublethal doses of IR and β-lap in NQO1+ LNCaP cells cause PPAR-1 hyperactivation and dramatic ATP loss. (a). LNCaP cells expressing or lacking NQO1 were treated with IR+β-lap and monitored for PAR formation. UT, untreated control for IR; V, vehicle; DMSO only. (b). Synergistic ATP loss was noted after IR+β-lap compared to single treatments alone. Results are means±SE for experiments performed three times in duplicate. Student's t-tests compared single to combined treatments. *p<0.001,  p<0.01.
Figure 6:
Figure 6:
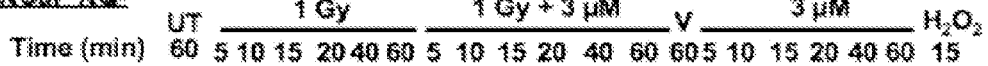
Figure 6:
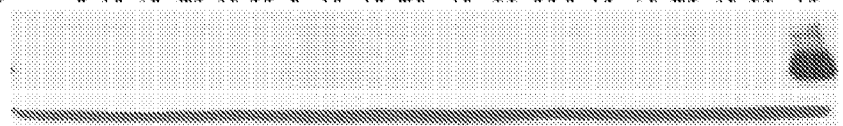
Figure 6:
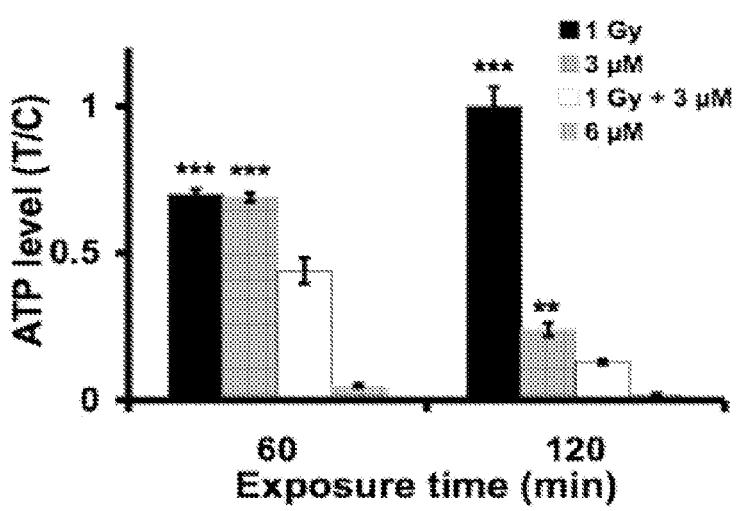

For example, dramatic PAR formation in PC-3 cells treated with 1 Gy+3 μM β-lap was noted at 60 mins, with no apparent levels in cells after each agent alone. Similar responses were noted using NQO1-expressing LNCaP and DU145 cells, but not in genetically matched NQO1-LNCaP cells (FIG. 6). Synergy was prevented by dicoumarol in NQO1-expressing prostate cancer cells and corresponded to the formation of DNA lesions (noted by alkaline comet and γH2AX foci formation) that presumably reached threshold levels required for PARP-1 hyperactivation (FIG. 6). Synergy between IR and β-lap in PC-3 cells was accompanied by dramatic losses of ATP (see FIGS. 4C-D for synergy between 2 or 3 Gy and 3 μM β-lap) and NAD+ (not shown). Importantly, synergistic losses of ATP in PC-3 cells following 2 or 3 Gy+3 μM β-lap were prevented by pre- and co-treating cells with DPQ, a specific PARP-1 inhibitor (FIG. 7) that also prevented β-lap-induced cell death alone in various endogenously over-expressing NQO1 cancer cells. Synergy between IR and β-lap was not observed in NQO1-LNCaP cells (FIG. 6).

Relative DNA cell survival assays were assessed after various treatments. Briefly, cells were seeded at 5×103 per well in 48-well plates and allowed to attach overnight. Cells were then mock-treated or treated with various doses of β-lap (for 2 h) in the presence or absence of dicoumoral as indicated. Drug-free medium was then added and cells allowed to grow for 5-7 days until control cells reached ~100% confluence. DNA content was then determined by Hoeschst 33258 dye staining and fluorescence detection using a plate reader (Perkin-Elmer, Boston, Mass.) as described. Relative survival assays after combined treatment were confirmed by colony-forming ability assays as described. Results were reported as means±SE from at least three independent experiments.

For relative survival data, different combinations of IR+β-lap exposures were fit with simple multi-target models in SigmaPlot for Windows Version 11.0. For synergy, a statistical definition of synergy (48) was used and calculations were performed by fitting experimental data with the Machado and Robinson model using the R code (47). The equitoxic doses listed in Table 1 were calculated by the parameters of the model of Machado and Robinson obtained in fitting.

Example 4

Figure 8:
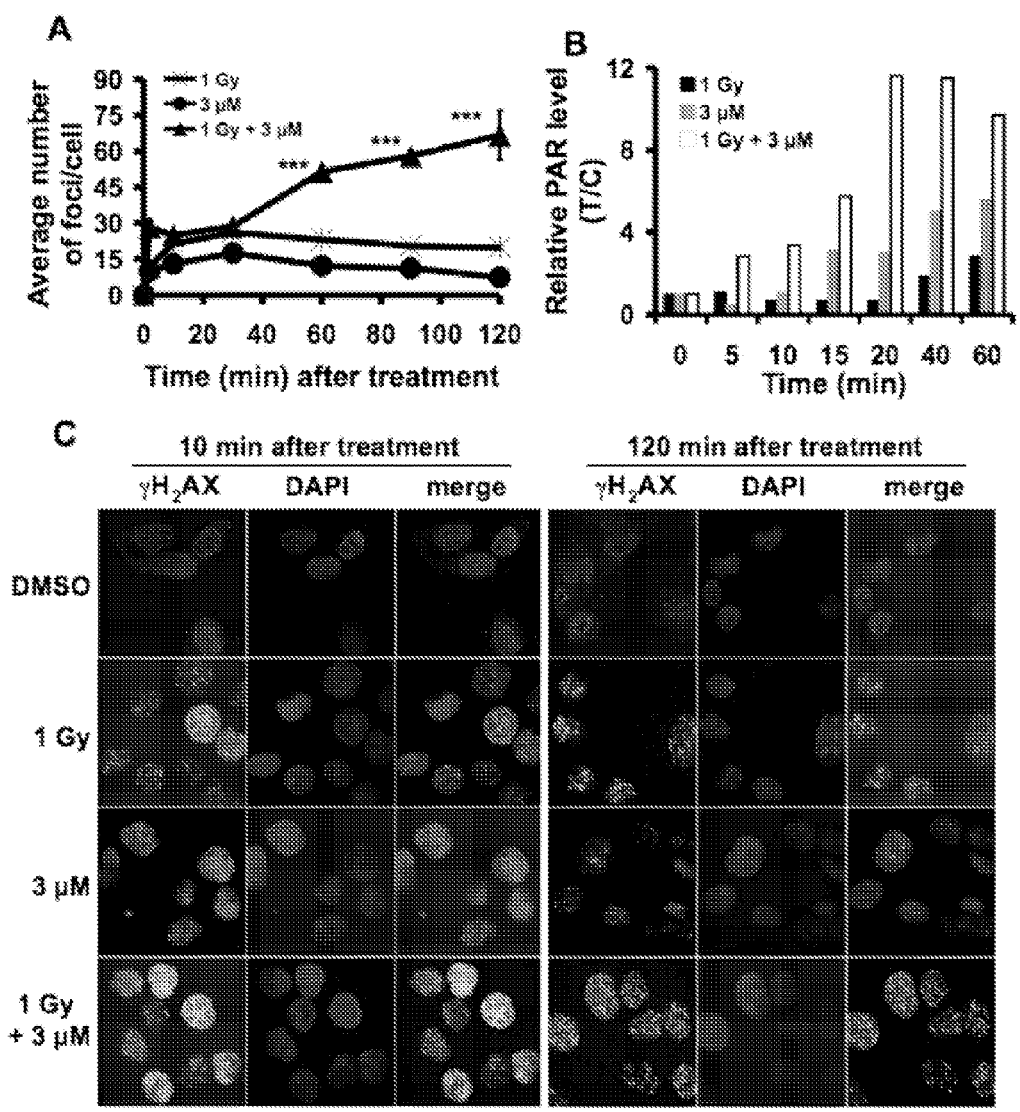
FIG. 8 depicts combination of sublethal β-lap and IR doses enhances PAR and $\gamma H_2 AX$ foci formation in DU145 cells. (a). $\gamma H_2 AX$ foci formation assessed. (b). Par formation quantified. Results are means±SE from 60 cells. Student's t-tests were performed by comparing combined to single treatment. ***p<0.001. (c). Confocal imaging of $\gamma H_2 AX$ foci formation at 10 and 120 min in DI145 cells treated as indicated.
Figure 9:
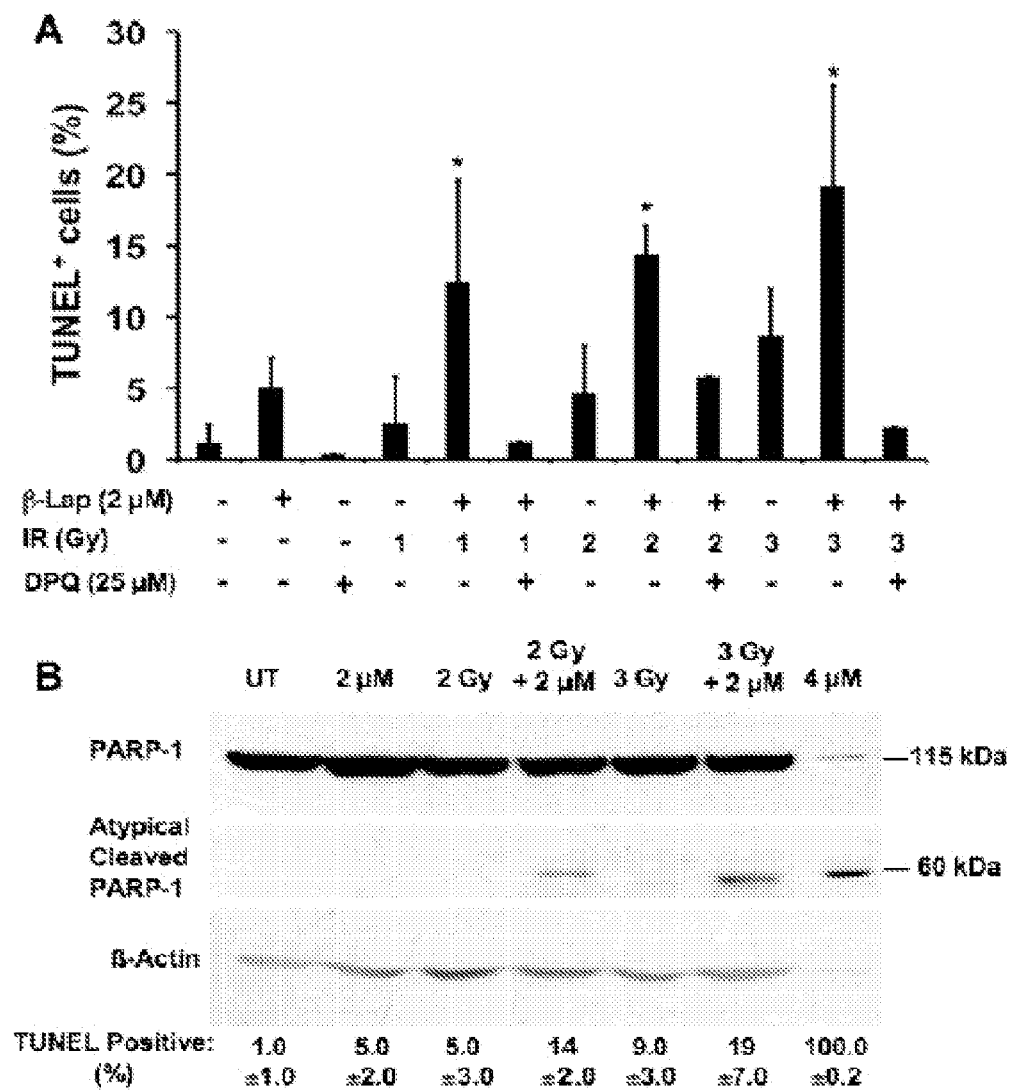
FIG. 9 depicts Combined treatment with sublethal doses of IR and β-lap promotes apoptosis and atypical PPAR-1 cleavage. (a). PC-3 cells were exposed to the indicated treatments for 2 hours, whole cell extracts prepared at 72 hours and apoptosis monitored by TUNEL reactions. Results were means±SE from three independent experiments. Statistical differences between combined and single treatment regimen were indicated as *p<0.05. DPQ blocked apoptosis in all combination treatments (p<0.01). (b). PC-3 cells were treated as in A, above as indicated for 2 hours and harvested at 48 hours for Western blot analyses. A lethal β-lap dose of 4 uM was used as positive control to indicate the 60 kDa atypical cleaved PPAR-1. TUNEL assay data were means±SE from three independent experiments. UT: untreated.

Synergy Between IR and β-Lap Exposures Involves Atypical PARP-1 Cleavage, and TUNEL+ Programmed Necrosis Loss of survival as a result of β-lap treatment correlates well with TUNEL+apoptotic responses. Synergistic cytotoxic responses of NQO1-expressing PC-3 cells after IR+β-lap treatments (FIGS. 7 and 9) were confirmed by analyzing apoptosis (FIGS. 8 and 9). Treatment of PC-3 cells with 1-3 Gy, each in combination with 2 μM β-lap, resulted in significant increases in apoptotic cells within 72 h (FIG. 9), corresponding directly to loss of colony forming ability (FIG. 5). Indeed, all combination therapies of IR with β-lap (Table 1) reveal synergy at these low doses of each agent.

Figure 10:
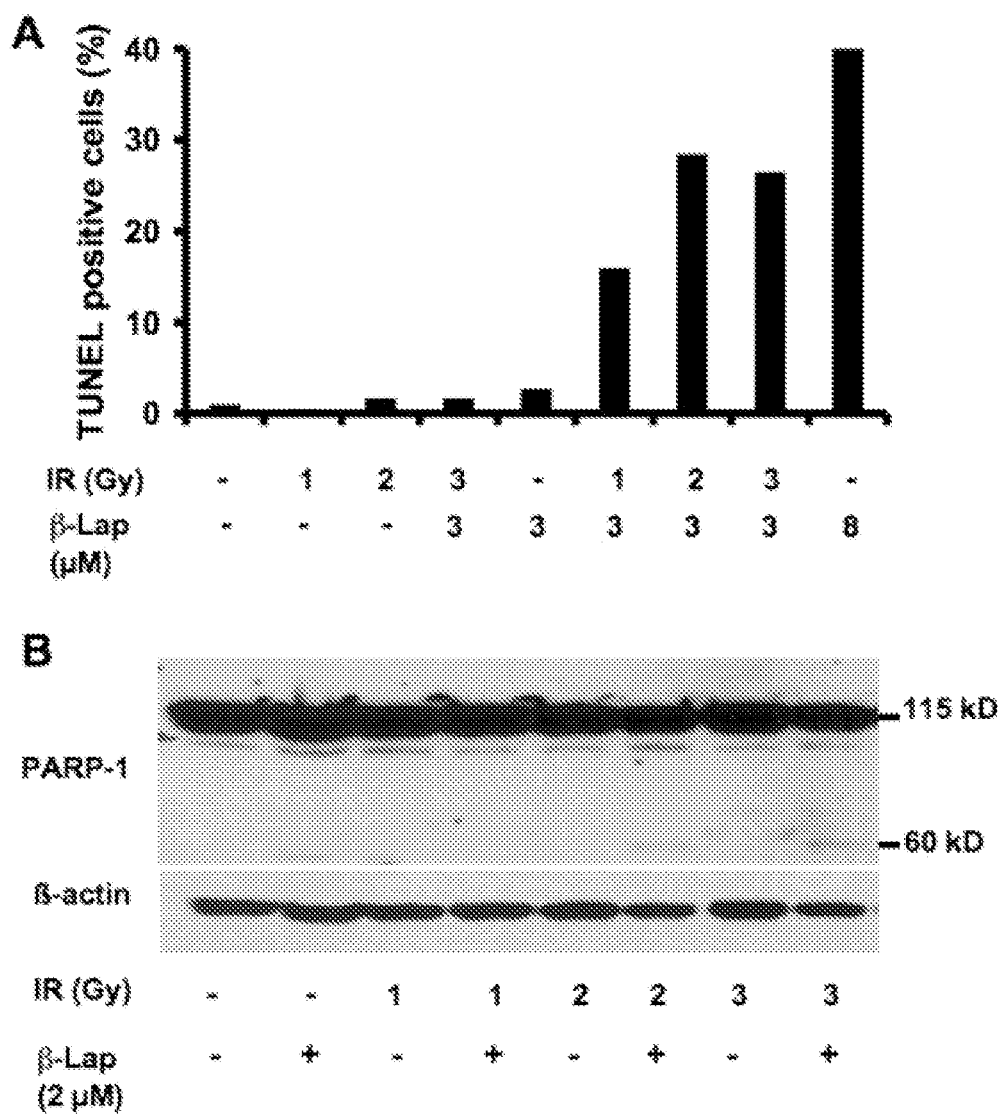
FIG. 10 depicts treatment of NQ+LNCaP cells with sublethal doses of IR and β-lap promotes atypical PPAR-1 cleavage and apoptosis. (a). NQO1+LNCaP cells exposed with various combination and single agent treatments as indicated. (b). Cells were exposed to different treatment for 2 hours as indicated and assessed for PPAR-1 atypical cleavage 48 hours post-treatment.

For example, treatment of PC-3 cells with nonlethal agents (alone) in combination with IR (i.e., 1 Gy+1 μM β-lap), was the same as treating cells with a lethal dose of 4 μM β-lap. Similar responses were noted in LNCaP cells expressing exogenous NQO1, in which synergistic levels of apoptosis and atypical PARP-1 cleavage at 72 h post-treatment were noted (FIG. 10). Synergy between IR and β-lap was prevented by dicoumarol, and not observed in NQO1-LNCaP cells. In contrast, different low doses of IR alone (i.e., 1-3 Gy) only led to 2±2%, 5±3% and 9±3% apoptosis, respectively. Similarly, a low sublethal dose of 2 μM β-lap in NQO1-expressing PC-3 cells resulted in minimal apoptosis (i.e., 5±2%, FIG. 9).

Cell death caused by a lethal dose of β-lap to prostate cancer cells with endogenous elevation of NQO1 involves activation of μ-calpain and atypical cleavage of PARP-1, as noted after 4 μM β-lap treatment (FIG. 9B, lane 7). Similarly, exposure of PC-3 cells with IR+β-lap involved synergistic apoptotic responses, above the additive levels of IR or β-lap alone. Atypical PARP-1 cleavage (i.e., formation of an ~60 kDa PARP-1 fragment) in combination-treated cells was noted (FIG. 5B), resulting from activation and nuclear translocation of μ-calpain. Similar atypical PARP-1 cleavage events accompanied IR+β-lap synergy in NQO1+LNCaP cells (FIG. 10).

γH$_2$AX foci formation was detected using an anti-γ-H$_2$AX antibody (Upstate, Billerica, Mass.) overnight at 4° C. at 1:500 dilution. AlexaFluor™ fluorescent secondary antibodies (Molecular Probes, Carlsbad, Calif.) were added for 2 h at room temperature. Nuclei were stained by DAPI and confocal images collected using a NIKON Confocal microscope.

Apoptosis was quantified using ApoDirect™ (TUNEL) assays from BD Pharmingen as described (Bey et al., 2007, *Proc. Natl. Acad. Sci. USA*, 104:11832-837). Samples were analyzed by using FC-500 flow cytometer (Beckman Coulter Electronics, Brea, Calif.) and Elite acquisition software. Data were expressed as means±SE from three independent experiments.

Example 5

Efficacy In Vivo of the Combination of IR and β-Lap

Figure 11:
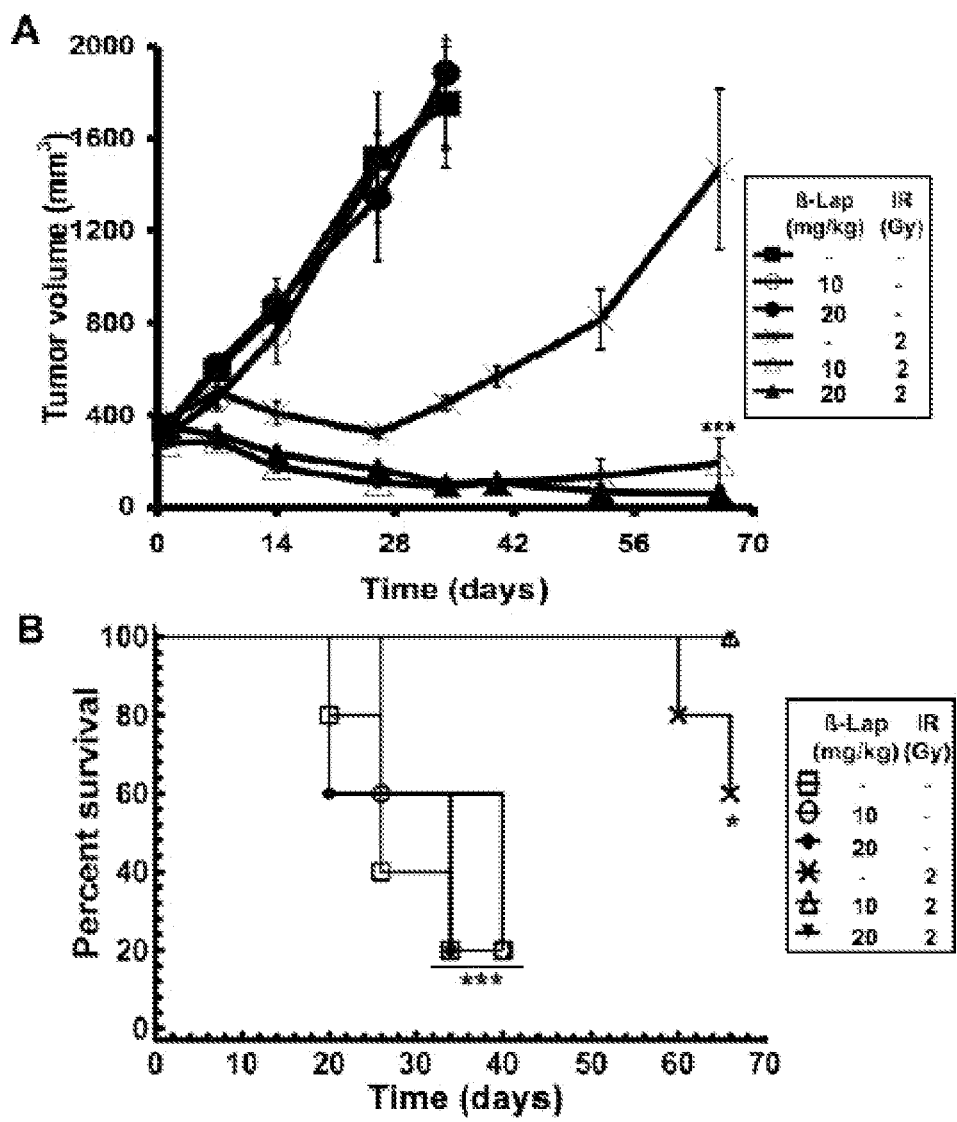
FIG. 11 depicts IR and β-lap cause synergistic antitumor activity in PC-3 tumor xenografts. (a). Anti-tumor efficacy using different treatment regimen in PC-3 xenografts. Treatments were given to mice bearing 350 $mm^3$ tumors once every other day starting on day one, for five treatments. Results are means±SE. Mixed Model analyses showed *p<0.0001 for combined vs. single treatments, including untreated controls. (b). Kaplan-Meier survival curves reflect significantly enhanced antitumor efficacy using various treatment regimen, *p<0.001, **p<0.05. Log-rank p-values represent significant indices of each single versus combined treatments. Endpoints represent % survival of mice over time.
Figure 12:
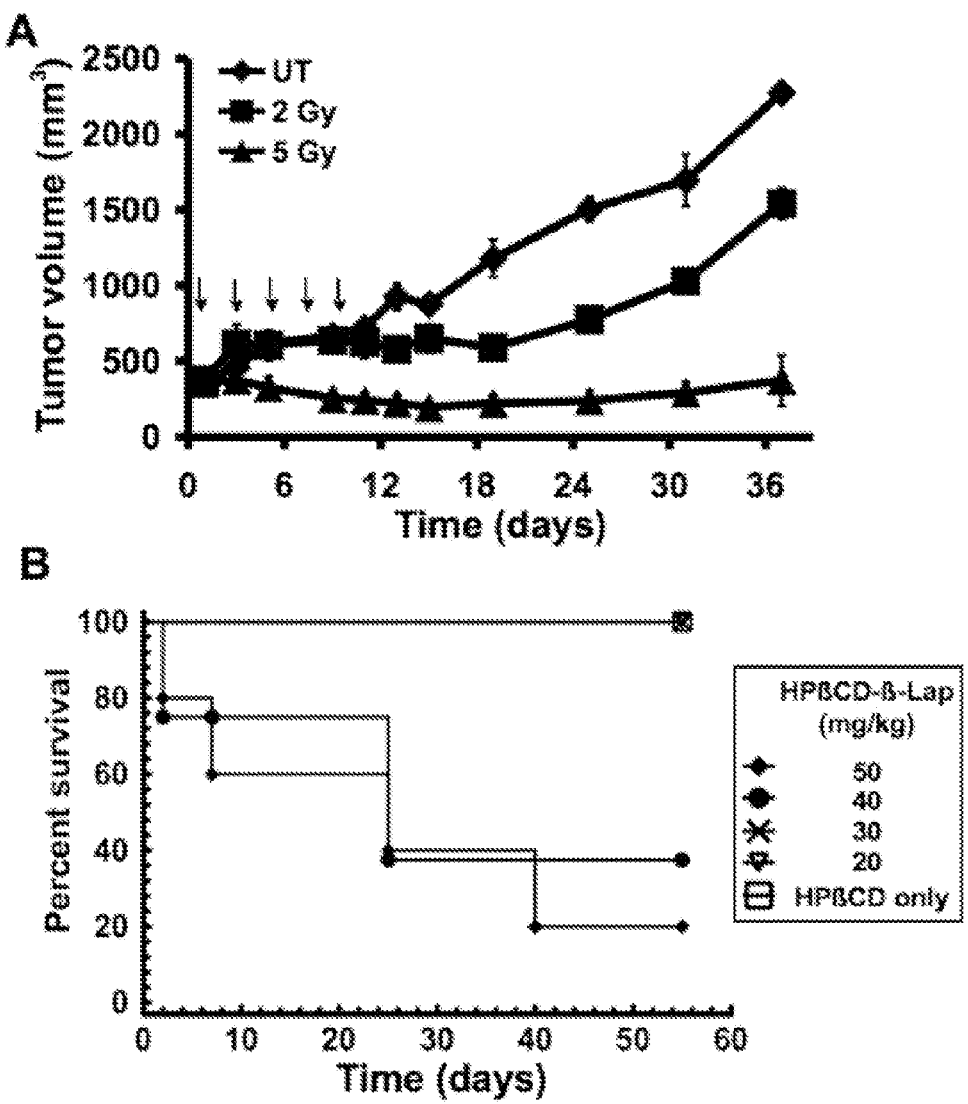
FIG. 12 depicts antitumor efficacy in mice bearing NQO1+PC-3 xenografts after IR compared to β-lap as single regimen. (a). Tumor growth in NQO1+PC-3 xenografts after fractionated (5 doses, every other day) IR (2 Gy or 5 Gy)

To date, efficacy of β-lap against human prostate cancer xenografts expressing elevated levels of endogenous NQO1 has not been demonstrated. Using the β-lap in hydroxypropyl-β-cyclodextrin (HPβCD) formulation, the inventors demonstrated significant efficacy of HPβCD-β-lap when administered at 10 or 20 mg/kg in combination with 2 Gy fractions of IR (FIG. 11). Mice (5/group) bearing PC-3 xenografts with an average tumor volume of ~350 mm³ were exposed to five doses of IR alone, HPβCD-β-lap alone, or IR+HPβCD-β-lap combinations every other day between days 1-9. Treatment of mice with HPβCD-β-lap at 10 or 20 mg/kg exhibited no antitumor efficacy, nor morbidity or mortality. Although mice treated with 2 Gy fractions (five treatments, every other day) resulted in significant tumor growth delay (ave: 26 days, FIG. 11, Table 1), combinations of IR (2 Gy) with 10 or 20 mg/kg HPβCD-β-lap resulted in significant tumor regression beyond additivity from IR or HPβCD-β-lap treatments alone. Ninety percent (9/10) of animals exposed to IR+10 or 20 mg/kg HPβCD-β-lap were 'apparently cured', showing no further tumor growth up to 150 days (FIG. 11, Table 1). In contrast, 90% of PC-3-bearing mice treated with HPβCD-β-lap alone (10 or 20 mg/kg) died within 40 days, similar to vehicle (HPβCD) alone control mice. Mice treated with IR (2 Gy) alone demonstrated an obvious delay in tumor growth (FIG. 11), however, all mice eventually died (were sacrificed with tumor volumes were >10% weight). Finally, although mice treated with 2 Gy+30 mg/kg HPβCD-β-lap resulted in statistically equivalent tumor growth delay and 'apparent cures' (Table 1), the inventors noted that the dose was close to the drug's maximum tolerated dose (MTD) of ~35 mg/kg. Collectively, the inventors treated 15 mice (3×5 mice/group) with 2 Gy+10-30 mg/kg HPβCD-β-lap, noting dramatic synergistic responses, statistically superior (p<0.001) to 2 Gy alone or HPβCD-β-lap alone (10-30 mg/kg) regimen (Table 1). A representative experiment of these data are presented in FIG. 11.

Example 6

Radiosensitization NSCLC Tumors by β-Lap Occurs by PARP1 Hyperactivation

As in NQO1 overexpressing prostate cancer cells, NQO1 bioactivatable drugs, such as β-lap, can radiosensitize nonsmall cell lung cancer (NSCLC) cells and tumors in vitro and in vivo. Athymic mice bearing NSCLC xenografts were irradiated with 4 Gy and treated with 30 mg/kg β-lap-HPβCD vs IR or β-lap alone iv once every other day for a total of 5 treatments in one regimen as indicated. Results from one regimen of therapy are shown (FIG. 13). Significant antitumor activity and effective reduction and cures (~40% of animals) were noted. Kaplan-Meyer survival curves of these mice treatment with 4 Gy+30 mg/kg are shown in FIG. 13).

Mechanistically, β-lap-mediated radiosensitization occurs by PARP1 hyperactivation as noted in NQO1 over-expressing human prostate cancer cells. β-Lap exposure of NQO1+ A549 cells results in hyperactivation of PARP1 as seen by PAR formation (FIG. 14). Note that DSB formation, measured by γH2AX and phosphoSer$^{981}$-ATM was significantly delayed in β-lap-treated cells and occurred after PAR formation decreased. Analyses of phospho-Thr$^{2609}$-DNA-PKcs formation after β-lap in dose and time manners further demonstrated the delayed DSB formation. Inhibiting PARP1 activity by addition of 25 mM 3-aminobenzamide, a PARP1 inhibitor, spares and delays PAR formation in A549 NSCLC cells (FIG. 14). Radiosensitization of A549 and NQO1+ H596 NSCLC cells by β-lap are demonstrated (FIG. 14). PAR formation in A549 NSCLC cells treated with 1 Gy+2 µM β-lap, but not in cells treated with either agent alone, was noted (FIG. 14). Induction of NQO1 protein levels was not required for radiosensitization of A549 NSCLC cells, since NQO1 levels (protein and enzyme levels) were not significantly altered after IR exposure of A549 NSCLC cells (FIG. 14). Yet, addition of dicoumarol, an NQO1 inhibitor, spared radiosensitization of A549 cells (FIG. 14). Thus, NQO1 activity, but not its induction, is required for β-lap-mediated radiosensitization.

Whole-cell extracts were prepared, proteins separated by SDSPAGE, and Western blots developed using SuperSignal® West Pico Chemiluminescent substrate (Thermo Scientific, Rockford, Ill.), and exposed using Autoradiography Film (Denville Scientific Inc., Metuchen, N.J.). An anti-human NQO1 antibody was kindly provided to us by Dr. David Ross (University of Colorado Health Science Center, Denver, Colo.) and used at a 1:5000 dilution overnight at 4° C.

Athymic nu/nu mice were purchased from Charles River Laboratories International, Inc (Wilmington, Mass.). All animals were housed in a pathogen-free facility with 24-h access to food and water. Experimental protocols were approved by the institutional Animal Care and Use Committee at the University of Texas Southwestern. PC3 cells (5×106) were subcutaneously injected into the right thighs of athymic nude mice and tumor volumes were allowed to reach ~350 mm³. Mice (5 mice/group) were then randomly grouped with no statistical differences in tumor sizes among the six groups. Mice were then mock-treated or exposed to various IR doses followed immediately by treatment with various doses (10-30 mg/kg) of HPβCD-β-lap or HPβCD. When used, various doses of IR were given locally first, to tumor sites with whole-body shielded. Mice were exposed to one treatment regimen, consisting of mock or XRT, immediately followed by HPβCD alone or various HPβCD-β-lap doses administered via tail vein injections for five IR+β-lap exposures. Tumor volumes were measured by caliper (length×width×width/2) every other day. Mice were sacrificed when tumors reached 2 cm³ or 10% total body weight.

Regression analyses of tumor growth profiles in vivo in six tested groups were analyzed using a mixed model approach with AR correlation structures. Log-rank tests were applied to survival analyses (Kaplan-Meier curves). In general, two-sided p values of ≤0.05 were considered significant. All statistical analyses were performed using SAS 9.1 Service Pack 4.

Example 7

Tissue NQO1 Staining

NQO1 expression is assessed in tumor and associated normal tissue by IHC staining, RT-PCR and by enzymatic activities. Briefly, 5-μm tissue sections will be prepared from fixed paraffin-embedded tissues and baked overnight at 37° C. Endogenous peroxidase activity is eliminated by placing sections in 3% $H_2O_2$ followed by incubation with anti-human NQO1 antibody used at 1:500 at 4° C. overnight. Immunodetection is performed using a horseradish peroxidase-based Vecastain Elite ABC Kit (Vector Laboratories, Burlingame, Calif.) followed by counterstaining with hematoxylin. Sections are visualized with 3,3'-diaminobenzidine and hematoxylin counterstain. Ten (10) high power fields (×400) are examined to determine average NQO1 staining intensity, which is reported on a continuous scale. IHC assays are performed in duplicate and assessed by the Simmons Cancer Center Histology Core.

DNA lesions, including total base damage, DSBs and SSBs, versus DSBs were assessed using single-cell gel electrophoretic comet assays under alkaline or neutral conditions, respectively (TREVIGEN, Gaithersburg, Md.). Slides were stained with SYBR Green and visualized using a Nikon Eclipse TE2000-E fluorescence microscope (Melville, N.Y.). Digital photomicrographs were taken and comet tail lengths quantified using NIH Image J software. Each datum point represents an average of 100 cells±SE, and data are representative of experiments performed in triplicate.

Example 8

PBMC NQO1 and Catalase Activities

On Cycle 1, Days 1 and 15, 15 cc of blood will be collected in Becton Dickinson sodium heparin polymer gel tubes at the following time points: pre-ARQ 761 infusion, 4 h after infusion, and 24 h after infusion. Selection of these time points coincides with PK draws (the same tube will be used for both purposes) and is based on preclinical observations of NQO1 induction by β-lap. Tubes will be centrifuged, and the PBMC pellet will be divided into two ependorf tubes, stored at −70° C., batched, and delivered to the Boothman laboratory. NQO1 and catalase enzyme assays will be performed as described.[5] Briefly, in reaction medium containing cytochrome c and bovine serum albumin in Tris-HCl buffer, NQO1 activities are measured using NADH as the immediate electron donor and menadione as the intermediate electron acceptor. Assays will be repeated in the presence of dicoumarol (DIC) (an NQO1 inhibitor), and activity inhibited by DIC will be attributed to NQO1. Enzyme activity will be calculated as DIC-inhibited nanomoles of cytochrome c reduced/min/mg protein expressed based on initial rates of OD change at 550 nm and an extinction coefficient for cytochrome c of 21.2 mM/cm. Catalase levels are also assessed as described below.

Example 9

NQO1 Polymorphisms

NQO1*2/*2 and *3/*3 polymorphisms will be detected from NQO1 *1/*1 wild-type sequences by PCR-RFLP. Genomic DNA is extracted from blood PBMC and tumor tissue (when feasible) using Qiagen spin columns. Assessing NQO1 levels in blood and tumor tissue allows us to assess whether changes in NQO1 levels in tumors occur in wild-type patients, an assessment not performed to date. Using previously described oligonucleotide primers, PCR products will undergo gel electrophoresis. Final genotyping is determined based on the size and pattern of separated bands diagnostic for *1/*1 (wild-type), or polymorphic *2/*2 or *3/*3 NQO1 polymorphisms.

Example 10

Statistical Analyses

For tissue NQO1 expression, specimen scores are summarized in tables and figures. Logistic regression is used to assess the association between IHC score and NQO1 bioactivatable drug response and a Cox regression model is used to assess the association between IHC score and survival (progression free and overall) times. For PBMC NQO1 activity, baseline and post-treatment NQO1 activity are summarized in tables and figures. Scatter plots are used to monitor NQO1 changes for each patient over time. The linear (or generalized linear) regression model is used to assess the correlation between NQO1 changes, plasma drug levels, and clinical endpoints. Expression changes of all biomarkers are summarized in a table. A power calculation analysis is used for association between NQO1 expression and clinical efficacy. For example, a 0.05 two-sided Fisher's z test of the null hypothesis that the Pearson correlation coefficient is 0.5, will have 81% power to detect a correlation coefficient of 0.8 when the sample size is 30.

Example 11

Catalase Protection Against Tumor Selective Programmed Necrosis Mediated by NQO1-Dependent Reactive Oxygen Species and PARP1 Hyperactivation 1. β-Lapachone-Induced Cell Death is NQO1-Dependent, Consumes Oxygen, and is Not Inhibited at Low Dose NAC
   Materials and Methods
   Chemicals, Reagents and Antibodies:
   β-Lap (3,4-dihydro-2,2-dimethyl-2H-naphtho[1,2-b]pyran-5,6-dione) was synthesized by William G. Bornmann (M.D. Anderson), confirmed by NMR, dissolved in DMSO at 40 mM, and concentrations verified by spectrophotometry (Pink et al., *J Biol. Chem.* 2000; 275:5416-24). Menadione was obtained from Sigma-Aldrich (St. Louis, Mo.) and dissolved in DMSO. Dicoumarol (Sigma-Aldrich) was used as described (Pink et al., *J Biol. Chem.* 2000; 275:5416-24). N-acetyl-L-cysteine (NAC) (Sigma-Aldrich) was used at 5 mM for 24 h pre-treatments and 2 h co-treatments as described (Reinicke et al., *Clin Cancer Res.* 2005; 11:3055-64). Monobasic ($KH_2PO_4$) and dibasic ($K_2PO_4$) potassium phosphate and sodium cyanide (NaCN), were obtained from Fisher Scientific (Pittsburgh, Pa.) and used as described (Zhao et al., *Cancer Res.* 2001; 61:5537-43). Xanthine, nitroblue tetrazolium (NBT), diethylenetriaminepentaacetic acid (DETAPAC), catalase, SOD, bovine serum albumin (BSA), bathocuproine disulfonic acid (BCS) disodium salt hydrate, and xanthine oxidase (Sigma-Aldrich) were used as described (Zhao et al., *Cancer Res.* 2001; 61:5537-43). Anti-PAR and anti-gama-H2AX were used as described (Bentle et al., *J Biol. Chem.* 2006; 281:33684-96) and polyclonal anti-AIF (Santa Cruz) was diluted 1:1000 or 1:100 for western-blots and IHC, respectively.

Mammalian Cell Culture, Treatments and Survival Assays:

MDA-MB-231 cells lacking or expressing NQO1 and MCF-7:WS8 (MCF-7) cells were grown as described (Pink et al., *J Biol. Chem.* 2000; 275:5416-24; Bentle et al., *J Biol. Chem.* 2006; 281:33684-96). All cells were grown in RPMI 1640 media at 37° C. in a humidified incubator with a 5% $CO_2$-95% air atmosphere. All cells were free of mycoplasma.

Oxygen Consumption Analyses:

Oxygen consumption was measured using an Ocean Optics, Inc. (Dunedin, Fla.) Foxy-18G-AF oxygen sensor using S9 supernatants (Pink et al., *J Biol. Chem.* 2000; 275:5416-24) as previously published (Zhao et al., *Cancer Res.* 2001; 61:5537-43). S9 extracts were added to a 37° C. closed system containing Tris-HCl buffer (50 mM, 10% BSA, pH 7.5, 0.5 mM NADH, β-lap±50 μM dicoumarol as indicated (Zhao et al., *Cancer Res.* 2001; 61:5537-43). The OOISensors program (Ocean Optics, Inc.) was used to quantify fluorescence at 599.62 nm every 512 seconds, averaging every four readings. Data (means, ±SEM) were graphed as X-fold rate of $O_2$ consumption from three independent experiments, each performed in triplicate. MCF-7 cells were treated with varying doses of β-lap for 2 minutes in a closed system to determine moles of dissolved oxygen lost (Polagraphy) or consumed (Clark electrode). Hydrogen cyanide (HCN) was added to the closed system to demonstrate oxygen utilization via cellular respiration. Dicoumarol (50 μM) an NQO1 inhibitor, was added to the closed system containing β-lap and MCF-7 cells to demonstrate that oxygen consumption in these cells was NQO1 dependent.

ROS, NAD+ and ATP Measurements:

Cellular oxidative stress was assessed by GSSG content (Bentle et al., *J Biol. Chem.* 2006; 281:33684-96). All biochemical determinations were normalized to protein content (Lowry et al., *J Biol. Chem.* 1951; 193:265-75). Experiments were performed three times and data expressed as means, ±SEM. Changes in intracellular $NAD^+$ levels were measured as described (Bentle et al., *J Biol. Chem.* 2006; 281:33684-96). Data were expressed as $NAD^+$ (% treated/control) means, ±SEM for experiments performed three times in triplicate.

Enzyme Assays:

Enzyme assays were performed as previously described by Pink et al., *J Biol. Chem.* 2000, 275:5416-24. S9 Supernatants were prepared from cells in mid-log to late log phase growth. Cells were harvested by trypsinization (0.25% trypsin and 1 mM EDTA), washed twice in ice-cold, phenol red-free Hank's balanced salt solution, and then resuspended in a small volume of PBS, pH 7.2, containing 10 g/μL aprotinin. The cell suspensions were sonicated on ice four times, using 10-s pulses, and then centrifuged at 14,000×g for 20 min. The S9 supernatants were aliquoted into microcentrifuge tubes and stored at −80° C. until used. A 1× protease inhibitor cocktail was added to prevent enzyme activity degradation. NQO1 activity was detected by monitoring the change in absorbance of cytochrome-c in the presence or absence of dicoumarol. Menadione was used as the electron acceptor. NADH was used as the electron donor.

NQO1 Standard Enzyme Assay Using Menadione as the Electron Acceptor, as Well as Assessment of Two One-Electron Oxidoreductase Enzymes:

Three enzymes are routinely assayed as described by Fitzsimmons et al., 1996, *J. Natl. Cancer Inst.,* 88, 259-269 and Gustafson et al., 1996, *Mol. Pharmacol.* 50, 728-735. Reaction medium contained 77 μM cytochrome c (practical grade; Sigma) and 0.14% bovine serum albumin in Tris-HCl buffer (50 mM, pH 7.5). NQO1 activity was measured using NADH (200 μM) as the immediate electron donor and menadione (10 μM) as the intermediate electron acceptor. Each assay was repeated in the presence of 10 μM dicoumarol, and activity attributed to NQO1 was that inhibited by dicoumarol (Hollander et al., 1975, *Arch. Biochem. Biophys.* 169, 568-576). NADH: cytochrome b5 reductase was measured using NADH (200 μM) as the electron donor, and NADH:cytochrome P-450 reductase was measured using NADPH (200 μM) as electron donor (45) in a Beckman DU 640 spectrophotometer (Beckman Coulter, Fullerton, Calif.). Reactions were carried out at 37° C. and were initiated by the addition of S9 supernatants. Varying amounts of supernatants, from 10 to 40 μL, were used to ensure linearity of rates with protein concentration. Enzyme activities were calculated as nmol of cytochrome c reduced/min/μg of protein, based on the initial rate of change in OD at 550 nm and an extinction coefficient for cytochrome c of 21.1 mM/cm. Results shown are the average enzyme activity for three separate cell extractions±S.D. or both values from duplicate experiments.

NADH Recycling Assays

Assays were performed with either purified NQO1 or S9 extracts from MCF-7:WS8, or other cancer or normal cells. For the assay using purified NQO1, 1.50 g of recombinant human NQO1 was mixed with 200-500 μM NADH in 50 mM potassium phosphate buffer, pH 7.0. Reactions were initiated by the addition of 2-20 μM β-lap or menadione, and the change in absorbance at 340 nM was measured over time. For assays using MCF-7:WS8 S9 extracts, 50 1 of extracts containing approximately 2000 units of NQO1/mg of protein were mixed with 200-500 μM NADH in 50 mM Tris-HCl, pH 7.5, containing 0.14% bovine serum albumin. Reactions were initiated by the addition of 5-200 μM β-lap or menadione, and change in absorbance at 340 nM was measured for 10 min. All reactions were also performed in the presence of 10 μM dicoumarol, which inhibited all measurable NQO1 activity.

Results

The proposed NQO1-driven futile cycle of β-lap (FIG. 28A) (Pink et al., *J Biol. Chem.* 2000; 275:5416-24) predicted an accelerated rate of oxygen ($O_2$) consumption with concomitant production of superoxide ($O_2.^-$) and hydrogen peroxide ($H_2O_2$). Using triple negative (Her2−, PR−, ER−) MDA-MB-231 breast cancer cells expressing (231-NQ+) or lacking (231-NQ−) NQO1, $O_2$ consumption was directly measured in a closed system with an Ocean Optics $O_2$ sensor (FIG. 28B). Appropriate controls using KCN and oligomycin were performed (FIG. 29). NADH, NQO1 enzymatic activity and β-lap were necessary components for robust futile cycling and subsequent $O_2$ consumption, since dicoumarol prevented dose-dependent, β-lap-induced $O_2$ consumption noted in 231-NQ+, but not in 231-NQ− cells (FIG. 28B; also Table 3 for other breast cancer cell lines).

TABLE 3

NQO1 activity for breast cancer cell lines was measured as dicoumarol inhibitable reduction of cytochrome-c/μg protein/min. $LD_{50}s$ for breast cancer cells treated with β-lap +/−1000 U catalase or 50 μM dicoumarol were obtained by long term survival assays as described below.

| Cell Line | NQO1 activity nMoles/min/ug | $LD_{50}$ β-Lap | $LD_{50}$ β-Lap + CAT | $LD_{50}$ p-Lap + DIC |
|---|---|---|---|---|
| HCC1937 | 1800 +/− 100 | 2.2 | 3.4 | 5.0 |
| HTB122 | 1030 +/− 60 | 1.5 | 2.8 | 5.5 |
| ZR751 | 770 +/− 20 | 1.4 | 3.2 | 6.8 |

TABLE 3-continued

NQO1 activity for breast cancer cell lines was measured as dicoumarol inhibitable reduction of cytochrome-c/μg protein/min. LD$_{50}$s for breast cancer cells treated with β-lap +/−1000 U catalase or 50 μM dicoumarol were obtained by long term survival assays as described below.

| Cell Line | NQO1 activity nMoles/min/ug | LD$_{50}$ β-Lap | LD$_{50}$ β-Lap + CAT | LD$_{50}$ p-Lap + DIC |
|---|---|---|---|---|
| H2185 | 210 +/− 15 | 1.3 | 2.6 | 6.4 |
| HTB24 | 110 +/− 5.0 | 1.5 | 3.5 | 6.2 |
| *MCF-7 | 2641 ± 555 | 1.7 | 4.8 | 9.0 |
| *231− | ND | >10 | >10 | >10 |
| *231+ | 1800 ± 50 | 1.8 | 9.0 | >10 |
| HMEC 1585 | <10 | >10 | NA | NA |

ND: not detected.

$O_2$ consumption increased ~40-fold in 4 h with β-lap when 231-NQ+ versus 231-NQ− cell extracts were used (FIG. 28B). β-Lap redox cycling was not observed when 231-NQ− cell extracts were used, even in the presence of 15 μM β-lap (FIG. 28B). Importantly, $O_2$ consumption in NQO1+ extracts in the presence of dicoumarol was statistically identical to that noted from 231-NQ− cells (FIG. 28B). These data support the hypothesis that β-lap undergoes redox cycling in NQO1$^+$ cells, consuming $O_2$ during the spontaneous non-enzymatic, two one-electron back reactions (FIG. 28A). NQO1-dependent $O_2$ consumption was accompanied by dramatic increases in $O_2^{.-}$ (FIG. 28C) and $H_2O_2$ (FIG. 28D). Since NQO1 is primarily a cytosolic protein, dramatic elevations in cytosolic $H_2O_2$ levels are likely the major ROS species required for DNA base and single-strand break (SSBs) formation previously noted in NQO1+ cancer cells exposed to β-lap (Bentle et al., *J. Biol. Chem.* 2006; 281:33684-96). The absence of significant ROS in NQO1− cells strongly suggested that within the 2 h exposure of cells to β-lap, the drug was a relatively poor substrate for one-electron oxidoreductases, mediated by b5R and p450R (FIG. 28A). In contrast, exposure of cells to doxyrubicin (DOX, 5 μM, 2 h) or $H_2O_2$ (200 μM, 2 h) resulted in statistically equivalent $O_2^=$ or $H_2O_2$ levels, respectively, in 231-NQ− or 231-NQ+ cells.

2. Lethal β-Lap Doses Cause Threshold Levels of DNA Damage Required for PARP1 Hyperactivation Materials and Methods Relative Survival Assays:

Cells were cultured and treated as described above. Relative survival assays, using DNA content measurements by Hoechst fluorescence in a Perkin Elmer HTS 7000 Bio Assay Reader microtitre plate reader over a 7-10 day period, with or without 2-4 hour drug treatments, were performed as described (Pink et al., *J Biol. Chem.* 2000; 275:5416-24). Experiments were repeated at least three times, and data expressed as relative survival (treated/control×100%) means±SEM. Results using this assay directly correlated with colony forming ability assays (Pink et al., *J Biol. Chem.* 2000; 275:5416-24). The multi-target model was used to describe the shape of relative survival curves. In this model, a final slope ($D_0$) resulting from multiple-event killing and quasithreshold ($D_q$) doses were used to represent the size or width of the shoulder of the curve. The extrapolation number (n) is also a measure of the width of the shoulder. The three parameters, n, $D_o$, and $D_q$ were related by the expression: $\log_e n = D_q/D_o$.

Long Term Survival Assays:

Long-term relative survival assays were monitored over a 7-10 day period as previously described (Pink et al., *J Biol. Chem.* 2000; 275:5416-24) and as described above. Cells were treated with β-lap with or without dicoumarol for 2 h. DNA content was determined by Hoechst fluorescence in a Perkin Elmer HTS 7000 Bio Assay microtitre plate reader as described (Pink et al., *J Biol. Chem.* 2000; 275:5416-24). Data were expressed as relative survival (treated/control× 100%). Experiments were repeated at least three times, and data expressed as relative survival means±SEM. Results using this assay directly correlated with colony forming ability assays (Pink et al., *J Biol. Chem.* 2000; 275:5416-24). Human mammary epithelial cells were plated in 48 well dishes in growth media containing a 50:50 mixture of MGEM/DME:F12 medium supplemented with insulin, human epidermal growth factor and hydrocortisone.

Comet Assays:

DNA damage was assessed by alkaline comet assays and tail migration distance measured (Bentle et al., *J Biol. Chem.* 2006; 281:33684-96). Comet tails were visualized using an inverted Nikon Eclipse TE2000-S fluorescent microscope (Melville, N.Y.) and MetaMorph version 6.3 software (Molecular Devices, Downingtown, Pa.). Images were captured using a QImaging Retiga 2000R digital camera (Burnaby, BC, Canada) and analyzed using NIH ImageJ software. Comet tail lengths were measured in microns and mean lengths, ±SEM reported from three independent experiments performed in triplicate.

Western-Blot Analyses for PARP1 Cleavage:

MCF-7 cells seeded in 10 cm dishes were treated with 4 μM β-lap in the absence or presence of 1000 U of catalase dissolved in hepes buffer pH 7.4 for 2 h. Cells were then given fresh media and incubated at 37° C. for 24 h. Cells were then harvested in PARP1 lysis buffer. Lysates were resolved in 10% SDS-PAGE and immunoblotted onto PVDF membranes and probed with a monoclonal PARP1 antibody (SC-8007).

Results

The lethality responses of NQO1+ human cancer cells exposed to increasing concentrations of β-lap are rather sharp, where 1-2 μM treatments for 2-4 h were not lethal, but incremental increases to 2-3 μM caused >90% cell death responses indicated by strong TUNEL staining (Pink et al., *J Biol. Chem.* 2000; 275:5416-24; Bentle et al., *J Biol. Chem.* 2006; 281:33684-96; Reinicke et al., *Clin Cancer Res.* 2005; 11:3055-64). It was hypothesized that these sharp dose-responses were due to futile cycling of β-lap in NQO1+ cells expressing ~100 units of NQO1 (20). Accordingly, sublethal (1 μM, 2 h) and lethal (>2 μM, 2 h) β-lapachone doses were defined in 231-NQ+ cells (FIG. 30A), while 231-NQ-cells and normal human mammary epithelial cells (FIG. 30B and FIG. 31) remained non-responsive. Although ROS generation (monitored by percent GSSH oxidation, % GSSG formation) showed no statistical differences (p>0.5) in ROS formed over time in 231-NQ+ cells (FIG. 30C), pre- and co-treatments with the chemical ROS scavenger N-acetyl cysteine (NAC) protected against the lethal effects of 2 μM β-lap, but not 3 μM. This suggested that scavengers of ROS may represent a significant cytoprotective factor in the lethal responses of NQO1+ cells to β-lap, but that such weak scavenging can be easily overcome. Only minor oxidative stress was noted in 231-NQ− cells (FIG. 30D).

Comet assays were then used to assess the extent of DNA lesions (base damage, SSBs and DSBs) caused by various doses of β-lap in 231-NQ+ versus 231-NQ− cells (FIG. 32A). Although a sublethal dose of 1 μM β-lap produced significant GSSG formation (FIG. 30C), this same dose did not cause significant DNA damage over the course of a 2 h treatment (FIG. 32A). In contrast, 2 μM β-lap (an ~LD70 dose), as well as lethal doses of 4 and 6 μM β-lap, induced significant and dose-increasing DNA damage over time (FIG. 32A), consistent with elevated GSSG levels (FIG. 30C). Similar treatments of 231-NQ-cells with varying doses of β-lap did not result in significant DNA lesions, consistent with the lack of ROS and $H_2O_2$ formation and lethality in NQO1− cells.

Cell death in NQO1+ cells after β-lap treatment was accompanied by dramatic NAD+ losses due to PARP1 hyperactivation and subsequent programmed necrosis (REF). Indeed, while exposure of 231-NQ+ cells to nonlethal doses of β-lap (1 μM) did not result in measurable PAR formation, loss of NAD+ or DNA lesions, cytotoxic doses of β-lap (>2 μM) resulted in significant NAD+ pool loss (FIGS. 30A, 32B, 32C), consistent with PARP-1 hyperactivation (Bentle et al., *J Biol. Chem.* 2006; 281:33684-96), indicated by the steady state accumulation of post-translational PAR-modified and inactivated PARP1 (PAR, FIG. 32C). Peak PAR formation was noted 30 mins after 2 μM β-lap, levels that peaked earlier in time (mins) with increasing doses of β-lap (FIG. 32C, compare 2 μM to 6 μM β-lap exposures). The decreased time noted for peak PAR formation in response to higher doses of β-lap was accompanied by rapid steady state PAR losses due to the dramatic lowering of intracellular NAD+ levels (FIG. 32B).

3. Catalase Detoxifies β-lap-Induced $H_2O_2$ Formation and is Cytoprotective

Materials and Methods

Cell culture, treatment, ROS assays, survival assays, and comet assays were performed as described above.

TUNEL Assays:

TUNEL was performed (Tagliarino et al., *J Biol. Chem.* 2001; 276:19150-9) on control or β-lap-treated cells as described and analyzed by flow cytometry according to the manufacturer's protocol (APO-DIRECT kit, Pharmingen, San Diego, Calif.). Data were expressed as means, +SEM from three separate experiments.

Results

Since $O_2^-$ and $H_2O_2$ were specifically formed in β-lap-treated 231-NQ+ cells, and prior evidence demonstrated exclusive formation of NQO1-dependent SSBs without formation of DSBs (Tagliarino et al., *J Biol. Chem.* 2001; 276:19150-9; Bey et al., *Proc Natl Acad Sci USA*, 2007; 104:11832-7; Dong et al., *Cancer Res.* 2010; 70:8088-96), it was suspected that catalase activities in cells (that converts $H_2O_2$ to oxygen and water) would be cytoprotective. Indeed, exogenous addition of 1000 units of catalase significantly lowered $H_2O_2$ levels in β-lap-treated 231-NQ+ cells (FIG. 33A, left panel), while its addition had no affect on $O_2$ formation (FIG. 33A, left panel). Exogenous $Mn^{2+}$-dependent superoxide dismutase (MnSOD) administration decreased $O_2^-$ formation (FIG. 33A, right panel), while slightly increasing $H_2O_2$ levels (FIG. 33A, right panel). Co-addition of exogenous SOD and catalase was more efficient at lowering $H_2O_2$ (FIG. 4A, left panel) and $O_{21}$ (FIG. 33A, right panel) levels. These results strongly suggested that exogenous catalase administration effectively prevented ROS (specifically $H_2O_2$) production in β-lap-treated 231-NQ+ cells, and that SOD addition augmented this scavenging activity. Finally, exogenous overexpression of catalase using a CMV-driven catalase expression vector (Open Biosystems) in MCF-7 cells (FIG. 33B), significant spared NQO1+ cells from β-lap induced lethality at doses ranging from 2-4 μM.

Addition of exogenous catalase (FIG. 32) was far more effective than NAC treatments (FIG. 30A). Catalase (≥500 units) significantly protected cells from the lethal effects of β-lap-in 231-NQ+ cells (FIG. 33C), while the survival of β-lap-treated 231-NQ-cells remained unaffected (FIG. 33D). Exogenous co-administration of catalase with MnSOD significantly decreased the concentration of catalase required to effectively prevent β-lap-induced lethality, measured by long-term survival (FIG. 33E); For example, only 125 U of exogenous catalase was administered to the medium (compare data for 125 U catalase without and with MnSOD, FIGS. 33C and 33E, p<0.03, respectively). Similar enhanced cytoprotection of catalase was noted at all doses examined when combined with MnSOD (compare catalase treatments without or with MnSOD, (FIGS. 33C and 33E (p≤0.01), respectively). In contrast, addition of exogenous catalase did not influence the survival of 3-lap-resistant 231-NQ− cells in the presence or absence of MnSOD (FIG. 33F).

Accordingly, catalase also suppressed downstream lethality responses in NQO1+231 cells, monitored by comet assays (FIG. 34A), PAR-PARP1 formation (FIG. 34C), NAD+ loss (FIG. 34D). Catalase administration also prevented atypical PARP1 and p53 proteolytic cleavage (FIG. 34E and FIG. 35) and apoptotic responses (effectively blocked TUNEL responses, FIG. 34F) that are uniquely associated with β-lap-induced programmed necrosis. In contrast, catalase did not affect β-lap-resistant 231-NQ− cells (FIG. 34A).

4. β-Lap-Induced Programmed Necrosis is Accompanied by AIF Translocation to the Nucleus Materials and Methods Cell culture and treatment were performed as described above.

Western Blotting and Antibodies—

For Western-blot analyses for PARP1 cleavage-MCF-7 cells seeded in 10 cm dishes were treated with 4 μM β-lap in the absence or presence of 1000 U of catalase dissolved in hepes buffer pH 7.4 for 2 h. Cells were then given fresh media and incubated at 37° C. for 24 h. Cells were then harvested in PARP1 lysis buffer. Lysates were resolved in 10% SDS-PAGE and immunoblotted onto PVDF membranes and probed with a monoclonal PARP1 antibody (SC-8007). Western blot analyses were performed as described (Pink et al., *J Biol. Chem.* 2000; 275:5416-24). α-PARP1 was utilized at a dilution of 1:8,000 (Abcam Inc., Cambridge, Mass.), anti-α-tubulin was utilized at a dilution of 1:10,000 (Santa Cruz, Santa Cruz, Calif.), and α-PAR was utilized at a dilution of 1:2000 (BD-Pharminigen, San Jose, Calif.). Relative PAR levels were calculated by densitometric analyses by NIH ImageJ using PARP1 loading controls. Measurements were normalized to t=0 levels. Western blots shown are representative of separate experiments performed at least three times.

Results

β-Lap mediated lethality is often referred to as programmed necrosis, since it displays attributes of both necrosis (energy independent) and apoptosis (condensation of nuclei, TUNEL+ cell formation in 12-72 h following a 2 h pulse). Exposure of MCF-7 cells (FIG. 36A) to a 2 h pulse of 4 μM β-lap induced previously reported atypical 60 kDA proteolytic cleavage fragment of PARP1 (Pink et al., *J Biol. Chem.* 2000; 275:5416-24). In contrast, staurosporine (STS) treatment yielded classical PARP1 cleavage fragment (~89 kDa, FIG. 36A). To delineate the role of calcium in this unique programmed necrotic cell death pathway, MCF-7 cells were pre-loaded with the calcium chelator, BAPTA-AM, or the pancaspase inhibitor, Z-VAD, prior to β-lap exposure. β-Lap-mediated proteolyis of PARP1 (and long-term lethality) was prevented by pre-treating NQO1+ cells with BAPTA-AM, similar to the effects of co-treating cells with dicoumarol, an NQO1 inhibitor. In contrast, pretreatment with Z-VAD, a pan-caspase inhibitor, was ineffective at inhibiting β-lap-induced proteolysis or lethality (FIG. 36A), while it prevented classical staurosporine-mediated apoptotic PARP1 cleavage, similar to previous reports (Kaufmann et al., *Oncogene* 2003; 22:7414-30).

The affects of β-lap treatment on AIF release from mitochondria were monitored in exposed NQO1+ cells. Exposure of MCF-7 cells caused activation and movement of AIF from mitochondria (DMSO, FIG. 36B) to the nuclei of exposed cells (see β-lap-exposed MCF-7− cells, 4-24 h post-treatment, FIG. 36A). Activation of AIF in β-lap-treated NQO1+231 breast cancer cells was consistent with the kinetics of activation of μ-calpain after β-lap exposures (Tagliarino et al., *J Biol. Chem.* 2001; 276:19150-9; Tagliarino et al., *Cancer Biol Ther.* 2003; 2:141-52. 25). Activation of AIF was blocked by BAPTA-AM (FIG. 36C), as well as co-treatment with 1000 U of catalase (FIG. 36D). However, siRNA-mediated AIF knockdown only partially decreased the lethality of β-lap-treated MCF-7 cells (FIG. 36E); transient and/or stable siRNA (or shRNA for stable transfection) knockdown of AIR were/was performed as described (Li et al., *Clin. Cancer Res.* 2011; 17:275-85). We theorized that this was most likely due to the simultaneous activation of other cell death mediators, including post-translational modification/activation of GAPDH (FIG. 36F), that can mediate apoptotic-like cell death responses (Hara et al., *Nat Cell Biol.* 2005; 7:665-74). Thus, β-lap-induced programmed necrotic responses (FIG. 37) are associated with a number of downstream cell death mediators, including dramatic alterations in metabolism (NAD+ (FIG. 4B) and ATP (Bentle et al., *J Biol. Chem.* 2006; 281:33684-96) losses due to PARP1 hyperactivation, DNA damage induction via ROS production, and activation of various proteases designed to 'clean up' dead cells.

Discussion

Chemo-resistant triple-negative (ER−, PR−, Her2/Neu−) MDA-MB-231 breast cancer cells were used to link NQO1-dependent futile cycling of β-lap to ROS-induced DNA damage and PARP1 hyperactivation. Threshold level responses to β-lap were denoted by a dose-dependent trigger, most likely mediated by formation of supralethal superoxide levels that in turn results in dramatic elevations in hydrogen peroxide production that induced DNA damage and PARP1 hyperactivaton.

The data show that exogenous catalase addition or overexpression prevents β-lap lethality, consistent with the notion that hydrogen peroxide is the primary obligate ROS species necessary for this agent's lethal effects, and consistent with the specific induction of SSBs caused by this tumor-selective antitumor agent. Furthermore, it was also shown that co-addition of SOD specifically enhanced the efficacy with which catalase prevented β-lap-induced cell death. These data suggest that normal tissue, which typically have higher levels of catalase that cancer cells could be selectively spared from toxicity of this agent. Alternatively, cancer cells overexpressing catalase and/or MnSOD would require higher doses of β-lap to avoid "sublethal therapeutic treatments." The ratio of NQO1 to calatase levels may therefore be a major determinant of tumor-selectivity for β-lapachone and other drugs that work through NQO1 "bioactivation." Therefore, catalase, as well as SOD, are factors that should be evaluated and taken into consideration for therapies utilizing β-lap. Catalase protects cells from hydrogen peroxide induced lipid peroxidation that damages membranes and cellular organelles. Although exogenous catalase enhanced survival at low doses of β-lap exposure, excessive ROS formation (possibly including additional ROS species) by β-lap (>6 μM) could not be inhibited by catalase alone. SOD alone did not spare, but either had no affect or enhanced cell β-lap-induced lethality, consistent with the obligate role of $H_2O_2$ in β-lap lethality. However, combining SOD with catalase had a pronounced sparing effect at doses (>6 μM), presumably by converting superoxide to $H_2O_2$ that can be detoxified to ($O_2+H_2O$).

The unique killing mechanism elicited by β-lap is initiated by PARP1 hyperactivation. PARP1, when normally activated during SSB repair, uses NAD+ to add poly-(ADP-ribosyl) polymer modification to specific DNA repair proteins as well as itself, which ultimately inactivates PARP1 and causes the enzyme to detach from DNA. This modification results in a dramatic loss of NAD+ that ultimately depletes essential nucleotide pools needed for cellular energy production, namely ATP. Thus, hyperactivation of PARP1 leads to cellular catastrophe due to nucleotide pool loss that inactivates DNA repair machinery. Catalase addition prevented PARP1 hyperactivation and blocked AIF from migrating to the nuclei of exposed cells. However, AIF knockdown only partially and weakly protected cells from the lethal affects of β-lap. Multiple cell death signal pathways may therefore be activated in response to β-lap exposure. In fact, in addition to AIF release, specific modification of GAPDH was observed (presumably via S-nitrosylation of this protein), that has been shown to elicit endonuclease activity related to apoptosis, was activated. Atypical PARP1 proteolysis is a hallmark of β-lap induced cell death. Furthermore, it has been demonstrated that atypical proteolysis is due to μ-calpain activation and translocation. Since catalase protected cells from ROS-induced DNA-damage, AIF release, proteolysis of PARP1 and GAPDH posttranslational modification, ROS formation clearly plays an essential and upstream role in β-lap-mediated lethality. Expression of ROS scavenging enzymes, particularly catalase, must be factored into determining the efficacious doses of β-lap to be used in a given cancer.

Example 12

Effect of β-Lapachone on NQO1 Genotyped Cancer Cells

Cell lines, mostly from a 5-panel nonsmall cell lung cancer panel from the UT Southwestern SPORE, were assessed for NQO1 polymorphism status and then monitored for NQO1 enzyme assays using β-lapachone or the standard menadione substrates. Cell line responses to β-lapachone exposures (μM, 2 h) were then assessed and lethal doses causing 50% lethality with or without dicoumarol (40 μM) co-treatments were recorded. NQO1*2/*2 and *3/*3 polymorphisms were detected from NQO1 *1/*1 wild-type sequences by PCR-RFLP. Genomic DNA was extracted from the cells using Qiagen spin columns. Using previously described oligonucleotide primers, PCR products underwent gel electrophoresis. Final genotyping was determined based on the size and pattern of separated bands diagnostic for *1/*1 (wild-type), or polymorphic *2/*2 or *3/*3 NQO1 polymorphisms.

Results

NQO1*3 polymorphic cells have relatively low enzymatic levels using menadione, but higher levels using β-lapachone as substrates (Table 4). Similarly, unlike *2 cells, these cells appear to be responsive to β-lapachone therapy. Interestingly and importantly, these cells appear to not be blocked by dicoumarol, suggesting that the enzyme made may use NAD(P)H exclusively, since dicoumarol is an inhibitor of NQO1 by mimicking NADH. These data strongly suggest that patients with *3 tumors will still respond to β-lapachone as well as other NQO1 bioactivatable drugs.

TABLE 4

Effect of β-lapachone on NQO1 genotyped cancer cells.

| Number | Cell Line/Type | NQO1 Genotype | NQO1 activity nMoles/min/μg Men; β-Lap | β-Lap Lethality $LD_{50}$ | $LD_{50}$ + DIC |
|---|---|---|---|---|---|
| 1 | Calu-3/NSCLC | *3/*3 | 48 +/− 3; 243 +/− 2 | 2.4 | 3 |
| 2 | H2009/NSCLC | *3/*3 | 4.0 +/− 1; 120 +/− 3 | 4.3 | 5.4 |
| 3 | HCC1171/NSCLC | *3/*3 | 98 +/− 17; 369 +/− 9 | 3 | 2 |
| 4 | T47D/BreastCancer | *3/*3 | 32 +/− 2; 138 +/− 3 | 4 | 4 |
| 5 | H1993 | *1/*1 | 1170 +/− 30; 1940 +/− 12 | 1.8 | >10 |
| 6 | H2073 | *1/*1 | 1340 +/− 20; ND | 1.8 | >10 |
| 7 | H1648 | *1/*1 | 1370 +/− 17; ND | 4.1 | >20 |
| 8 | H322 | *1/*1 | 1234 +/− 40; ND | 5.7 | >20 |
| 9 | HCC44 | *1/*2 | 148 +/− 14; 879 +/− 14 | 2.8 | >10 |
| 10 | H292 | *1/*2 | 169 +/− 17; ND | 1.8 | >10 |
| 11 | HCC2935 | *1/*3 | 134 +/12; ND | 1.0 | >10 |
| 12 | H596/NSCLC | *2/*2 | <1.0 +/− 0.01 | >20 | >40 |
| 13 | H2882/NSCLC | *2/*2 | <1 +/− 0.01 | >20 | >40 |
| 14 | HCC366/NSCLC | *2/*2 | <1 +/− 0.01 | >10 | >10 |
| 15 | MDA-MB-231/Breast | *2/*2 | 1 +/− 0.05 | >10 | >10 |
| 16 | MDA-MB-468/Breast | *2/*2 | <1 +/− 0.01 | >10 | >10 |
| 38 | H596/NSCLC | *2/*2 | <1 +/− 0.01 | >10 | >10 |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A method of treating an individual having cancer with an NQO1 bioactivatable drug comprising:
    (a) measuring the protein or enzymatic level of NQO1 and catalase in cancer cells from the individual;
    (b) detecting at least about a 50-fold increased ratio of NQO1:catalase in the cancer cells compared to a NQO1:catalase ratio in corresponding normal tissues; and
    (c) administering an NQO1 bioactivatable drug to the individual for cancer treatment.

2. The method of claim 1, wherein the ratio of the NQO1 level over the catalase level in the cancer cells from the individual is at least about 60-fold or at least about 70-fold of the ratio in a normal tissue.

3. The method of claim 2, wherein the normal tissue is from the individual.

4. The method of claim 1, wherein the NQO1 bioactivatable drug is a β-lapachone compound, streptonigrin, or deoxynyboquinone (DNQ).

5. The method of claim 1, wherein the cancer is lung cancer, prostate cancer, breast cancer, pancreatic cancer, colon cancer or melanoma.

6. The method of claim 1, wherein the protein level of the NQO1 expression and/or the catalase expression is measured by the enzymatic activity or the amount of the protein in the cancer cells and in the normal tissue from the individual.

7. The method of claim 1, wherein the individual is a human.

8. The method of claim 1, wherein the normal tissue is an associated normal tissue.

9. The method of claim 1, wherein the cancer cells are from a cancer biopsy from the individual or circulating cancer cells from the individual.

* * * * *